United States Patent
Dixon et al.

(10) Patent No.: US 11,365,402 B2
(45) Date of Patent: *Jun. 21, 2022

(54) INTERNAL PROTEIN TAGS

(71) Applicant: Promega Corporation, Madison, WI (US)

(72) Inventors: Andrew S. Dixon, Verona, WI (US); Lance P. Encell, Fitchburg, WI (US); Thomas Machleidt, Madison, WI (US); Marie Schwinn, Madison, WI (US); Keith Wood, Mt. Horeb, WI (US); Monika Wood, Mt. Horeb, WI (US); Kris Zimmerman, Madison, WI (US)

(73) Assignee: Promega Corporation, Madison, WI (US)

(*) Notice: Subject to any disclaimer, the term of this patent is extended or adjusted under 35 U.S.C. 154(b) by 402 days.

This patent is subject to a terminal disclaimer.

(21) Appl. No.: 15/980,406

(22) Filed: May 15, 2018

(65) Prior Publication Data
US 2019/0352623 A1 Nov. 21, 2019
US 2021/0403886 A9 Dec. 30, 2021

Related U.S. Application Data

(63) Continuation of application No. 14/852,096, filed on Sep. 11, 2015, now Pat. No. 9,969,991.

(60) Provisional application No. 62/049,875, filed on Sep. 12, 2014.

(51) Int. Cl.
| | |
|---|---|
| *C12N 9/14* | (2006.01) |
| *C07K 14/315* | (2006.01) |
| *C07K 14/475* | (2006.01) |
| *G01N 33/533* | (2006.01) |
| *G01N 33/535* | (2006.01) |

(52) U.S. Cl.
CPC .............. *C12N 9/14* (2013.01); *C07K 14/315* (2013.01); *C07K 14/475* (2013.01); *C12Y 308/01005* (2013.01); *G01N 33/533* (2013.01); *G01N 33/535* (2013.01); *C07K 2319/61* (2013.01)

(58) Field of Classification Search
CPC ...... G01N 33/533; G01N 33/535; C12N 9/14; C12N 9/0069; C12Y 113/12007; C12Y 113/12005; C12Y 308/01005; C07K 2319/61; C07K 14/43595; C07K 14/315; C07K 14/475; C12Q 1/66
See application file for complete search history.

(56) References Cited

U.S. PATENT DOCUMENTS

| | | | |
|---|---|---|---|
| 8,557,970 B2 | 10/2013 | Encell et al. | |
| 8,669,103 B2 * | 3/2014 | Binkowski | C12N 9/0004 435/325 |
| 9,969,991 B2 * | 5/2018 | Dixon | C07K 14/47 |
| 2010/0281552 A1 | 11/2010 | Encell et al. | |
| 2014/0120548 A1 | 5/2014 | Encell et al. | |
| 2014/0194307 A1 | 7/2014 | Hitko et al. | |
| 2014/0223590 A1 | 8/2014 | Binkowski et al. | |
| 2014/0227759 A1 | 8/2014 | Binkowski et al. | |
| 2014/0348747 A1 | 11/2014 | Dixon et al. | |

FOREIGN PATENT DOCUMENTS

WO  WO 2016/040835   3/2016

OTHER PUBLICATIONS

Brown et al., Facile approach for constructing TEV insertions to probe protein structure in vivo. Biotechniques. Dec. 2006;41(6): 721-4.
International Search Report and Written Opinion for PCT/US2015/049741, dated Jan. 28, 2016, 17 pages.

* cited by examiner

*Primary Examiner* — Ganapathirama Raghu
(74) *Attorney, Agent, or Firm* — Casimir Jones SC; David W. Staple

(57) ABSTRACT

Provided herein are substantially non-luminescent peptide/polypeptide tags that are inserted internally within a protein of interest or between N-terminal and C-terminal peptides/polypeptides. Interaction of the internally-inserted tag with a complement polypeptide/peptide that is also substantially non-luminescent results in the formation a bioluminescent reporter complex.

30 Claims, 18 Drawing Sheets
Specification includes a Sequence Listing.

HeLa cells labeled with TMR-HaloTag ligand

78/79 18/19 98/99

C-term 86 N-term-86 HaloTag

INTERNAL PROTEIN TAGS

CROSS-REFERENCE TO RELATED APPLICATION

The present application is a divisional of U.S. patent application Ser. No. 14/852,096, filed Sep. 11, 2015, now U.S. Pat. No. 9,969,991, which claims priority to U.S. Provisional Patent Application Ser. No. 62/049,875 filed Sep. 12, 2014, each of which is hereby incorporated by reference in its entirety.

SEQUENCE LISTING

The text of the computer readable sequence listing filed herewith, titled "33980-403_SEQUENCE_LISTING_ST25", created Oct. 15, 2020, having a file size of 2,025,000 bytes, is hereby incorporated by reference in its entirety.

FIELD

Provided herein are substantially non-luminescent peptide/polypeptide tags that are inserted internally within a protein of interest or between N-terminal and C-terminal peptides/polypeptides. Interaction of the internally-inserted tag with a complement polypeptide/peptide results in the formation a bioluminescent reporter complex.

BACKGROUND

Tagging of proteins with reporters or affinity tags is commonly used to analyze protein function and behavior. In general, genetic fusions are generated using either the C- or N-terminus of the protein of interest.

SUMMARY

Provided herein are substantially non-luminescent peptide/polypeptide tags that are inserted internally within a protein of interest or between N-terminal and C-terminal peptides/polypeptides. Interaction of the internally-inserted tag with a complement polypeptide/peptide results in the formation of a bioluminescent reporter complex.

In some embodiments provided herein are compositions, systems, methods etc. comprising a protein or polypeptide with an internal tag inserted therein. In some embodiments provided herein are compositions, systems, methods etc. comprising an internal tag inserted between C-terminal and N-terminal peptides/polypeptides. In certain embodiments, a structural complement sequence (or the internal tag) is also provided (e.g., free or as a fusion (e.g., internal or terminal)). In some embodiments, both the internal tag and the structural complement are substantially inactive (e.g., lacking enzymatic activity (e.g., substantially non-luminescent, etc.)). In some embodiments, the internal tag and the structural complement have high affinity for each other and form a complex (e.g., stable complex) when in solution together. In other embodiments, the internal tag and the structural complement have low affinity for each other and do not form a complex (e.g., stable complex) unless brought together by external factors/forces (e.g., interaction elements fused to the internal tag and structural complement). In some embodiments, a complex of the internal tag and the structural complement produces a detectable activity (e.g., luminescence in the presence of substrate).

In some embodiments, an internal fusion is provided. In some embodiments, an internal tag sequence (e.g., one that produces detectable activity when complexed with a structural complement) resides internally within the sequence of a protein or polypeptide sequence of interest. In some embodiments, an internal tag resides within the protein or polypeptide sequence of interest at a location that maintains: (i) the ability of the internal tag to form an active complex with a structural complement, and (ii) structural or activity characteristics of the protein or polypeptide of interest. In some embodiments, the structure or activity of one or more domains of interest of the protein or polypeptide of interest are uninterrupted by the presence of the internal tag within the sequence of the polypeptide or protein of interest. In some embodiments, the internal tag resides at a location within the protein of interest such that it is surface accessibly exposed on the surface of the protein of interest. In some embodiments, the internal tag resides at a loop of the protein of interest such that disruption to the structure and/or activity of the protein of interest is reduced/minimized.

In some embodiments, an internal tag sequence (e.g., one that produces detectable activity when complexed with a structural complement) resides internally between a C-terminal peptide/polypeptide and an N-terminal peptide/polypeptide. In some embodiments, an internal tag is linked to C-terminal and N-terminal peptides/polypeptides at locations that maintain: (i) the ability of the internal tag to form an active complex with a structural complement, and (ii) structural or activity characteristics of the C-terminal and N-terminal peptides/polypeptides.

In some embodiments, an internal tag and a complement peptide/polypeptide are fused to and/or inserted within separate domains of the same multi-domain protein. Upon folding of the protein, or a conformational change, activity from the complex of the internal tag and complement is detectable.

In some embodiments, methods of using an internal tag are provided. Some of the following embodiments are described for use with an internal tag and a protein of interest; however, whenever appropriate, they may also find use with an internal tag between N-terminal and C-terminal peptides/polypeptides.

In some embodiments, methods are provided for detecting the presence and/or location of a protein/polypeptide of interest using an internal tag and a structural complement that form an active complex upon association. In some embodiments, the presence and/or location in a sample (e.g., cell, subcellular location, in vitro sample, etc.) of a polypeptide with an internal tag is determined by adding a free structural complement having high affinity for the internal tag to the sample. Detection of the activity produced by complex formation indicates the presence and/or location of the protein/polypeptide of interest. In some embodiments, an active complex of an internal tag and a structural complement are detected in environments including, but not limited to: an in vitro sample, cell lysate, within living cells, within a living organism, etc.

In some embodiments, methods are provided for detecting interactions between a protein of interest and selected interaction partners (e.g., nucleic acids, peptides, proteins, polypeptides, small molecules, lipids, etc.) using an internal tag and a structural complement that form an active complex upon association. In some embodiments, the interaction of (i) a protein of interest with an internal tag and (ii) an interaction partner (e.g., nucleic acids, peptides, proteins, polypeptides, small molecules, lipids, etc.) linked to a structural complement having low affinity for the internal tag is detected upon formation of the active complex between the internal tag and the structural complement. In some embodiments, interactions are detected in environments including, but not limited to: an in vitro sample, cell lysate, within living cells, within a living organism, etc.

In some embodiments, methods are provided for detecting intramolecular interactions within a protein of interest by labeling the protein of interest with an internal tag and a complement peptide/polypeptide (internal or end-labeled with complement). A conformational change, folding, or other intramolecular interaction is detected by formation of a complex of the internal tag and the complement.

In some embodiments, the efficiency of complementation (and formation of an active complex and detectable luminescence) of an internal tag residing within a protein or polypeptide of interest and its structural complement is affected by one or more of: (i) conformational changes in the protein or polypeptide of interest (e.g., conformational changes that affect the accessibility of the internal tag to the structural complement), (ii) molecular interactions of the protein or polypeptide of interest (e.g., with a drug), and/or environmental changes (e.g., changes to conditions).

In some embodiments provided herein are compositions comprising a peptide and/or polypeptide tags that: (i) are not fragments of a preexisting protein, (ii) are substantially non-luminescent, (iii) are inserted internally within a protein of interest, and (iv) form a luminescent complex with a structurally complementary polypeptide and/or peptide. Also provided herein are luminescent complexes of the internal peptide and/or polypeptide tags with their complement polypeptide and/or peptide, and methods of generating an optically detectable bioluminescent signal upon formation of such complexes. In some embodiments provided herein are two or more substantially non-luminescent peptides and/or polypeptides, one or more of which are provided as internal protein tags that, when brought together, assemble into a bioluminescent complex. In some embodiments, a substantially non-luminescent peptide and/or polypeptide internal tag and its complement polypeptide/peptide assemble into a bioluminescent complex. In some embodiments, the complement peptide/polypeptide is also an internal tag. In other embodiments, the complement is a terminal (e.g., N-terminal of C-terminal) tag. In other embodiments, the complement is not associated with another peptide, polypeptide, or protein (e.g., free). In some embodiments, three or more substantially non-luminescent peptide and/or polypeptide units, one or more of which are internal protein tags assemble into a bioluminescent complex (e.g., ternary complex, tertiary complex, etc.). In some embodiments provided herein are technologies for detecting internally tagged proteins or polypeptides via the formation of a bioluminescent complex of the otherwise substantially non-luminescent internal tag and its substantially non-luminescent structural complement. In some embodiments, interactions between a protein of interest and another moiety (e.g., protein, peptide, nucleic acid, lipid, small molecule, etc.) are identified by detection of the formation of a bioluminescent complex between a substantially non-luminescent internal tag of the protein of interest and a substantially non-luminescent structural complement of the internal tag. In some embodiments, such compositions are provided in environments including, but not limited to: an in vitro sample, cell lysate, within living cells, within a living organism, etc.

In some embodiments, interactions between different regions of a protein, or domains of a multi-domain protein, are detected by labeling the different regions/domains with an internal tag and complement. Activity from the complex of the internal tag and complement indicates intra-protein interactions (e.g., conformational change, folding, etc.).

In some embodiments, the complex of a substantially non-luminescent internal tag and its substantially non-luminescent structural complement catalyzes a chemical reaction of an appropriate substrate into a high energy state, and light is emitted. In some embodiments, a bioluminescent complex of an internal protein tag and its structural complement exhibits luminescence in the presence of substrate (e.g., coelenterazine, furimazine, etc.).

Although the embodiments described herein primarily describe and refer to the formation of a luminescent complex (e.g., comprising at least one substantially non-luminescent tag and its substantially non-luminescent complement) complementary, it is noted that the present technology can equally be applied to other detectable attributes (e.g., other enzymatic activities, generation of a fluorophore, generation of a chromophore, etc.). The embodiments described herein relating to luminescence should be viewed as applying to internal tags that are substantially non-enzymatically active amino acid chains (e.g., peptides and/or polypeptides that are not fragments of a preexisting protein) and their structurally complementary polypeptide/peptide that also lack a specified detectable activity (e.g., enzymatic activity), and the enzymatically active complexes thereof. Provided herein are methods of generating a detectable activity (e.g., an enzymatic activity) upon association of a substantially non-enzymatically active, internal tag and its substantially non-enzymatically active complement peptide/polypeptide.

The invention is further directed to assays for the detection of molecular interactions (e.g., transient association, stable association, complex formation, etc.) between a protein (or polypeptide) of interest and another moiety (e.g., peptide, polypeptide, protein, nucleic acid, small molecule etc.) by inserting an internal tag into the protein of interest and tagging the other moiety (e.g., internally labeled, terminally labeled, etc.) with the structural complement of the internal tag, wherein no signal (e.g., substantially no signal) is produced in the absence of the molecular interaction between the protein of interest and the other moiety, but a detectable (e.g., bioluminescent) complex of the internal tag and its complement is produced upon interaction of the protein of interest and the other moiety. In such embodiments, assembly of the bioluminescent complex is operated by the molecular interaction of the protein of interest and the other moiety. If the protein of interest and the other moiety engage in a sufficiently stable interaction, the bioluminescent complex of the internal tag and its complement forms, and a bioluminescent signal is generated. If the protein of interest and the other moiety fail to engage in a sufficiently stable interaction, the bioluminescent complex does not form, or only weakly forms, and a bioluminescent signal is not generated or is substantially reduced (e.g., substantially undetectable, essentially not detectable, differentially detectable as compared to a stable control signal, etc.). In some embodiments, the magnitude of the detectable bioluminescent signal is proportional (e.g., directly proportional) to the amount, strength, favorability, and/or stability of the molecular interactions between the protein of interest and the other moiety.

In some embodiments, provided herein are internal tags comprising an amino acid sequence having less than 100% (e.g., 20% . . . 30% . . . 40% . . . 50% . . . 60% . . . 70% . . . 80%, 90% or more) sequence identity with SEQ ID NO: 2, wherein a detectable bioluminescent signal is produced when the peptide contacts a complement polypeptide of SEQ ID NO: 440. In some embodiments, provided herein are internal tags comprising an amino acid sequence having less than 100% and greater than 30% (e.g., >30%, >40%, >45%, >50%, >55%, >60%, >65%, >70%, >75%, >80%, >85%, >90%, >95%, >98%, >99%) sequence identity with SEQ ID NO: 2, wherein a detectable bioluminescent signal is produced when the peptide contacts a structurally complementary polypeptide of SEQ ID NO: 440. In some embodiments, a detectable bioluminescent signal is produced when the internal tag contacts a polypeptide having less than 100% and greater than 30% (e.g., >30%, >40%, >45%, >50%, >55%, >60%, >65%, >70%, >75%, >80%, >85%, >90%, >95%, >98%, >99%) sequence identity with SEQ ID NO: 440. In certain embodiments, the detectable bioluminescent signal is produced, or is substantially increased, when the internal tag associates with the polypeptide comprising or consisting of SEQ ID NO: 440, or a portion thereof. Although not limited to these sequences, the peptide amino acid sequence may be selected from amino acid sequences of SEQ ID NOS: 3-438 and 2162-2365. In some embodiments, polypeptides are provided that comprise an above described internal tag inserted into a protein or polypeptide of interest (e.g., not on the C- or N-terminus of the protein or polypeptide). In some embodiments, a structural complement of the internal tag is provided alone or as a tag (e.g., internal or terminal) of another moiety (e.g., protein, peptide, polypeptide, nucleic acid, lipid, small molecule, etc.). In certain embodiments, bioluminescent complexes are provided that comprise: (a) a first polypeptide having an internal tag (e.g., not located at the N- of C-terminus); and (b) a peptide or polypeptide comprising a structural complement of the internal tag; wherein, when associated, the internal tag and its structural complement emit a detectable bioluminescent signal in the present of an appropriate substrate. In some embodiments, the internal tag comprises an amino acid sequence having less than 100% and greater than 30% sequence identity with SEQ ID NO: 2 and a detectable bioluminescent signal is produced when the internal tag contacts a structurally complementary polypeptide of SEQ ID NO: 440 in the presence of substrate.

In some embodiments provided herein are internal tags comprising an amino acid sequence having less than 100% sequence identity with SEQ ID NO: 440, wherein a detectable bioluminescent signal is produced when the internal tag contacts a peptide of SEQ ID NO: 2 in the presence of substrate. In some embodiments, the present invention provides internal tags comprising an amino acid sequence having less than 100% and greater than 30% (e.g., >30%, >40%, >45%, >50%, >55%, >60%, >65%, >70%, >75%, >80%, >85%, >90%, >95%, >98%, >99%) sequence identity with SEQ ID NO: 440, wherein a detectable bioluminescent signal is produced when the internal tag contacts a peptide of SEQ ID NO: 2. In some embodiments, a detectable bioluminescent signal is produced when the internal tag contacts a peptide having less than 100% and greater than 30% (e.g., >30%, >40%, >45%, >50%, >55%, >60%, >65%, >70%, >75%, >80%, >85%, >90%, >95%, >98%, >99%) sequence identity with SEQ ID NO: 2. Although not limited to such sequences, the internal tag sequence may be selected from one of the amino acid sequences of SEQ ID NOS: 441-2156. In some embodiments, a detectable bioluminescent signal is produced when the internal tag associates with a peptide of SEQ ID NO: 2 in the presence of appropriate substrate. In certain embodiments, bioluminescent complexes are provided that comprise: (a) a first polypeptide having an internal tag (e.g., not located at the N- of C-terminus); and (b) a peptide or polypeptide comprising a structural complement of the internal tag; wherein, when associated, the internal tag and its structural complement emit a detectable bioluminescent signal in the present of an appropriate substrate. In some embodiments, the internal tag comprises an amino acid sequence having less than 100% and greater than 30% sequence identity with SEQ ID NO: 440 and a detectable bioluminescent signal is produced when the internal contacts a structurally complementary peptide of SEQ ID NO: 2 in the presence of substrate.

In some embodiments, provided herein are nucleic acids (e.g., DNA, RNA, etc.), oligonucleotides, vectors, etc., that code for any of the peptides, polypeptides (e.g., comprising internal tags, comprising terminal tags, etc.), proteins (e.g., comprising internal tags, comprising terminal tags, etc.), fusion proteins, etc., described herein. In some embodiments, a nucleic acid comprising or consisting of one of the nucleic acid sequences of SEQ ID NOS: 3-438 and 2162-2365 (e.g., coding peptide internal tags, coding for peptide structural complements) and/or SEQ ID NOS 441-2156 (e.g., coding polypeptide internal tags, coding for polypeptide structural complements) are provided. In some embodiments, other nucleic acid sequences coding for amino acid sequences of SEQ ID NOS: 3-438 and 2162-2365 and/or SEQ ID NOS 441-2156 are provided.

In certain embodiments provided herein are bioluminescent complexes comprising: (a) a first polypeptide having an internal (e.g., not at the N- or C-terminus) tag comprising an amino acid sequence having less than 100% sequence identity (e.g., <99%, <95%, <90%, <80%, <70%, <60%, <50%, etc.) with SEQ ID NO: 2; and (b) a second polypeptide comprising an amino acid sequence (e.g., internally or terminally) having less than 100% and greater than 30% (e.g., >30%, >40%, >45%, >50%, >55%, >60%, >65%, >70%, >75%, >80%, >85%, >90%, >95%, >98%, >99%) sequence identity with SEQ ID NO: 440, wherein the bioluminescent complex exhibits detectable bioluminescence in the presence of substrate. In certain embodiments, provided herein are bioluminescent complexes comprising: (a) a polypeptide comprising an internal tag comprising an amino acid sequence having less than 100% and greater than 30% (e.g., >30%, >40%, >45%, >50%, >55%, >60%, >65%, >70%, >75%, >80%, >85%, >90%, >95%, >98%, >99%) sequence identity with SEQ ID NO: 2; and (b) a polypeptide comprising an amino acid sequence having less than 100% and greater than 30% (e.g., >30%, >40%, >45%, >50%, >55%, >60%, >65%, >70%, >75%, >80%, >85%, >90%, >95%, >98%, >99%) sequence identity with SEQ ID NO: 440, wherein the bioluminescent complex exhibits detectable bioluminescence in the presence of substrate.

In various embodiments, bioluminescent complexes are provided that comprise: (a) a first amino acid sequence comprising an internal tag sequence that is not a fragment of a preexisting protein; and (b) a second amino acid sequence comprising an amino acid sequence that is not a fragment of a preexisting protein, wherein the bioluminescent complex exhibits detectable bioluminescence when the first amino acid sequence and the second amino acid sequence are associated.

In some embodiments, interacting polypeptides are provided, wherein the first polypeptide comprises an internal tag (e.g., an amino acid sequence inserted at a position within its sequence (e.g., not at the N- or C-terminus)), and wherein the second polypeptide comprises a structural complement tag (e.g., an internally- or terminally-located amino acid sequence that is structurally complementary to the internal tag). Upon interaction of the first and second polypeptides, the internal tag and the structural complement tag associate to form a bioluminescent complex. In some embodiments, interaction of the interacting polypeptides is assessed based on the bioluminescence of the bioluminescent complex. In certain embodiments, interactions (e.g., non-covalent interactions (e.g., hydrogen bonds, ionic bonds, van der Waals forces, hydrophobic interactions, etc.), covalent interactions (e.g., disulfide bonds), etc.) between the internal tag and the structural complement tag do not result in significant bioluminescent complex formation in the absence of the interacting polypeptides. In some embodiments, such a system exists (e.g., is expressed) within a cell.

In some embodiments provided herein are bioluminescent complexes comprising: (a) a first substantially non-luminescent element inserted within a polypeptide sequence; and (b) a second substantially non-luminescent element (e.g., free, attached to a polypeptide (e.g., internally or terminally) attached to a molecular entity (e.g., small molecule, etc.), etc.) wherein each non-luminescent element is not a fragment of a preexisting protein.

Various embodiments described herein provide methods of detecting an interaction between a first amino acid sequence and a second amino acid sequence comprising, for example, the steps of: (a) inserting an internal tag within the first amino acid sequence and attaching a complement sequence (e.g., internally or terminally) to the second amino acid sequence, wherein the internal tag and complement sequences are not fragments of a preexisting protein, wherein a complex of the internal tag and the complement sequence emits a detectable bioluminescent signal (e.g., substantially increased bioluminescence relative to the internal tag and the complement sequence separately), wherein the interactions (e.g., non-covalent) between the internal tag and complementary sequence are insufficient to form, or only weakly form, a complex in the absence of additional stabilizing and/or aggregating conditions, and wherein an interaction between the first amino acid sequence and the second amino acid sequence provides the additional stabilizing and/or aggregating forces to produce a complex of the internal tag and the complement sequence; (b) placing the tagged first and second amino acid sequences of step (a) in conditions to allow for interactions between the first amino acid sequence and the second amino acid sequence to occur; and (c) detecting the bioluminescent signal emitted by the complex of the internal tag and complement sequence in the presence of appropriate substrate, wherein detection of the bioluminescent signal indicates an interaction between the first amino acid sequence and the second amino acid sequence. In some embodiments, the first amino acid sequence and the internal tag comprise an internal fusion. In some embodiments, the second amino acid sequence and the complement sequence comprise an internal fusion or a traditional fusion. In some embodiments, the first internal fusion protein (e.g., comprising an internal tag) and the second fusion protein (e.g., comprising a complement sequence) further comprise linkers between the fused elements. In certain embodiments, the fusion proteins are expressed from nucleic acids encoding said fusion proteins. In some embodiments, a single vector comprises both fusion proteins. In other embodiments, first and second fusion proteins are expressed from separate vectors.

In some embodiments provided herein are polypeptides comprising an N-terminal segment, a C-terminal segment, and an internal tag, wherein the internal tag comprises an amino acid sequence having less than 100% and greater than 30% sequence identity with SEQ ID NO: 2 inserted within a protein of interest; wherein a detectable bioluminescent signal is produced in the presence of a coelenterazine substrate when the internal tag contacts a polypeptide of SEQ ID NO: 440. In some embodiments, both the N-terminal segment and the C-terminal segment are at least 20 amino acids in length. In some embodiments, the N-terminal segment and/or the C-terminal segment are at least 50 amino acids in length. In some embodiments, the internal tag exhibits enhancement of one or more traits compared to a peptide of SEQ ID NO: 2, wherein the traits are selected from: affinity for the polypeptide of SEQ ID NO: 440, expression, intracellular solubility, intracellular stability, and bioluminescent activity when combined with the polypeptide of SEQ ID NO: 440. In some embodiments, the internal tag is selected from the peptides of Table 1. In some embodiments, the N-terminal segment and the C-terminal segment, if directly linked in the absence of the internal tag, comprise the sequence of a first protein of interest. In some embodiments, a nucleic acid is provided comprising a sequence coding for the internally tagged polypeptide. In some embodiments, a bioluminescent complex is provided comprising: (a) the internally tagged polypeptide; and (b) a second polypeptide comprising a complement polypeptide having less than 100% and greater than 30% sequence identity with SEQ ID NO: 440. In some embodiments, the internal tag and the complement polypeptide have low affinity for each other. In some embodiments, the second polypeptide is a fusion with a second protein of interest. In some embodiments, the fusion is an internal fusion or a traditional fusion. In some embodiments, the second protein of interest has an affinity for all or a portion of the N-terminal segment and/or the C-terminal segment. In some embodiments, the affinity may be altered by a structural modification to the first or second protein (e.g., a post-translational modification), or both, or by interaction with a third molecule (e.g., a drug, a nucleic acid, a protein, etc.). In some embodiments, the second polypeptide is linked to a molecule of interest. In some embodiments, all or a portion of the N-terminal segment and/or the C-terminal segment has an affinity for the molecule of interest. In some embodiments, a bioluminescent complex further comprises a coelenterazine substrate (e.g., furimazine). In some embodiments, the internal tag and the complement polypeptide have high affinity for each other. In some embodiments, the second polypeptide is not a fusion polypeptide or linked to a molecule of interest. In some embodiments, the complement polypeptide is selected from the peptides of Table 2.

In some embodiments provided herein are polypeptides comprising an N-terminal segment, a C-terminal segment, and an internal tag, wherein the internal tag comprises an amino acid sequence having less than 100% and greater than 30% sequence identity with SEQ ID NO: 440 inserted within a protein of interest; wherein a detectable bioluminescent signal is produced in the presence of a substrate when the detection peptide contacts a polypeptide of SEQ ID NO: 2. In some embodiments, both the N-terminal segment and the C-terminal segment are at least 20 amino acids in length. In some embodiments, the N-terminal segment and/or the C-terminal segment are at least 50 amino acids in length. In some embodiments, the internal tag exhibits enhancement of one or more traits compared to a peptide of SEQ ID NO: 440, wherein the traits are selected from: affinity for the polypeptide of SEQ ID NO: 2, expression, intracellular solubility, intracellular stability, and bioluminescent activity when combined with the polypeptide of SEQ ID NO: 2. In some embodiments, the internal tag is selected from the peptides of Table 2. In some embodiments, the N-terminal segment and the C-terminal segment, if directly linked in the absence of the internal tag, comprise the sequence of a first protein of interest. In some embodiments, a nucleic acid is provided comprising a sequence coding for the internally tagged polypeptide. In some embodiments, a bioluminescent complex is provided comprising: (a) the internally tagged polypeptide; and (b) a complement peptide having less than 100% and greater than 30% sequence identity with SEQ ID NO: 2. In some embodiments, the internal tag and the complement peptide have low affinity for each other. In some embodiments, the complement peptide is a fusion with a second protein of interest. In some embodiments, the fusion is an internal fusion or a traditional fusion. In some embodiments, the second protein of interest has an affinity for all or a portion of the N-terminal segment and/or the C-terminal segment. In some embodiments, the affinity may be altered by a structural modification to the first or second protein (e.g., a post-translational modification), or both, or by interaction with a third molecule (e.g., a drug, a nucleic acid, a protein, etc.). In some embodiments, the complement peptide is linked to a molecule of interest. In some embodiments, all or a portion of the N-terminal segment and/or the C-terminal segment has high affinity for the molecule of interest. In some embodiments, the bioluminescent complex further comprises a coelenterazine substrate. In some embodiments, the internal tag and the complement peptide have high affinity for each other. In some embodiments, the complement peptide is selected from the peptides of Table 1. In some embodiments, the complement peptide is not a fusion polypeptide or linked to a molecule of interest.

In some embodiments provided herein are methods of detecting an interaction between a first amino acid sequence and a second amino acid sequence comprising: (a) creating an internal fusion by inserting an internal tag into the first amino acid sequence, such that said internal tag is neither at the N-terminus not the C-terminus of the first amino acid sequence, wherein the internal tag has less than 100% and greater than 30% sequence identity with SEQ ID NO: 2, and wherein a detectable bioluminescent signal is produced in the presence of a coelenterazine substrate when the internal tag contacts a polypeptide of SEQ ID NO: 440; (b) creating a second fusion of the second amino acid sequence and a complement polypeptide, wherein the complement polypeptide has less than 100% and greater than 30% sequence identity with SEQ ID NO: 440, and wherein a detectable bioluminescent signal is produced in the presence of a coelenterazine substrate when the complement polypeptide contacts a peptide of SEQ ID NO: 2; (c) placing the internal fusion, second fusion, and a coelenterazine substrate in conditions that allow for a possible interaction to occur between the first amino acid sequence and the second amino acid sequence; and (d) detecting, if present, a bioluminescent signal emitted, wherein detection of the bioluminescent signal indicates an interaction between the first amino acid sequence and the second amino acid sequence. In some embodiments, the interaction is detected in living cells or organisms by detecting the bioluminescence signal emitted by the cells or organism. In some embodiments, an alteration in the interaction resulting from an alteration of the environment of the cells is detected by detecting a difference in the emitted bioluminescent signal relative to control cells absent the altered environment. In some embodiments, the altered environment is the result of adding or removing a molecule from the culture medium (e.g., a drug). In some embodiments, the second fusion is an internal fusion or a traditional fusion. In some embodiments, the internal fusion is expressed from a first nucleic acid sequence coding for the first amino acid sequence and the internal tag, and the second fusion is expressed from a second nucleic acid sequence coding for the second amino acid sequence and the complement polypeptide. In some embodiments, a single vector comprises the first nucleic acid sequence and the second nucleic acid sequence. In some embodiments, the first nucleic acid sequence and the second nucleic acid sequence are on separate vectors. In some embodiments, steps (a) and (b) comprise expressing the internal fusion and second fusion within a cell.

In some embodiments, provided herein are methods of detecting an interaction between a first amino acid sequence and a second amino acid sequence comprising: (a) creating an internal fusion by inserting an internal tag into the first amino acid sequence, such that said internal tag is neither at the N-terminus not the C-terminus of the first amino acid sequence, wherein the internal tag has less than 100% and greater than 30% sequence identity with SEQ ID NO: 440, and wherein a detectable bioluminescent signal is produced in the presence of a coelenterazine substrate when the internal tag contacts a peptide of SEQ ID NO: 2; (b) creating a second fusion of the second amino acid sequence and a complement peptide, wherein the complement peptide has less than 100% and greater than 30% sequence identity with SEQ ID NO: 2, and wherein a detectable bioluminescent signal is produced in the presence of a coelenterazine substrate when the complement peptide contacts a polypeptide of SEQ ID NO: 2; (c) placing the internal fusion, second fusion, and a coelenterazine substrate in conditions that allow for a possible interaction to occur between the first amino acid sequence and the second amino acid sequence; and (d) detecting, if present, a bioluminescent signal emitted, wherein detection of the bioluminescent signal indicates an interaction between the first amino acid sequence and the second amino acid sequence. In some embodiments, the second fusion is an internal fusion or a traditional fusion. In some embodiments, the internal fusion is expressed from a first nucleic acid sequence coding for the first amino acid sequence and the internal tag, and the second fusion is expressed from a second nucleic acid sequence coding for the second amino acid sequence and the complement peptide. In some embodiments, a single vector comprises the first nucleic acid sequence and the second nucleic acid sequence. In some embodiments, the first nucleic acid sequence and the second nucleic acid sequence are on separate vectors. In some embodiments, steps (a) and (b) comprise expressing the internal fusion and second fusion within a cell.

In some embodiments provided herein are methods of detecting a target polypeptide in a sample comprising: (a) creating an internal fusion by inserting an internal tag into the target polypeptide, such that said internal tag is neither at the N-terminus not the C-terminus of the target polypeptide, wherein the internal tag has less than 100% and greater than 30% sequence identity with SEQ ID NO: 440, and wherein a detectable bioluminescent signal is produced in the presence of a coelenterazine substrate when the internal tag contacts a peptide of SEQ ID NO: 2; (b) adding to said sample: (i) a complement peptide that has less than 100% and greater than 30% sequence identity with SEQ ID NO: 2, and (ii) a coelenterazine substrate; and (c) detecting, if present, a bioluminescent signal emitted, wherein detection of the bioluminescent signal indicates the presence of the target polypeptide in the sample. In some embodiments, the sample comprises a cell. In some embodiments, step (a) comprises expressing said internal fusion in said cell. In some embodiments, step (b)(i) comprises said complement peptide in said cell.

In some embodiments provided herein are methods of detecting a target polypeptide in a sample comprising: (a) creating an internal fusion by inserting an internal tag into the target polypeptide, such that said internal tag is neither at the N-terminus not the C-terminus of the target polypeptide, wherein the internal tag has less than 100% and greater than 30% sequence identity with SEQ ID NO: 2, and wherein a detectable bioluminescent signal is produced in the presence of a coelenterazine substrate when the internal tag contacts a peptide of SEQ ID NO: 440; (b) adding to said sample: (i) a complement polypeptide that has less than 100% and greater than 30% sequence identity with SEQ ID NO: 440, and (ii) a coelenterazine substrate; and (c) detecting, if present, a bioluminescent signal emitted, wherein detection of the bioluminescent signal indicates the presence of the target polypeptide in the sample. In some embodiments, the sample comprises a cell. In some embodiments, step (a) comprises expressing said internal fusion in said cell. In some embodiments, step (b)(i) comprises said complement polypeptide in said cell.

In some embodiments provided herein are detection reagents comprising: (a) a complement polypeptide comprising an amino acid sequence having less than 100% and greater than 30% sequence identity with SEQ ID NO: 440, wherein a detectable bioluminescent signal is produced, in the presence of a substrate, when the polypeptide contacts a peptide of SEQ ID NO: 2, and (b) a substrate for a bioluminescent complex produced by said polypeptide and a peptide of SEQ ID NO: 2.

In some embodiments provided herein are detection reagents comprising: (a) a complement peptide comprising an amino acid sequence having less than 100% and greater than 30% sequence identity with SEQ ID NO: 2, wherein a detectable bioluminescent signal is produced, in the presence of a substrate, when the peptide contacts a polypeptide of SEQ ID NO: 440, and (b) a substrate for a bioluminescent complex produced by said peptide and a polypeptide of SEQ ID NO: 440.

In certain embodiments, an internal tag and/or structural complement comprises or consists of an amino acid having 100% sequence identity with SEQ ID NO: 2 or SEQ ID NO: 440. In some embodiments, such internal tags and structural complements find use in any embodiments described herein and with any other peptide or polypeptide sequences described herein.

In some embodiments provided herein are methods of detecting alteration of an interaction between a first amino acid sequence and a second amino acid sequence by an agent comprising: (a) creating an internal fusion by inserting an internal tag into the first amino acid sequence, such that said internal tag is neither at the N-terminus not the C-terminus of the first amino acid sequence, wherein the internal tag has less than 100% and greater than 30% sequence identity with SEQ ID NO: 2, and wherein a detectable bioluminescent signal is produced in the presence of a coelenterazine substrate when the internal tag contacts a polypeptide of SEQ ID NO: 440; (b) creating a second fusion of the second amino acid sequence and a complement polypeptide, wherein the complement polypeptide has less than 100% and greater than 30% sequence identity with SEQ ID NO: 440, and wherein a detectable bioluminescent signal is produced in the presence of a coelenterazine substrate when the complement polypeptide contacts a peptide of SEQ ID NO: 2; (c) placing the internal fusion, second fusion, and a coelenterazine substrate in conditions that allow for a possible interaction to occur between the first amino acid sequence and the second amino acid sequence; (d) detecting, if present, a bioluminescent signal emitted; (e) adding the agent to the internal fusion, second fusion, and a coelenterazine substrate; (f) detecting, if present, a bioluminescent signal emitted; and (g) comparing the bioluminescent signals of steps (d) and (f), wherein change in bioluminescent signal from step (d) to step (f) indicates alteration of the interaction between the first amino acid sequence and the second amino acid sequence by the agent. In some embodiments, steps (a) and (b) comprise expressing the internal fusion and second fusion within a cell. In some embodiments, the agent is a peptide or small molecule. In some embodiments, the agent is an inhibitor of the interaction, wherein reduced interaction is detected by a decrease in the bioluminescent signal. In some embodiments, the agent is an activator of the interaction, wherein increased interaction is detected by an increase in the bioluminescent signal.

In some embodiments, provided herein are methods of detecting alteration of an interaction between a first amino acid sequence and a second amino acid sequence by an agent comprising: (a) creating an internal fusion by inserting an internal tag into the first amino acid sequence, such that said internal tag is neither at the N-terminus not the C-terminus of the first amino acid sequence, wherein the internal tag has less than 100% and greater than 30% sequence identity with SEQ ID NO: 440, and wherein a detectable bioluminescent signal is produced in the presence of a coelenterazine substrate when the internal tag contacts a peptide of SEQ ID NO: 2; (b) creating a second fusion of the second amino acid sequence and a complement polypeptide, wherein the complement peptide has less than 100% and greater than 30% sequence identity with SEQ ID NO: 2, and wherein a detectable bioluminescent signal is produced in the presence of a coelenterazine substrate when the complement polypeptide contacts a polypeptide of SEQ ID NO: 440; (c) placing the internal fusion, second fusion, and a coelenterazine substrate in conditions that allow for a possible interaction to occur between the first amino acid sequence and the second amino acid sequence; (d) detecting, if present, a bioluminescent signal emitted; (e) adding the agent to the internal fusion, second fusion, and a coelenterazine substrate; (f) detecting, if present, a bioluminescent signal emitted; and (g) comparing the bioluminescent signals of steps (d) and (f), wherein change in bioluminescent signal from step (d) to step (f) indicates alteration of the interaction between the first amino acid sequence and the second amino acid sequence by the agent. In some embodiments, steps (a) and (b) comprise expressing the internal fusion and second fusion within a cell. In some embodiments, the agent is a peptide or small molecule. In some embodiments, the agent is an inhibitor of the interaction, wherein reduced interaction is detected by a decrease in the bioluminescent signal. In some embodiments, the agent is an activator of the interaction, wherein increased interaction is detected by an increase in the bioluminescent signal.

In some embodiments provided herein are methods of detecting an alteration in the structural conformation of a first amino acid sequence by an agent comprising: (a) creating an internal fusion by inserting an internal tag into the first amino acid sequence, such that said internal tag is neither at the N-terminus not the C-terminus of the first amino acid sequence, wherein the internal tag has less than 100% and greater than 30% sequence identity with SEQ ID NO: 2, wherein a detectable bioluminescent signal is produced in the presence of a coelenterazine substrate when the internal tag contacts a polypeptide of SEQ ID NO: 440, wherein a first structural conformation of the first amino acid sequence alters access to the internal tag relative to a second structural conformation of the first amino acid sequence; (b) placing the internal fusion and either (i) a complement polypeptide having less than 100% and greater than 30% sequence identity with SEQ ID NO: 440 or (ii) a second fusion of a second amino acid sequence and the complement polypeptide in the presence of a coelenterazine substrate; (c) detecting, if present, a bioluminescent signal emitted; (d) adding the agent to the internal fusion, second fusion, and a coelenterazine substrate; (e) detecting, if present, a bioluminescent signal emitted; and (f) comparing the bioluminescent signals of steps (c) and (e), wherein change in bioluminescent signal from step (c) to step (e) indicates alteration of the conformation of the first amino acid sequence by the agent. In some embodiments, inducing a conformational change is selected from: adding a protease that cleave a portion of the first amino acid sequence, addition an agent that binds to the first amino acid sequence, and altering the assay conditions.

In some embodiments provided herein are methods of detecting an alteration in the structural conformation of a first amino acid sequence by an agent comprising (a) creating an internal fusion by inserting an internal tag into the first amino acid sequence, such that said internal tag is neither at the N-terminus not the C-terminus of the first amino acid sequence, wherein the internal tag has less than 100% and greater than 30% sequence identity with SEQ ID NO: 440, wherein a detectable bioluminescent signal is produced in the presence of a coelenterazine substrate when the internal tag contacts a peptide of SEQ ID NO: 2, wherein a first structural conformation of the first amino acid sequence alters access to the internal tag relative to a second structural conformation of the first amino acid sequence; (b) placing the internal fusion and either (i) a complement peptide having less than 100% and greater than 30% sequence identity with SEQ ID NO: 2 or (ii) a second fusion of a second amino acid sequence and the complement peptide in the presence of a coelenterazine substrate; (c) detecting, if present, a bioluminescent signal emitted; (d) adding the agent to the internal fusion, second fusion, and a coelenterazine substrate; (e) detecting, if present, a bioluminescent signal emitted; and (f) comparing the bioluminescent signals of steps (c) and (e), wherein change in bioluminescent signal from step (c) to step (e) indicates alteration of the conformation of the first amino acid sequence by the agent. In some embodiments, inducing a conformational change is selected from: adding a protease that cleaves a portion of the first amino acid sequence, adding an agent that binds to the first amino acid sequence, and altering the assay conditions.

In some embodiments provided herein are polypeptides comprising an N-terminal segment, a C-terminal segment, and two or more internal tags, wherein the internal tags comprise amino acid sequences having less than 100% and greater than 30% sequence identity with SEQ ID NO: 2 inserted within a protein of interest; wherein a detectable bioluminescent signal is produced in the presence of a coelenterazine substrate when one or more of the internal tags contact a polypeptide of SEQ ID NO: 440. In some embodiments, the two or more internal tags are two internal tags (e.g., tandem tags). In some embodiments, the two or more internal tags are directly connected to one another. In some embodiments, the two or more internal tags are separated by one or more linkers (e.g., peptide linker). In some embodiments, the two or more internal tags are inserted at a single location within the protein or polypeptide of interest. In some embodiments, the two or more internal tags are inserted at two or more locations within the protein or polypeptide of interest. In some embodiments, the two or more internal tags comprise identical amino acid sequences. In some embodiments, the two or more or the two or more internal tags comprise non-identical amino acid sequences. In some embodiments, the two or more internal tags have amino acid substitutions that may or may not have an impact on affinity with a complement sequence, but that change the overall charge of the internal tag or tandem tags to be either more charged or closer to neutral.

DEFINITIONS

Figure 1:
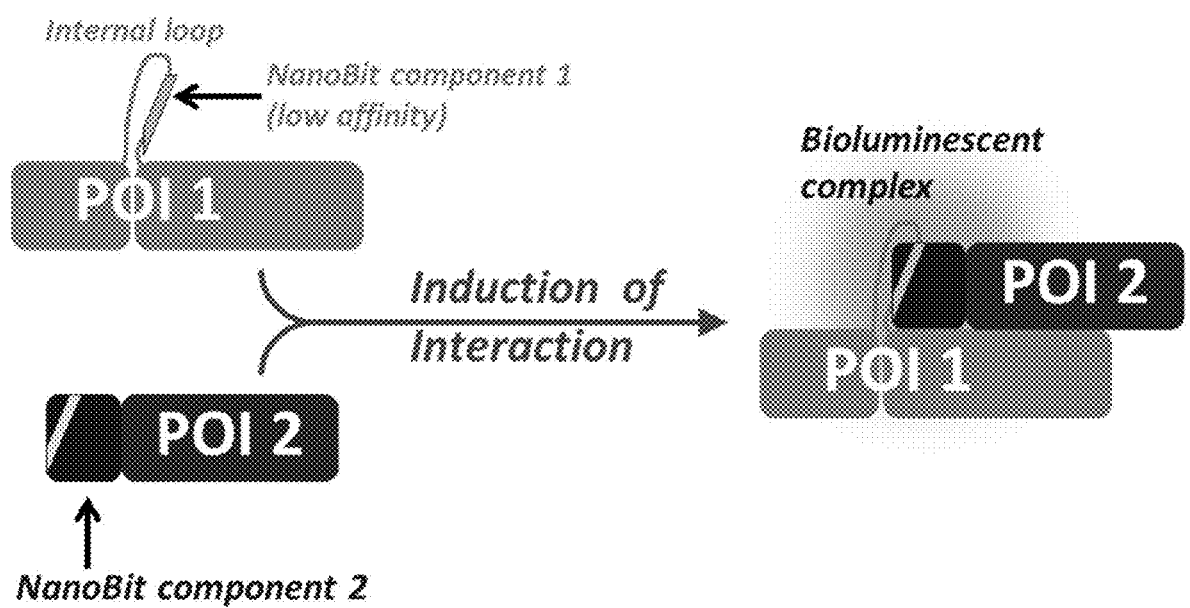
FIG. 1 shows a schematic depiction of an exemplary embodiment in which an internal tag (e.g., NLpep or NLpoly) is inserted into a first protein of interest (POI 1) as an internal loop, and a complement sequence (e.g., NLpep or NLpoly) is fused terminally to a second protein of interest (POI 2). The internal tag and complement sequence have low affinity for each other, such that they are ineffective in forming a complex (e.g., produce an undetectable or negligible amount of complex) in the absence of external forces. Although the internal tag and complement sequence are separately substantially non-luminescent, upon interaction of POI 1 and POI 2, a bioluminescent complex is formed between the internal tag and complement sequence.

As used herein, the term "internal tag" refers to a peptide or polypeptide sequence that is inserted within another polypeptide or protein (e.g., not at the N- or C-terminus). The internal tag may provide one or more characteristics of detection, isolation, localization, association, etc. to the peptide or polypeptide sequence within which it is inserted. An internal tag may either be directly connected to the N- and C-terminal portions of the polypeptide or protein or may be connected by one or more linkers. In some embodiments, the linkers themselves may provide a functionality.

As used herein, the term "substantially" means that the recited characteristic, parameter, and/or value need not be achieved exactly, but that deviations or variations, including for example, tolerances, measurement error, measurement accuracy limitations and other factors known to those of skill in the art, may occur in amounts that do not preclude the effect the characteristic was intended to provide. A characteristic or feature that is substantially absent (e.g., substantially non-luminescent) may be one that is within the noise, beneath background, or below the detection capabilities of the assay being used.

As used herein, the term "bioluminescence" refers to production and emission of light by a chemical reaction catalyzed by, or enabled by, an enzyme, protein, protein complex, or other biomolecule (e.g., bioluminescent complex). In typical embodiments, a substrate for a bioluminescent entity (e.g., bioluminescent protein or bioluminescent complex) is converted into a high-energy reaction product by the bioluminescent entity; the reaction product subsequently emits light as it converts to a more stable form.

As used herein the term "complementary" refers to the characteristic of two or more structural elements (e.g., peptide, polypeptide, nucleic acid, small molecule, etc.) of being able to hybridize, dimerize, or otherwise form a complex with each other. For example, a "complementary peptide and polypeptide" are capable of coming together to form a complex. Complementary elements may require assistance to form a stable complex (e.g., from interaction elements), for example, to place the elements in the proper conformation for complementarity, to co-localize complementary elements, to lower interaction energy for complementary, etc. In some embodiments, a "complement sequence", a "complement", or a "structural complement" is an amino acid sequence that is the structural complement of another sequence (e.g., of an internal tag).

As used herein, the term "complex" refers to an assemblage or aggregate of molecules (e.g., peptides, polypeptides, etc.) in direct and/or indirect contact with one another. In one aspect, "contact," or more particularly, "direct contact" means two or more molecules are close enough so that attractive noncovalent interactions between the molecules, such as Van der Waal forces, hydrogen bonding, ionic and hydrophobic interactions, and the like, influence the interaction of the molecules. As used herein, the term "complex", unless described as otherwise, refers to the assemblage of two or more molecules (e.g., peptides, polypeptides or a combination thereof).

As used herein, the term "non-luminescent" refers to an entity (e.g., peptide, polypeptide, complex, protein, etc.) that exhibits the characteristic of not emitting energy as light in the visible spectrum (e.g., in the presence or absence of a substrate). An entity may be referred to as non-luminescent if it does not exhibit detectable luminescence in a given assay. As used herein, the term "non-luminescent" is synonymous with the term "substantially non-luminescent." An entity is "non-luminescent" if any light emission is sufficiently minimal so as not to interfere with the intended purpose for a particular assay.

As used herein, the terms "non-luminescent peptide" (NLpep) and "non-luminescent polypeptide" (NLpoly) refer to peptides and polypeptides (e.g., an internal tag, a complement sequence, etc.) that exhibit substantially no luminescence (e.g., in the presence or absence of a substrate), or an amount that is virtually undetectable (e.g., beneath the noise) under standard conditions (e.g., physiological conditions, assay conditions, etc.) and with typical instrumentation (e.g., luminometer, etc.). In some embodiments, such non-luminescent peptides and polypeptides assemble, according to the criteria described herein, to form a bioluminescent complex. As used herein, a "non-luminescent element" is a non-luminescent peptide or non-luminescent polypeptide. The term "bioluminescent complex" refers to the assembled complex of two or more non-luminescent peptides and/or non-luminescent polypeptides. The bioluminescent complex catalyzes or enables the conversion of a substrate for the bioluminescent complex into a high-energy reaction product; the reaction product subsequently emits light as it converts to a more stable form. When uncomplexed, two non-luminescent elements that form a bioluminescent complex may be referred to as a "non-luminescent pair." If a bioluminescent complex is formed by three or more non-luminescent peptides and/or non-luminescent polypeptides, the uncomplexed constituents of the bioluminescent complex may be referred to as a "non-luminescent group." As used herein, the term "non-luminescent complex" refers to a complex of two or more elements (e.g., peptides, polypeptides, etc.) that does not does not substantially catalyze the conversion of a substrate for the bioluminescent complex into a high-energy reaction product. In some embodiments, a "non-luminescent complex" requires an additional non-luminescent element (e.g., a third element) to form a luminescent complex.

As used herein, the term "interaction element" refers to a moiety that assists in bringing together a pair of non-luminescent elements (e.g., an internal tag and a complement sequence) or a non-luminescent group (e.g., an internal tag and a complement sequence) to form a bioluminescent complex. In a typical embodiment, a pair of interaction elements (a.k.a. "interaction pair") is attached to a pair of non-luminescent elements (e.g., non-luminescent peptide/polypeptide pair), and the attractive interaction between the two interaction elements facilitates formation of the bioluminescent complex; although the present invention is not limited to such a mechanism, and an understanding of the mechanism is not required to practice the invention. Interaction elements may facilitate formation of the bioluminescent complex by any suitable mechanism (e.g., bringing non-luminescent pair/group into close proximity, placing a non-luminescent pair/group in proper conformation for interaction, reducing activation energy for complex formation, combinations thereof, etc.). An interaction element may be a protein, polypeptide, peptide, small molecule, cofactor, nucleic acid, lipid, carbohydrate, antibody, polymer, particle, etc. An interaction pair may be made of two of the same interaction elements (i.e. homopair) or two different interaction elements (i.e. heteropair). In the case of a heteropair, the interaction elements may be the same type of moiety (e.g., polypeptides) or may be two different types of moieties (e.g., polypeptide and small molecule). In some embodiments, in which complex formation by the interaction pair is studied, an interaction pair may be referred to as a "target pair" or a "pair of interest," and the individual interaction elements are referred to as "target elements" (e.g., "target peptide," "target polypeptide," etc.) or "elements of interest" (e.g., "peptide of interest," "polypeptide or interest," etc.).

As used herein, the term "preexisting protein" refers to an amino acid sequence that was in physical existence prior to a certain event or date. A "peptide that is not a fragment of a preexisting protein" is a short amino acid chain that is not a fragment or sub-sequence of a protein (e.g., synthetic or naturally-occurring) that was in physical existence prior to the design and/or synthesis of the peptide.

As used herein, the term "fragment" refers to a peptide or polypeptide that results from dissection or "fragmentation" of a larger whole entity (e.g., protein, polypeptide, enzyme, etc.), or a peptide or polypeptide prepared to have the same sequence as such. Therefore, a fragment is a subsequence of the whole entity (e.g., protein, polypeptide, enzyme, etc.) from which it is made and/or designed. A peptide or polypeptide that is not a subsequence of a preexisting whole protein is not a fragment (e.g., not a fragment of a preexisting protein). A peptide or polypeptide that is "not a fragment of a preexisting bioluminescent protein" is an amino acid chain that is not a subsequence of a protein (e.g., natural of synthetic) that: (1) was in physical existence prior to design and/or synthesis of the peptide or polypeptide, and (2) exhibits substantial bioluminescent activity.

As used herein, the term "subsequence" refers to a peptide or polypeptide that has 100% sequence identify with another, larger peptide or polypeptide. The subsequence is a perfect sequence match for a portion of the larger amino acid chain.

As used herein, the term "sequence identity" refers to the degree two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) have similar polymer sequences. For example, similar amino acids are those that share the same biophysical characteristics and can be grouped into the families, e.g., acidic (e.g., aspartate, glutamate), basic (e.g., lysine, arginine, histidine), non-polar (e.g., alanine, valine, leucine, isoleucine, proline, phenylalanine, methionine, tryptophan) and uncharged polar (e.g., glycine, asparagine, glutamine, cysteine, serine, threonine, tyrosine). The "percent sequence identity" (or "percent sequence similarity") is calculated by: (1) comparing two optimally aligned sequences over a window of comparison (e.g., the length of the longer sequence, the length of the shorter sequence, a specified window), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

As used herein, the term "physiological conditions" encompasses any conditions compatible with living cells, e.g., predominantly aqueous conditions of a temperature, pH, salinity, chemical makeup, etc. that are compatible with living cells.

As used herein, the term "sample" is used in its broadest sense. In one sense, it is meant to include a specimen or culture obtained from any source as well as biological and environmental samples. Biological samples may be obtained from animals (including humans) and encompass fluids, solids, tissues, and gases. Biological samples include blood products, such as plasma, serum and the like. Sample may also refer to cell lysates or purified forms of the peptides and/or polypeptides described herein. Cell lysates may include cells that have been lysed with a lysing agent or lysates such as rabbit reticulocyte or wheat germ lysates. Sample may also include cell-free expression systems. Environmental samples include environmental material such as surface matter, soil, water, and industrial samples. Such examples are not however to be construed as limiting the sample types applicable to the present invention.

As used herein, unless otherwise specified, the terms "peptide" and "polypeptide" refer to polymer compounds of two or more amino acids joined through the main chain by peptide amide bonds (—C(O)NH—). The term "peptide" typically refers to short amino acid polymers (e.g., chains having fewer than 25 amino acids), whereas the term "polypeptide" typically refers to longer amino acid polymers (e.g., chains having more than 25 amino acids).

As used herein, the terms "fusion", "fusion polypeptide", and "fusion protein" refer to a chimeric protein containing a first protein or polypeptide of interest (e.g., target sequence, etc.) joined to a second different peptide, polypeptide, or protein (e.g., detectable sequence, isolatable sequence, tag, etc.). The term "internal fusion", as used herein, refers to a fusion in which the second peptide, polypeptide, or protein is inserted at a position within the sequence of the first (e.g., not at the N- or C-terminus). The term "traditional fusion" refers to a fusion in which the first polypeptide or protein and the second peptide, polypeptide, or protein are fused end to end (e.g., C-terminus to N-terminus or N-terminus to C-terminus).

As used herein, the terms "coelenterazine" or "coelenterazine substrate" refer to naturally-occurring ("native") coelenterazine. As used herein, the terms "a coelenterazine" or "a coelenterazine substrate" refers to native coelenterazine as well as synthetic, e.g., derivative or variant, and natural analogs thereof, including furimazine, coelenterazine-n, coelenterazine-f, coelenterazine-h, coelenterazine-hcp, coelenterazine-cp, coelenterazine-c, coelenterazine-e, coelenterazine-fcp, bis-deoxycoelenterazine ("coelenterazine-hh"), coelenterazine-i, coelenterazine-icp, coelenterazine-v, and 2-methyl coelenterazine, in addition to those disclosed in WO 2003/040100; U.S. application Ser. No. 12/056,073 (paragraph [0086]); and U.S. Pat. No. 8,669,103; the disclosures of which are incorporated by reference herein in their entireties.

As used herein, the term "low affinity" describes an intermolecular interaction between two entities (e.g., protein-protein) that is too weak to result in significant complex formation between the entities, except at concentrations substantially higher (e.g., 2-fold, 5-fold, 10-fold, 100-fold, 1000-fold, or more) than physiologic or assay conditions.

As used herein, the term "high affinity" describes an intermolecular interaction between two entities that is of sufficient strength to produce detectable complex formation under physiologic or assay conditions.

DETAILED DESCRIPTION

Tagging of proteins with reporters is commonly used to analyze protein function and behavior. In general, genetic fusions are generated using either the C- or N-terminus of the protein of interest. However, in certain cases, both termini are relevant to function of the protein of interest, and therefore cannot be modified without altering the physiological function of the protein. Embodiments described herein enable, for example, the analysis of protein-protein interactions without the need of modification of either the N- or C-terminus. Embodiments further enable detection and/or localization (e.g., cellular or subcellular localization) of a protein without the need of modification of either the N- or C-terminus. Various proteins undergo modifications that lead to changes in configuration; using an internal peptide/polypeptide tag that is accessible for structural complementation based on the configuration of the host protein enables the generation of biosensors using full length proteins. Therefore, provided herein are substantially non-luminescent peptide/polypeptide tags that are inserted internally within a protein of interest. Interaction of the internally-inserted tag with a complement polypeptide/peptide that is also substantially non-luminescent results in the formation a bioluminescent reporter complex.

Provided herein are compositions and methods for the assembly of a bioluminescent complex from an internal tag (e.g., peptide or polypeptide) of a protein or polypeptide and a structural complement thereof (e.g., free or in a fusion (e.g., internal or terminal)). In some embodiments, the internal tag and/or structural complement are not fragments of a preexisting protein (e.g., are not complementary subsequences of a known polypeptide sequence). In particular, bioluminescent activity is conferred upon a substantially non-luminescent internal tag of a protein/polypeptide via structural complementation with a substantially non-luminescent peptide structural complement sequence of the internal tag.

In some embodiments provided herein are substantially non-luminescent internal tags and structural complements thereof for use in detecting the presence of proteins/polypeptides of interest, and for monitoring molecular interactions (e.g., protein-protein, protein-DNA, protein-RNA interactions, protein-small molecule, etc.). Also provided herein are complementary panels of interchangeable internal tags and structural complement sequences (e.g., peptides and polypeptides) that have variable affinities and luminescence upon formation of the various bioluminescent complexes (e.g., a high-affinity/high-luminescence pair, a moderate-affinity/high-luminescence pair, a low-affinity/moderate-luminescence pair, etc.). Utilizing different combinations of internal tags and structural complements provides an adaptable system comprising various pairs ranging from lower to higher affinities, luminescence and other variable characteristics. This adaptability allows the detection/monitoring of proteins of interest and their molecular interactions to be fine-tuned to the specific molecule(s) of interest and expands the range of molecular interactions that can be monitored to include interactions with very high or low affinities. Further provided herein are methods by which internal tags, structural complements, and panels thereof are developed and tested.

In some embodiments, the affinity between the internal tag and the structural complement alone is insufficient to form the active (e.g., bioluminescent) complex and produce the resulting signal (e.g., bioluminescent signal). However, if the structural complement is fused, tethered, attached, etc., to an interaction moiety (e.g., peptide, protein, nucleic acid, small molecule, etc.) that interacts with the internally tagged polypeptide, then that interaction (e.g., complex formation between the polypeptide of interest and the interaction moiety) facilitates formation of the bioluminescent complex. In such embodiments, the signal from the bioluminescent complex in the presence of a substrate serves as an indication for the formation of the complex of the polypeptide of interest and the integration moiety (a.k.a., interaction complex). If an interaction complex is formed, then a bioluminescent complex is formed, and a bioluminescent signal is generated, which can then be detected/measured/monitored (e.g., in the presence of substrate). If an interaction complex fails to form (e.g., due to unfavorable conditions, due to unstable interaction between the interaction elements, due to incompatible interaction elements, etc.), then a stable bioluminescent complex does not form, and a bioluminescent signal is not produced.

In certain embodiments, an internally tagged polypeptide and a second moiety that interacts (e.g., forms a complex) therewith are known as an interaction pair. In some embodiments, an interaction pair comprises two molecules of interest (e.g., proteins of interest). In some embodiments, at least one member of an interaction pair is internally tagged. In some embodiments, both members of an interaction pair are internally tagged (e.g., with structurally complementary internal tags). In some embodiments, one member of an interaction pair is internally tagged and the other is terminally tagged. For example, assays are performed to detect the interaction of a protein of interest and a second molecule of interest (e.g., peptide, protein, nucleic acid, small molecule, etc.) by inserting an internal tag into the protein of interest and tethering (e.g., internal tag, terminal tag, etc.) the molecule of interest to a structural complement of the internal tag. If the protein of interest and the molecule of interest interact (e.g., transiently interact, stably interact, etc.), the internal tag and structural complement are brought into close proximity in a suitable conformation to form an active complex (e.g., a bioluminescent complex) signal is produced/detected (e.g., in the presence of substrate). In the absence of an interaction between the protein of interest and the molecule of interest, the internal tag and structural complement do not interact in a stable enough manner, and a signal is not produced or only weakly produced. Such embodiments find use to study the effect of inhibitors on complex formation, the effect of mutations on complex formation, the effect of conditions (e.g., temperature, pH, etc.) on complex formation, the interaction of a small molecule (e.g., potential therapeutic) with a target molecule, etc.

In some embodiments, an internally-tagged protein of interest is monitored (e.g., detected, localized, etc.) by the formation of an active (e.g., bioluminescent) complex with a free structural complement. In such embodiments, an internal tag and structural complement are selected with sufficiently high affinity for each other such that detectable complex forms when both an internally tagged protein and the free structural complement are present.

Different internal tag and structural complement pairs may require different strength, duration and/or stability of the interaction complex to result in active (e.g., bioluminescent) complex formation. In some embodiments, a stable interaction complex is required to produce a detectable (e.g., bioluminescent) signal. In other embodiments, even a weak or transient interaction complex results in active (e.g., bioluminescent) complex formation. In some embodiments, the strength of an interaction complex is directly proportional to the strength of the resulting (e.g., bioluminescent) signal. Some internal tag and structural complement pairs produce a detectable signal when combined with an interaction pair (e.g., internally-tagged protein of interest and interaction partner) with a high millimolar dissociation constant (e.g., $K_d > 100$ mM). Other internal tag and structural complement pairs require an interaction pair with a low millimolar (e.g., $K_d < 100$ mM), micromolar (e.g., $K_d < 1$ mM), nanomolar (e.g., $K_d < 1$ µM), or even picomolar (e.g., $K_d < 1$ nM) dissociation constant in order to produce a bioluminescent complex with a detectable signal. Still other internal tag and structural complement pairs form an active complex in the absence of any interaction pair.

In some embodiments, one or both of the internal tag and structural complement are not fragments of a pre-existing protein. In some embodiments, one or both of the internal tag and structural complement are not fragments of a pre-existing bioluminescent protein. In some embodiments, neither the internal tag nor the structural complement is a fragment of a pre-existing protein. In some embodiments, neither the internal tag nor the structural complement is a fragment of a pre-existing bioluminescent protein.

In some embodiments, both the internal tag and its structural complement are substantially inactive (e.g., non-luminescent) in isolation. In certain embodiments, when placed in suitable conditions (e.g., physiological conditions), the substantially non-luminescent internal tag and its substantially non-luminescent structural complement interact to form a bioluminescent complex and produce a bioluminescent signal in the presence of substrate. In some embodiments, an internal tag and its structural complement produce a low level of activity (e.g., bioluminescence) in each other's presence, but undergo a significant increase in detectable activity (e.g., bioluminescence) under a particular set of conditions.

In some embodiments, compositions and methods described herein comprise one or more interaction elements. In a typical embodiment, an interaction element is a moiety (e.g., peptide, polypeptide, protein, small molecule, nucleic acid, lipid, carbohydrate, etc.) that is attached to a structural complement of the internally tag, and associates or forms a complex with the internally-tagged protein to facilitate assembly of the complex of the internal tag and its structural complement.

In some embodiments, an interaction pair comprises the internally-tagged protein or polypeptide and any other suitable chemical moiety that interacts with the internally-tagged protein or polypeptide to facilitate assembly of the active complex of the internal tag and its structural complement. An interaction pair may consist of, for example: an internally tagged protein and: a nucleic acid, a polypeptide, a protein, a ligand, a small molecule, an antibody, a lipid, etc. Any molecular entity capable of interacting with the internally tagger protein or polypeptide may find use in some embodiments herein.

In some embodiments, compositions and methods herein provide useful assays (e.g., in vitro, in vivo, in situ, whole animal, etc.) for studying the interactions between a pair of target molecules (e.g., the internally-tagged protein and a (potential) interaction partner).

In some embodiments, the presence of a ligand, substrate, co-factor, etc., is necessary to induce the interaction between the internally-tagged protein and its interaction partner, in order to facilitate formation of the complex (e.g., bioluminescent complex) between the internal tag and the structural complement linked to the interaction partner. In some embodiments, detecting a signal from the bioluminescent complex indicates the presence of the ligand, substrate, co-factor, etc.

In some embodiments, an internal tag and its structural complement are present in a single amino acid chain (e.g., N-(amino acid sequence 1)-(internal tag)-(amino acid sequence 2)-(structural complement)-C, etc.). In some embodiments, folding of the protein of interest results in formation of the active complex (e.g., bioluminescent complex).

In some embodiments, an internally-tagged protein and fusion of an interaction peptide or polypeptide and a structural complement of the internal tag are expressed within the same cells. In such embodiments, an internally-tagged protein and fusion of an interaction peptide or polypeptide and a structural complement of the internal tag are purified and/or isolated from the cells, or the interaction is assayed within the cells. In some embodiments, an internally-tagged protein and fusion of an interaction peptide or polypeptide and a structural complement of the internal tag are stably expressed. In some embodiments, an internally-tagged protein and fusion of an interaction peptide or polypeptide and a structural complement of the internal tag are transiently expressed. In other embodiments, an internally-tagged protein and fusion of an interaction peptide or polypeptide and a structural complement of the internal tag are expressed in separate cells and combined (e.g., following purification and/or isolation) for signal detection. In some embodiments, an internally-tagged protein and fusion of an interaction peptide or polypeptide and a structural complement of the internal tag are expressed in cell lysate (e.g., rabbit reticulocyte lysate) or in a cell-free system.

In certain embodiments, nucleic acids, DNA, RNA, vectors, etc. are provided that encode the peptides, polypeptides, fusion polypeptides, fusion proteins, etc., described herein. Such nucleic acids and vectors may be used for expression, transformation, transfection, injection, etc.

In some embodiments, an internal tag is attached (e.g., on its N-terminus, on its C-terminus, at both ends) to polypeptide sequence by a linker. In some embodiments, structural complement is attached (e.g., on its N-terminus, on its C-terminus, at both ends) to a molecule of interest (e.g., protein of interest) by a linker. In some embodiments, a linker provides a connection and allows a desired amount of space/distance between the elements. In certain embodiments, a linker provides appropriate attachment chemistry between the linked elements. In some embodiments, a linker is any suitable chemical moiety capable of linking, connecting, or tethering two elements (e.g., peptides, polypeptides, small molecules, etc.). In some embodiments, a linker is a polymer of one or more repeating or non-repeating monomer units (e.g., nucleic acid, amino acid, carbon-containing polymer, carbon chain, etc.). A wide variety of linkers may be used. In some embodiments, the linker is a single covalent bond. In some embodiments, the linker comprises a linear or branched, cyclic or heterocyclic, saturated or unsaturated, structure having 1-20 nonhydrogen atoms (e.g., C, N, P, O and S) and is composed of any combination of alkyl, ether, thioether, imine, carboxylic, amine, ester, carboxamide, sulfonamide, hydrazide bonds and aromatic or heteroaromatic bonds. In some embodiments, linkers are longer than 20 nonhydrogen atoms (e.g. 21 non-hydrogen atoms, 25 non-hydrogen atoms, 30 non-hydrogen atoms, 40 non-hydrogen atoms, 50 non-hydrogen atoms, 100 non-hydrogen atoms, etc.) In some embodiments, the linker comprises 1-50 non-hydrogen atoms (in addition to hydrogen atoms) selected from the group of C, N, P, O and S (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 non-hydrogen atoms).

The present invention is not limited by the types of linkers available. The signal and interaction elements are linked, either directly (e.g. linker consists of a single covalent bond) or linked via a suitable linker. The present invention is not limited to any particular linker group. A variety of linker groups are contemplated, and suitable linkers could comprise, but are not limited to, alkyl groups, methylene carbon chains, ether, polyether, alkyl amide linker, a peptide linker, a modified peptide linker, a Poly(ethylene glycol) (PEG) linker, a streptavidin-biotin or avidin-biotin linker, polyaminoacids (e.g. polylysine), functionalised PEG, polysaccharides, glycosaminoglycans, dendritic polymers (WO93/06868 and by Tomalia et al. in Angew. Chem. Int. Ed. Engl. 29:138-175 (1990), herein incorporated by reference in their entireties), PEG-chelant polymers (W94/08629, WO94/09056 and WO96/26754, herein incorporated by reference in their entireties), oligonucleotide linker, phospholipid derivatives, alkenyl chains, alkynyl chains, disulfide, or a combination thereof.

In some embodiments, the linker is cleavable (e.g., enzymatically (e.g., TEV protease site), chemically, photoinduced, etc.).

In some embodiments, substantially non-luminescent internal tags are directly linked to peptide and/or polypeptide sequences. In some embodiments, two or more internal tags reside at a location internal to a polypeptide of interest. In some embodiments, one or more internal tags serve a linker function, rather than a reporter function.

In some embodiments, substantially non-luminescent internal tags and structural complements thereof are provided with less than 100% sequence identity and/or similarity to any portion of an existing luciferase (e.g., a firefly luciferase, a *Renilla* luciferase, an *Oplophorus* luciferase, enhanced *Oplophorus* luciferases as described in U.S. Pat. No. 8,557,970; U.S. Pat. App. 2014/0120548; U.S. Pat. No. 8,669,103; U.S. patent application Ser. No. 14/160,278; and U.S. patent application Ser. No. 14/160,282, herein incorporated by reference in their entireties). Certain embodiments of the present invention involve the formation of bioluminescent complexes of substantially non-luminescent internal tags and substantially non-luminescent structural complements with less than 100%, but more than 30% (e.g., >30%, >40%, >45%, >50%, >55%, >60%, >65%, >70%, >75%, >80%, >85%, >90%, >95%, >98%, >99%) sequence identity with all or a portion (e.g., >5, >8, >10, >12, >15, >20, <15, <18, <20, <22, <25, <30, <40, and ranges defined thereby) of SEQ ID NO: 2157 (e.g., complete NANOLUC sequence). In some embodiments, substantially non-luminescent internal tags and substantially non-luminescent structural complements are provided with less than 100%, but more than 30% (e.g., >30%, >40%, >45%, >50%, >55%, >60%, >65%, >70%, >75%, >80%, >85%, >90%, >95%, >98%, >99%) sequence similarity with a portion (e.g., >5, >8, >10, >12, >15, >20, <15, <18, <20, <22, <25, <30, <40, and ranges defined thereby) of SEQ ID NO: 2157 (e.g., peptides and polypeptides that interact to form bioluminescent complexes). In some embodiments, substantially non-luminescent internal tags and substantially non-luminescent structural complements are provided that have less than 100%, but more than 30% (e.g., >30%, >40%, >45%, >50%, >55%, >60%, >65%, >70%, >75%, >80%, >85%, >90%, >95%, >98%, >99%) sequence identity and/or similarity with about a 25 amino acid or less portion of SEQ ID NO: 2157, wherein such peptides form a bioluminescent complex when combined under appropriate conditions (e.g., stabilized by an interaction pair) with a polypeptide having less than 100%, but more than 30% (e.g., >30%, >40%, >45%, >50%, >55%, >60%, >65%, >70%, >75%, >80%, >85%, >90%, >95%, >98%, >99%) sequence identity and/or similarity with another portion SEQ ID NO: 2157. Similarly, substantially non-luminescent internal tags and substantially non-luminescent structural complements are provided that have less than 100%, but more than 40% (e.g., >40%, >45%, >50%, >55%, >60%, >65%, >70%, >75%, >80%, >85%, >90%, >95%, >98%, >99%) sequence identity or similarity with a portion of SEQ ID NO: 2157, wherein such substantially non-luminescent internal tags and substantially non-luminescent structural complements form a bioluminescent complex when combined under appropriate conditions (e.g., stabilized by an interaction pair) with a peptide having less than 100%, but more than 30% (e.g., >30%, >40%, >45%, >50%, >55%, >60%, >65%, >70%, >75%, >80%, >85%, >90%, >95%, >98%, >99%) sequence identity and/or similarity with another portion SEQ ID NO: 2157. In some embodiments, substantially non-luminescent internal tags and substantially non-luminescent structural complements with less than 100%, but more than 30% (e.g., >30%, >40%, >45%, >50%, >55%, >60%, >65%, >70%, >75%, >80%, >85%, >90%, >95%, >98%, >99%) sequence identity or similarity with SEQ ID NO: 2 are provided. In some embodiments, substantially non-luminescent internal tags and substantially non-luminescent structural complements with less than 100%, but more than 30% (e.g., >30%, >40%, >45%, >50%, >55%, >60%, >65%, >70%, >75%, >80%, >85%, >90%, >95%, >98%, >99%) sequence identity or similarity with SEQ ID NO: 440 are provided.

In some embodiments, internal tags and/or structural complements that find use in embodiments of the present invention include peptides with one or more amino acid substitutions, deletions, or additions from GVTGWRLCK-RILA (SEQ ID NO: 2). In some embodiments, the provided herein are internal tags and/or structural complements comprising an amino acid sequence of Table 1, and/or nucleic acids comprising the nucleic acid sequences of Table 1 (which code for the peptide sequences of Table 1).

TABLE 1

Exemplary internal tag and/or structural complement peptide sequences

| SEQ ID NO. | PEPTIDE NO. | POLYMER | SEQUENCE |
|---|---|---|---|
| 3 | NLpep2 (w/ Met) | N.A. | ATGGACGTGACCGGCTGGCGGCTGTGCGAACGCATTCTGGCG |
| 4 | NLpep2 (w/ Met) | A.A. | MDVTGWRLCERILA |
| 5 | NLpep3 (w/ Met) | N.A. | ATGGGAGTGACCGCCTGGCGGCTGTGCGAACGCATTCTGGCG |
| 6 | NLpep3 (w/ Met) | A.A. | MGVTAWRLCERILA |
| 7 | NLpep4 (w/ Met) | N.A. | ATGGGAGTGACCGGCTGGCGGCTGTGCAAGCGCATTCTGGCG |
| 8 | NLpep4 (w/ Met) | A.A. | MGVTGWRLCKRILA |
| 9 | NLpep5 (w/ Met) | N.A. | ATGGGAGTGACCGGCTGGCGGCTGTGCGAACGCATTAGCGCG |
| 10 | NLpep5 (w/ Met) | A.A. | MGVTGWRLCERISA |
| 11 | NLpep6 (w/ Met) | N.A. | ATGGACGTGACCGGCTGGCGGCTGTGCAAGCGCATTAGCGCG |
| 12 | NLpep6 (w/ Met) | A.A. | MDVTGWRLCKRISA |
| 13 | NLpep7 (w/ Met) | N.A. | ATGGACGTGACCGGCTGGCGGCTGTGCAAGCGCATTCTGGCG |
| 14 | NLpep7 (w/ Met) | A.A. | MDVTGWRLCKRILA |

TABLE 1-continued

Exemplary internal tag and/or structural complement peptide sequences

| SEQ ID NO. | PEPTIDE NO. | POLY MER | SEQUENCE |
|---|---|---|---|
| 15 | NLpep8 (w/ Met) | N.A. | ATGGACGTGACCGGCTGGCGGCTGTGCGAACGCATTAGCGCG |
| 16 | NLpep8 (w/ Met) | A.A. | MDVTGWRLCERISA |
| 17 | NLpep9 (w/ Met) | N.A. | ATGGGAGTGACCGGCTGGCGGCTGTGCAAGCGCATTAGCGCG |
| 18 | NLpep9 (w/ Met) | A.A. | MGVTGWRLCKRISA |
| 19 | NLpep10 (w/ Met) | N.A. | ATGGGAGTGACCGGCTGGCGGCTGAACGAACGCATTCTGGCG |
| 20 | NLpep10 (w/ Met) | A.A. | MGVTGWRLNERILA |
| 21 | NLpep11 (w/ Met) | N.A. | ATGGGAGTGACCGGCTGGCGGCTGCAGGAACGCATTCTGGCG |
| 22 | NLpep11 (w/ Met) | A.A. | MGVTGWRLQERILA |
| 23 | NLpep12 (w/ Met) | N.A. | ATGGGAGTGACCGGCTGGCGGCTGAAGAAGCGCCGGAGCCGG |
| 24 | NLpep12 (w/ Met) | A.A. | MGVTGWRLKKRRSR |
| 25 | NLpep13 (w/ Met) | N.A. | ATGAACGTGACCGGCTGGCGGCTGTGCAAGCGCATTAGCGCG |
| 26 | NLpep13 (w/ Met) | A.A. | MNVTGWRLCKRISA |
| 27 | NLpep14 (w/ Met) | N.A. | ATGAGCGTGACCGGCTGGCGGCTGTGCAAGCGCATTAGCGCG |
| 28 | NLpep14 (w/ Met) | A.A. | MSVTGWRLCKRISA |
| 29 | NLpep15 (w/ Met) | N.A. | ATGGAGGTGACCGGCTGGCGGCTGTGCAAGCGCATTAGCGCG |
| 30 | NLpep15 (w/ Met) | A.A. | MEVTGWRLCKRISA |
| 31 | NLpep16 (w/ Met) | N.A. | ATGGGCGTGACCGGCTGGCGGCTGTGCAAGCGCATTAGCGCG |
| 32 | NLpep16 (w/ Met) | A.A. | MHVTGWRLCKRISA |
| 33 | NLpep17 (w/ Met) | N.A. | ATGGGACACACCGGCTGGCGGCTGTGCAAGCGCATTAGCGCG |
| 34 | NLpep17 (w/ Met) | A.A. | MGITGWRLCKRISA |
| 35 | NLpep18 (w/ Met) | N.A. | ATGGGAGCCACCGGCTGGCGGCTGTGCAAGCGCATTAGCGCG |
| 36 | NLpep18 (w/ Met) | A.A. | MGATGWRLCKRISA |
| 37 | NLpep19 (w/ Met) | N.A. | ATGGGAAAGACCGGCTGGCGGCTGTGCAAGCGCATTAGCGCG |
| 38 | NLpep19 (w/ Met) | A.A. | MGKTGWRLCKRISA |
| 39 | NLpep20 (w/ Met) | N.A. | ATGGGACAGACCGGCTGGCGGCTGTGCAAGCGCATTAGCGCG |
| 40 | NLpep20 (w/ Met) | A.A. | MGQTGWRLCKRISA |
| 41 | NLpep21 (w/ Met) | N.A. | ATGGGAAGCACCGGCTGGCGGCTGTGCAAGCGCATTAGCGCG |
| 42 | NLpep21 (w/ Met) | A.A. | MGSTGWRLCKRISA |
| 43 | NLpep22 (w/ Met) | N.A. | ATGGGAGTGGTGGGCTGGCGGCTGTGCAAGCGCATTAGCGCG |
| 44 | NLpep22 (w/ Met) | A.A. | MGVVGWRLCKRISA |
| 45 | NLpep23 (w/ Met) | N.A. | ATGGGAGTGAAGGGCTGGCGGCTGTGCAAGCGCATTAGCGCG |
| 46 | NLpep23 (w/ Met) | A.A. | MGVKGWRLCKRISA |
| 47 | NLpep24 (w/ Met) | N.A. | ATGGGAGTGCAGGGCTGGCGGCTGTGCAAGCGCATTAGCGCG |
| 48 | NLpep24 (w/ Met) | A.A. | MGVQGWRLCKRISA |
| 49 | NLpep25 (w/ Met) | N.A. | ATGGGAGTGACCGGCACCCGGCTGTGCAAGCGCATTAGCGCG |
| 50 | NLpep25 (w/ Met) | A.A. | MGVTGTRLCKRISA |
| 51 | NLpep26 (w/ Met) | N.A. | ATGGGAGTGACCGGCAAGCGGCTGTGCAAGCGCATTAGCGCG |

TABLE 1-continued

Exemplary internal tag and/or structural complement peptide sequences

| SEQ ID NO. | PEPTIDE NO. | POLYMER | SEQUENCE |
|---|---|---|---|
| 52 | NLpep26 (w/ Met) | A.A. | MGVTGKRLCKRISA |
| 53 | NLpep27 (w/ Met) | N.A. | ATGGGAGTGACCGGCGTGCGGCTGTGCAAGCGCATTAGCGCG |
| 54 | NLpep27 (w/ Met) | A.A. | MGVTGVRLCKRISA |
| 55 | NLpep28 (w/ Met) | N.A. | ATGGGAGTGACCGGCTGGCGGCACTGCAAGCGCATTAGCGCG |
| 56 | NLpep28 (w/ Met) | A.A. | MGVTGWRICKRISA |
| 57 | NLpep29 (w/ Met) | N.A. | ATGGGAGTGACCGGCTGGCGGGTGTGCAAGCGCATTAGCGCG |
| 58 | NLpep29 (w/ Met) | A.A. | MGVTGWRVCKRISA |
| 59 | NLpep30 (w/ Met) | N.A. | ATGGGAGTGACCGGCTGGCGGACCTGCAAGCGCATTAGCGCG |
| 60 | NLpep30 (w/ Met) | A.A. | MGVTGWRTCKRISA |
| 61 | NLpep31 (w/ Met) | N.A. | ATGGGAGTGACCGGCTGGCGGTACTGCAAGCGCATTAGCGCG |
| 62 | NLpep31 (w/ Met) | A.A. | MGVTGWRYCKRISA |
| 63 | NLpep32 (w/ Met) | N.A. | ATGGGAGTGACCGGCTGGCGGAAGTGCAAGCGCATTAGCGCG |
| 64 | NLpep32 (w/ Met) | A.A. | MGVTGWRKCKRISA |
| 65 | NLpep33 (w/ Met) | N.A. | ATGGGAGTGACCGGCTGGCGGCTGAACAAGCGCATTAGCGCG |
| 66 | NLpep33 (w/ Met) | A.A. | MGVTGWRLNKRISA |
| 67 | NLpep34 (w/ Met) | N.A. | ATGGGAGTGACCGGCTGGCGGCTGACCAAGCGCATTAGCGCG |
| 68 | NLpep34 (w/ Met) | A.A. | MGVTGWRLTKRISA |
| 69 | NLpep35 (w/ Met) | N.A. | ATGGGAGTGACCGGCTGGCGGCTGTGCAAGAAGATTAGCGCG |
| 70 | NLpep35 (w/ Met) | A.A. | MGVTGWRLCKKISA |
| 71 | NLpep36 (w/ Met) | N.A. | ATGGGAGTGACCGGCTGGCGGCTGTGCAAGAACATTAGCGCG |
| 72 | NLpep36 (w/ Met) | A.A. | MGVTGWRLCKNISA |
| 73 | NLpep37 (w/ Met) | N.A. | ATGGGAGTGACCGGCTGGCGGCTGTGCAAGCGCGTGAGCGCG |
| 74 | NLpep37 (w/ Met) | A.A. | MGVTGWRLCKRVSA |
| 75 | NLpep38 (w/ Met) | N.A. | ATGGGAGTGACCGGCTGGCGGCTGTGCAAGCGCCAGAGCGCG |
| 76 | NLpep38 (w/ Met) | A.A. | MGVTGWRLCKRQSA |
| 77 | NLpep39 (w/ Met) | N.A. | ATGGGAGTGACCGGCTGGCGGCTGTGCAAGCGCGAGAGCGCG |
| 78 | NLpep39 (w/ Met) | A.A. | MGVTGWRLCKRESA |
| 79 | NLpep40 (w/ Met) | N.A. | ATGGGAGTGACCGGCTGGCGGCTGTGCAAGCGCCGGAGCGCG |
| 80 | NLpep40 (w/ Met) | A.A. | MGVTGWRLCKRRSA |
| 81 | NLpep41 (w/ Met) | N.A. | ATGGGAGTGACCGGCTGGCGGCTGTGCAAGCGCTTCAGCGCG |
| 82 | NLpep41 (w/ Met) | A.A. | MGVTGWRLCKRFSA |
| 83 | NLpep42 (w/ Met) | N.A. | ATGGGAGTGACCGGCTGGCGGCTGTGCAAGCGCATTAGCAAC |
| 84 | NLpep42 (w/ Met) | A.A. | MGVTGWRLCKRISN |
| 85 | NLpep43 (w/ Met) | N.A. | ATGGGAGTGACCGGCTGGCGGCTGTGCAAGCGCATTAGCACC |
| 86 | NLpep43 (w/ Met) | A.A. | MGVTGWRLCKRIST |
| 87 | NLpep44 (w/ Met) | N.A. | ATGGGAGTGACCGGCTGGCGGCTGTGCAAGCGCATTAGCCGG |
| 88 | NLpep44 (w/ Met) | A.A. | MGVTGWRLCKRISR |

TABLE 1-continued

Exemplary internal tag and/or structural complement peptide sequences

| SEQ ID NO. | PEPTIDE NO. | POLYMER | SEQUENCE |
|---|---|---|---|
| 89 | NLpep45 (w/ Met) | N.A. | ATGGGAGTGACCGGCTGGCGGCTGTGCAAGCGCATTAGCCTG |
| 90 | NLpep45 (w/ Met) | A.A. | MGVTGWRLCKRISL |
| 91 | NLpep46 (w/ Met) | N.A. | ATGGGAGTGACCGGCTGGCGGCTGTGCAAGCGCATTAGCGAG |
| 92 | NLpep46 (w/ Met) | A.A. | MGVTGWRLCKRISE |
| 93 | NLpep47 (w/ Met) | N.A. | ATGGGAGTGACCGGCTTCCGGCTGTGCAAGCGCATTAGCGCG |
| 94 | NLpep47 (w/ Met) | A.A. | MGVTGFRLCKRISA |
| 95 | NLpep48 (w/ Met) | N.A. | ATGGGAGTGACCGGCTACCGGCTGTGCAAGCGCATTAGCGCG |
| 96 | NLpep48 (w/ Met) | A.A. | MGVTGYRLCKRISA |
| 97 | NLpep49 (w/ Met) | N.A. | ATGGGAGTGACCGGCGAGCGGCTGTGCAAGCGCATTAGCGCG |
| 98 | NLpep49 (w/ Met) | A.A. | MGVTGERLCKRISA |
| 99 | NLpep50 (w/ Met) | N.A. | ATGCAGGTGACCGGCTGGCGGCTGTGCAAGCGCATTAGCGCG |
| 100 | NLpep50 (w/ Met) | A.A. | MQVTGWRLCKRISA |
| 101 | NLpep51 (w/ Met) | N.A. | ATGACCGTGACCGGCTGGCGGCTGTGCAAGCGCATTAGCGCG |
| 102 | NLpep51 (w/ Met) | A.A. | MTVTGWRLCKRISA |
| 103 | NLpep52 (w/ Met) | N.A. | ATGGGAGTGGAGGGCTGGCGGCTGTGCAAGCGCATTAGCGCG |
| 104 | NLpep52 (w/ Met) | A.A. | MGVEGWRLCKRISA |
| 105 | NLpep53 (w/ Met) | N.A. | ATGGGAGTGACCGGCTGGCGGCTGTTCAAGCGCATTAGCGCG |
| 106 | NLpep53 (w/ Met) | A.A. | MGVTGWRLFKRISA |
| 107 | NLpep54 (w/ Met) | N.A. | ATGGGAGTGACCGGCTGGCGGCTGTACAAGCGCATTAGCGCG |
| 108 | NLpep54 (w/ Met) | A.A. | MGVTGWRLYKRISA |
| 109 | NLpep55 (w/ Met) | N.A. | ATGGGAGTGACCGGCTGGCGGCTGAGCAAGCGCATTAGCGCG |
| 110 | NLpep55 (w/ Met) | A.A. | MGVTGWRLSKRISA |
| 111 | NLpep56 (w/ Met) | N.A. | ATGGGAGTGACCGGCTGGCGGCTGGGCAAGCGCATTAGCGCG |
| 112 | NLpep56 (w/ Met) | A.A. | MGVTGWRLHKRISA |
| 113 | NLpep57 (w/ Met) | N.A. | ATGGGAGTGACCGGCTGGCGGCTGATGAAGCGCATTAGCGCG |
| 114 | NLpep57 (w/ Met) | A.A. | MGVTGWRLMKRISA |
| 115 | NLpep58 (w/ Met) | N.A. | ATGGGAGTGACCGGCTGGCGGCTGGCCAAGCGCATTAGCGCG |
| 116 | NLpep58 (w/ Met) | A.A. | MGVTGWRLAKRISA |
| 117 | NLpep59 (w/ Met) | N.A. | ATGGGAGTGACCGGCTGGCGGCTGCAGAAGCGCATTAGCGCG |
| 118 | NLpep59 (w/ Met) | A.A. | MGVTGWRLQKRISA |
| 119 | NLpep60 (w/ Met) | N.A. | ATGGGAGTGACCGGCTGGCGGCTGCTGAAGCGCATTAGCGCG |
| 120 | NLpep60 (w/ Met) | A.A. | MGVTGWRLLKRISA |
| 121 | NLpep61 (w/ Met) | N.A. | ATGGGAGTGACCGGCTGGCGGCTGAAGAAGCGCATTAGCGCG |
| 122 | NLpep61 (w/ Met) | A.A. | MGVTGWRLKKRISA |
| 123 | NLpep62 (w/ Met) | N.A. | ATGAACCACACCGGCTGGCGGCTGAACAAGAAGGTGAGCAAC |
| 124 | NLpep62 (w/ Met) | A.A. | MNITGWRLNKKVSN |
| 125 | NLpep63 (w/ Met) | N.A. | ATGAACCACACCGGCTACCGGCTGAACAAGAAGGTGAGCAAC |

TABLE 1-continued

Exemplary internal tag and/or structural complement peptide sequences

| SEQ ID NO. | PEPTIDE NO. | POLYMER | SEQUENCE |
|---|---|---|---|
| 126 | NLpep63 (w/ Met) | A.A. | MNITGYRLNKKVSN |
| 127 | NLpep64 (w/ Met) | N.A. | ATGTGCGTGACCGGCTGGCGGCTGTTCAAGCGCATTAGCGCG |
| 128 | NLpep64 (w/ Met) | A.A. | MCVTGWRLFKRISA |
| 129 | NLpep65 (w/ Met) | N.A. | ATGCCCGTGACCGGCTGGCGGCTGTTCAAGCGCATTAGCGCG |
| 130 | NLpep65 (w/ Met) | A.A. | MPVTGWRLFKRISA |
| 131 | NLpep66 (w/ Met) | N.A. | ATGAACCACACCGGCTACCGGCTGTTCAAGAAGGTGAGCAAC |
| 132 | NLpep66 (w/ Met) | A.A. | MNITGYRLFKKVSN |
| 133 | NLpep67 (w/ Met) | N.A. | ATGAACGTGACCGGCTACCGGCTGTTCAAGAAGGTGAGCAAC |
| 134 | NLpep67 (w/ Met) | A.A. | MNVTGYRLFKKVSN |
| 135 | NLpep68 (w/ Met) | N.A. | ATGAACGTGACCGGCTGGCGGCTGTTCAAGAAGGTGAGCAAC |
| 136 | NLpep68 (w/ Met) | A.A. | MNVTGWRLFKKVSN |
| 137 | NLpep69 (w/ Met) | N.A. | ATGAACGTGACCGGCTGGCGGCTGTTCAAGAAGATTAGCAAC |
| 138 | NLpep69 (w/ Met) | A.A. | MNVTGWRLFKKISN |
| 139 | NLpep70 (w/ Met) | N.A. | ATGAACGTGACCGGCTGGCGGCTGTTCAAGCGCATTAGCAAC |
| 140 | NLpep70 (w/ Met) | A.A. | MNVTGWRLFKRISN |
| 141 | NLpep71 (w/ Met) | N.A. | ATGGGAGTGACCGGCTGGCGGCTGTTCAAGCGCATTAGCAAC |
| 142 | NLpep71 (w/ Met) | A.A. | MGVTGWRLFKRISN |
| 143 | NLpep72 (w/ Met) | N.A. | ATGAACGTGACCGGCTGGCGGCTGTTCGAACGCATTAGCAAC |
| 144 | NLpep72 (w/ Met) | A.A. | MNVTGWRLFERISN |
| 145 | NLpep73 (w/ Met) | N.A. | ATGAACGTGACCGGCTGGCGGCTGTTCAAGCGCATTCTGAAC |
| 146 | NLpep73 (w/ Met) | A.A. | MNVTGWRLFKRILN |
| 147 | NLpep74 (w/ Met) | N.A. | ATGAACGTGACCGGCTGGCGGCTGTTCAAGCGCATTAGCGCG |
| 148 | NLpep74 (w/ Met) | A.A. | MNVTGWRLFKRISA |
| 149 | NLpep75 (w/ Met) | N.A. | ATGAACGTGACCGGCTGGCGGCTGTTCGAAAAGATTAGCAAC |
| 150 | NLpep75 (w/ Met) | A.A. | MNVTGWRLFEKISN |
| 151 | NLpep76 (w/ Met) | N.A. | ATGAACGTGAGCGGCTGGCGGCTGTTCGAAAAGATTAGCAAC |
| 152 | NLpep76 (w/ Met) | A.A. | MNVSGWRLFEKISN |
| 153 | NLpep77 (w/ Met) | N.A. | ATG-GTGACCGGCTGGCGGCTGTTCAAGAAGATTAGCAAC |
| 154 | NLpep77 (w/ Met) | A.A. | M-VTGWRLFKKISN |
| 155 | NLpep78 (w/ Met) | N.A. | ATGAACGTGAGCGGCTGGCGGCTGTTCAAGAAGATTAGCAAC |
| 156 | NLpep78 (w/ Met) | A.A. | MNVSGWRLFKKISN |
| 157 | NLpep79 (w/ Met) | N.A. | ATGAACGTGACCGGCTACCGGCTGTTCAAGAAGATTAGCAAC |
| 158 | NLpep79 (w/ Met) | A.A. | MNVTGYRLFKKISN |
| 159 | NLpep80 (w/ Met) | N.A. | ATGGTGAGCGGCTGGCGGCTGTTCAAGAAGATTAGCAAC |
| 160 | NLpep80 (w/ Met) | A.A. | MVSGWRLFKKISN |
| 161 | NLpep81 (w/ Met) | N.A. | ATGAGCGGCTGGCGGCTGTTCAAGAAGATTAGCAAC |
| 440 | NLpep81 (w/ Met) | A.A. | MSGWRLFKKISN |

TABLE 1-continued

Exemplary internal tag and/or structural complement peptide sequences

| SEQ ID NO. | PEPTIDE NO. | POLYMER | SEQUENCE |
|---|---|---|---|
| 163 | NLpep82 (w/ Met) | N.A. | ATGGGCTGGCGGCTGTTCAAGAAGATTAGCAAC |
| 164 | NLpep82 (w/ Met) | A.A. | MGWRLFKKISN |
| 165 | NLpep83 (w/ Met) | N.A. | ATGAACGTGAGCGGCTGGCGGCTGTTCAAGAAGATTAGC |
| 166 | NLpep83 (w/ Met) | A.A. | MNVSGWRLFKKIS |
| 167 | NLpep84 (w/ Met) | N.A. | ATGAACGTGAGCGGCTGGCGGCTGTTCAAGAAGATT |
| 168 | NLpep84 (w/ Met) | A.A. | MNVSGWRLFKKI |
| 169 | NLpep85 (w/ Met) | N.A. | ATGAACGTGAGCGGCTGGCGGCTGTTCAAGAAG |
| 170 | NLpep85 (w/ Met) | A.A. | MNVSGWRLFKK |
| 171 | NLpep86 (w/ Met) | N.A. | ATGGTGAGCGGCTGGCGGCTGTTCAAGAAGATTAGC |
| 172 | NLpep86 (w/ Met) | A.A. | MVSGWRLFKKIS |
| 173 | NLpep87 (w/ Met) | N.A. | ATGAGCGGCTGGCGGCTGTTCAAGAAGATT |
| 174 | NLpep87 (w/ Met) | A.A. | MSGWRLFKKI |
| 175 | NLpep88 (w/ Met) | N.A. | ATGAACGTGAGCGGCTGGGGCCTGTTCAAGAAGATTAGCAAC |
| 176 | NLpep88 (w/ Met) | A.A. | MNVSGWGLFKKISN |
| 177 | NLpep89 (w/ Met) | N.A. | ATGCCCGTGAGCGGCTGGCGGCTGTTCAAGAAGATTAGCAAC |
| 178 | NLpep89 (w/ Met) | A.A. | MPVSGWRLFKKISN |
| 179 | NLpep90 (w/ Met) | N.A. | ATGAACCCCGTGAGCGGCTGGCGGCTGTTCAAGAAGATTAGCAAC |
| 180 | NLpep90 (w/ Met) | A.A. | MNPVSGWRLFKKISN |
| 181 | NLpep91 (w/ Met) | N.A. | ATGATCAACCCCGTGAGCGGCTGGCGGCTGTTCAAGAAGATTAGCAAC |
| 182 | NLpep91 (w/ Met) | A.A. | MINPVSGWRLFKKISN |
| 183 | NLpep92 (w/ Met) | N.A. | ATGACCATCAACCCCGTGAGCGGCTGGCGGCTGTTCAAGAAGATTAGCAAC |
| 184 | NLpep92 (w/ Met) | A.A. | MTINPVSGWRLFKKISN |
| 185 | NLpep93 (w/ Met) | N.A. | ATGGTGACCATCAACCCCGTGAGCGGCTGGCGGCTGTTCAAGAAGATTAGCAAC |
| 186 | NLpep93 (w/ Met) | A.A. | MVTINPVSGWRLFKKISN |
| 187 | NLpep94 (w/ Met) | N.A. | ATGCGGGTGACCATCAACCCCGTGAGCGGCTGGCGGCTGTTCAAGAAGATTAGCAAC |
| 188 | NLpep94 (w/ Met) | A.A. | MRVTINPVSGWRLFKKISN |
| 189 | NLpep95 (w/ Met) | N.A. | ATGAGCGGCTGGCGGCTGCTGAAGAAGATT |
| 190 | NLpep95 (w/ Met) | A.A. | MSGWRLLKKI |
| 191 | NLpep96 (w/ Met) | N.A. | ATGACCGGCTACCGGCTGCTGAAGAAGATT |
| 192 | NLpep96 (w/ Met) | A.A. | MTGYRLLKKI |
| 193 | NLpep97 (w/ Met) | N.A. | ATGAGCGGCTGGCGGCTGTTCAAGAAG |
| 194 | NLpep97 (w/ Met) | A.A. | MSGWRLFKK |
| 195 | NLpep98 (w/ Met) | N.A. | ATGGTGACCGGCTACCGGCTGTTCAAGAAGATTAGC |
| 196 | NLpep98 (w/ Met) | A.A. | MVTGYRLFKKIS |
| 197 | NLpep99 (w/ Met) | N.A. | ATGGTGACCGGCTACCGGCTGTTCGAGAAGATTAGC |

TABLE 1-continued

Exemplary internal tag and/or structural complement peptide sequences

| SEQ ID NO. | PEPTIDE NO. | POLYMER | SEQUENCE |
|---|---|---|---|
| 198 | NLpep99 (w/ Met) | A.A. | MVTGYRLFEKIS |
| 199 | NLpep100 (w/ Met) | N.A. | ATGGTGACCGGCTACCGGCTGTTCGAGCAGATTAGC |
| 200 | NLpep100 (w/ Met) | A.A. | MVTGYRLFEQIS |
| 201 | NLpep101 (w/ Met) | N.A. | ATGGTGACCGGCTACCGGCTGTTCGAGAAGGAGAGC |
| 202 | NLpep101 (w/ Met) | A.A. | MVTGYRLFEKES |
| 203 | NLpep102 (w/ Met) | N.A. | ATGGTGACCGGCTACCGGCTGTTCGAGCAGGAGAGC |
| 204 | NLpep102 (w/ Met) | A.A. | MVTGYRLFEQES |
| 205 | NLpep103 (w/ Met) | N.A. | ATGGTGACCGGCTACCGGCTGTTCGAGCAGGAGCTG |
| 206 | NLpep103 (w/ Met) | A.A. | MVTGYRLFEQEL |
| 207 | NLpep104 (w/ Met) | N.A. | ATGGTGGAGGGCTACCGGCTGTTCGAGAAGATTAGC |
| 208 | NLpep104 (w/ Met) | A.A. | MVEGYRLFEKIS |
| 209 | NLpep105 (w/ Met) | N.A. | ATGGTGGAGGGCTACCGGCTGTTCGAGCAGATTAGC |
| 210 | NLpep105 (w/ Met) | A.A. | MVEGYRLFEQIS |
| 211 | NLpep106 (w/ Met) | N.A. | ATGGTGGAGGGCTACCGGCTGTTCGAGAAGGAGAGC |
| 212 | NLpep106 (w/ Met) | A.A. | MVEGYRLFEKES |
| 213 | NLpep107 (w/ Met) | N.A. | ATGGTGGAGGGCTACCGGCTGTTCGAGCAGGAGAGC |
| 214 | NLpep107 (w/ Met) | A.A. | MVEGYRLFEQES |
| 215 | NLpep108 (w/ Met) | N.A. | ATGGTGGAGGGCTACCGGCTGTTCGAGCAGGAGCTG |
| 216 | NLpep108 (w/ Met) | A.A. | MVEGYRLFEQEL |
| 217 | NLpep109 (w/ Met) | N.A. | ATGATTAGCGGCTGGCGGCTGATGAAGAACATTAGC |
| 218 | NLpep109 (w/ Met) | A.A. | MISGWRLMKNIS |
| 219 | NLpep110 (w/ Met) | N.A. | ATGGTGGAGGGCTACCGGCTGTTCAAGAAGATTAGC |
| 220 | NLpep110 (w/ Met) | A.A. | MVEGYRLFKKIS |
| 221 | NLpep2 (w/o Met) | N.A. | GACGTGACCGGCTGGCGGCTGTGCGAACGCATTCTGGCG |
| 222 | NLpep2 (w/o Met) | A.A. | DVTGWRLCERILA |
| 223 | NLpep3 (w/o Met) | N.A. | GGAGTGACCGCCTGGCGGCTGTGCGAACGCATTCTGGCG |
| 224 | NLpep3 (w/o Met) | A.A. | GVTAWRLCERILA |
| 225 | NLpep4 (w/o Met) | N.A. | GGAGTGACCGGCTGGCGGCTGTGCAAGCGCATTCTGGCG |
| 226 | NLpep4 (w/o Met) | A.A. | GVTGWRLCKRILA |
| 227 | NLpep5 (w/o Met) | N.A. | GGAGTGACCGGCTGGCGGCTGTGCGAACGCATTAGCGCG |
| 228 | NLpep5 (w/o Met) | A.A. | GVTGWRLCERISA |
| 229 | NLpep6 (w/o Met) | N.A. | GACGTGACCGGCTGGCGGCTGTGCAAGCGCATTAGCGCG |
| 230 | NLpep6 (w/o Met) | A.A. | DVTGWRLCKRISA |
| 231 | NLpep7 (w/o Met) | N.A. | GACGTGACCGGCTGGCGGCTGTGCAAGCGCATTCTGGCG |
| 232 | NLpep7 (w/o Met) | A.A. | DVTGWRLCKRILA |
| 233 | NLpep8 (w/o Met) | N.A. | GACGTGACCGGCTGGCGGCTGTGCGAACGCATTAGCGCG |
| 234 | NLpep8 (w/o Met) | A.A. | DVTGWRLCERISA |

TABLE 1-continued

Exemplary internal tag and/or structural complement peptide sequences

| SEQ ID NO. | PEPTIDE NO. | POLY MER | SEQUENCE |
|---|---|---|---|
| 235 | NLpep9 (w/o Met) | N.A. | GGAGTGACCGGCTGGCGGCTGTGCAAGCGCATTAGCGCG |
| 236 | NLpep9 (w/o Met) | A.A. | GVTGWRLCKRISA |
| 237 | NLpep10 (w/o Met) | N.A. | GGAGTGACCGGCTGGCGGCTGAACGAACGCATTCTGGCG |
| 238 | NLpep10 (w/o Met) | A.A. | GVTGWRLNERILA |
| 239 | NLpep11 (w/o Met) | N.A. | GGAGTGACCGGCTGGCGGCTGCAGGAACGCATTCTGGCG |
| 240 | NLpep11 (w/o Met) | A.A. | GVTGWRLQERILA |
| 241 | NLpep12 (w/o Met) | N.A. | GGAGTGACCGGCTGGCGGCTGAAGAAGCGCCGGAGCCGG |
| 242 | NLpep12 (w/o Met) | A.A. | GVTGWRLKKRRSR |
| 243 | NLpep13 (w/o Met) | N.A. | AACGTGACCGGCTGGCGGCTGTGCAAGCGCATTAGCGCG |
| 244 | NLpep13 (w/o Met) | A.A. | NVTGWRLCKRISA |
| 245 | NLpep14 (w/o Met) | N.A. | AGCGTGACCGGCTGGCGGCTGTGCAAGCGCATTAGCGCG |
| 246 | NLpep14 (w/o Met) | A.A. | SVTGWRLCKRISA |
| 247 | NLpep15 (w/o Met) | N.A. | GAGGTGACCGGCTGGCGGCTGTGCAAGCGCATTAGCGCG |
| 248 | NLpep15 (w/o Met) | A.A. | EVTGWRLCKRISA |
| 249 | NLpep16 (w/o Met) | N.A. | GGCGTGACCGGCTGGCGGCTGTGCAAGCGCATTAGCGCG |
| 250 | NLpep16 (w/o Met) | A.A. | HVTGWRLCKRISA |
| 251 | NLpep17 (w/o Met) | N.A. | GGACACACCGGCTGGCGGCTGTGCAAGCGCATTAGCGCG |
| 252 | NLpep17 (w/o Met) | A.A. | GITGWRLCKRISA |
| 253 | NLpep18 (w/o Met) | N.A. | GGAGCCACCGGCTGGCGGCTGTGCAAGCGCATTAGCGCG |
| 254 | NLpep18 (w/o Met) | A.A. | GATGWRLCKRISA |
| 255 | NLpep19 (w/o Met) | N.A. | GGAAAGACCGGCTGGCGGCTGTGCAAGCGCATTAGCGCG |
| 256 | NLpep19 (w/o Met) | A.A. | GKTGWRLCKRISA |
| 257 | NLpep20 (w/o Met) | N.A. | GGACAGACCGGCTGGCGGCTGTGCAAGCGCATTAGCGCG |
| 258 | NLpep20 (w/o Met) | A.A. | GQTGWRLCKRISA |
| 259 | NLpep21 (w/o Met) | N.A. | GGAAGCACCGGCTGGCGGCTGTGCAAGCGCATTAGCGCG |
| 260 | NLpep21 (w/o Met) | A.A. | GSTGWRLCKRISA |
| 261 | NLpep22 (w/o Met) | N.A. | GGAGTGGTGGGCTGGCGGCTGTGCAAGCGCATTAGCGCG |
| 262 | NLpep22 (w/o Met) | A.A. | GVVGWRLCKRISA |
| 263 | NLpep23 (w/o Met) | N.A. | GGAGTGAAGGGCTGGCGGCTGTGCAAGCGCATTAGCGCG |
| 264 | NLpep23 (w/o Met) | A.A. | GVKGWRLCKRISA |
| 265 | NLpep24 (w/o Met) | N.A. | GGAGTGCAGGGCTGGCGGCTGTGCAAGCGCATTAGCGCG |
| 266 | NLpep24 (w/o Met) | A.A. | GVQGWRLCKRISA |
| 267 | NLpep25 (w/o Met) | N.A. | GGAGTGACCGGCACCCGGCTGTGCAAGCGCATTAGCGCG |
| 268 | NLpep25 (w/o Met) | A.A. | GVTGTRLCKRISA |
| 269 | NLpep26 (w/o Met) | N.A. | GGAGTGACCGGCAAGCGGCTGTGCAAGCGCATTAGCGCG |
| 270 | NLpep26 (w/o Met) | A.A. | GVTGKRLCKRISA |
| 271 | NLpep27 (w/o Met) | N.A. | GGAGTGACCGGCGTGCGGCTGTGCAAGCGCATTAGCGCG |

TABLE 1-continued

Exemplary internal tag and/or structural complement peptide sequences

| SEQ ID NO. | PEPTIDE NO. | POLYMER | SEQUENCE |
|---|---|---|---|
| 272 | NLpep27 (w/o Met) | A.A. | GVTGVRLCKRISA |
| 273 | NLpep28 (w/o Met) | N.A. | GGAGTGACCGGCTGGCGGCACTGCAAGCGCATTAGCGCG |
| 274 | NLpep28 (w/o Met) | A.A. | GVTGWRICKRISA |
| 275 | NLpep29 (w/o Met) | N.A. | GGAGTGACCGGCTGGCGGGTGTGCAAGCGCATTAGCGCG |
| 276 | NLpep29 (w/o Met) | A.A. | GVTGWRVCKRISA |
| 277 | NLpep30 (w/o Met) | N.A. | GGAGTGACCGGCTGGCGGACCTGCAAGCGCATTAGCGCG |
| 278 | NLpep30 (w/o Met) | A.A. | GVTGWRTCKRISA |
| 279 | NLpep31 (w/o Met) | N.A. | GGAGTGACCGGCTGGCGGTACTGCAAGCGCATTAGCGCG |
| 280 | NLpep31 (w/o Met) | A.A. | GVTGWRYCKRISA |
| 281 | NLpep32 (w/o Met) | N.A. | GGAGTGACCGGCTGGCGGAAGTGCAAGCGCATTAGCGCG |
| 282 | NLpep32 (w/o Met) | A.A. | GVTGWRKCKRISA |
| 283 | NLpep33 (w/o Met) | N.A. | GGAGTGACCGGCTGGCGGCTGAACAAGCGCATTAGCGCG |
| 284 | NLpep33 (w/o Met) | A.A. | GVTGWRLNKRISA |
| 285 | NLpep34 (w/o Met) | N.A. | GGAGTGACCGGCTGGCGGCTGACCAAGCGCATTAGCGCG |
| 286 | NLpep34 (w/o Met) | A.A. | GVTGWRLTKRISA |
| 287 | NLpep35 (w/o Met) | N.A. | GGAGTGACCGGCTGGCGGCTGTGCAAGAAGATTAGCGCG |
| 288 | NLpep35 (w/o Met) | A.A. | GVTGWRLCKKISA |
| 289 | NLpep36 (w/o Met) | N.A. | GGAGTGACCGGCTGGCGGCTGTGCAAGAACATTAGCGCG |
| 290 | NLpep36 (w/o Met) | A.A. | GVTGWRLCKNISA |
| 291 | NLpep37 (w/o Met) | N.A. | GGAGTGACCGGCTGGCGGCTGTGCAAGCGCGTGAGCGCG |
| 292 | NLpep37 (w/o Met) | A.A. | GVTGWRLCKRVSA |
| 293 | NLpep38 (w/o Met) | N.A. | GGAGTGACCGGCTGGCGGCTGTGCAAGCGCCAGAGCGCG |
| 294 | NLpep38 (w/o Met) | A.A. | GVTGWRLCKRQSA |
| 295 | NLpep39 (w/o Met) | N.A. | GGAGTGACCGGCTGGCGGCTGTGCAAGCGCGAGAGCGCG |
| 296 | NLpep39 (w/o Met) | A.A. | GVTGWRLCKRESA |
| 297 | NLpep40 (w/o Met) | N.A. | GGAGTGACCGGCTGGCGGCTGTGCAAGCGCCGGAGCGCG |
| 298 | NLpep40 (w/o Met) | A.A. | GVTGWRLCKRRSA |
| 299 | NLpep41 (w/o Met) | N.A. | GGAGTGACCGGCTGGCGGCTGTGCAAGCGCTTCAGCGCG |
| 300 | NLpep41 (w/o Met) | A.A. | GVTGWRLCKRFSA |
| 301 | NLpep42 (w/o Met) | N.A. | GGAGTGACCGGCTGGCGGCTGTGCAAGCGCATTAGCAAC |
| 302 | NLpep42 (w/o Met) | A.A. | GVTGWRLCKRISN |
| 303 | NLpep43 (w/o Met) | N.A. | GGAGTGACCGGCTGGCGGCTGTGCAAGCGCATTAGCACC |
| 304 | NLpep43 (w/o Met) | A.A. | GVTGWRLCKRIST |
| 305 | NLpep44 (w/o Met) | N.A. | GGAGTGACCGGCTGGCGGCTGTGCAAGCGCATTAGCCGG |
| 306 | NLpep44 (w/o Met) | A.A. | GVTGWRLCKRISR |
| 307 | NLpep45 (w/o Met) | N.A. | GGAGTGACCGGCTGGCGGCTGTGCAAGCGCATTAGCCTG |
| 308 | NLpep45 (w/o Met) | A.A. | GVTGWRLCKRISL |

TABLE 1-continued

Exemplary internal tag and/or structural complement peptide sequences

| SEQ ID NO. | PEPTIDE NO. | POLYMER | SEQUENCE |
|---|---|---|---|
| 309 | NLpep46 (w/o Met) | N.A. | GGAGTGACCGGCTGGCGGCTGTGCAAGCGCATTAGCGAG |
| 310 | NLpep46 (w/o Met) | A.A. | GVTGWRLCKRISE |
| 311 | NLpep47 (w/o Met) | N.A. | GGAGTGACCGGCTTCCGGCTGTGCAAGCGCATTAGCGCG |
| 312 | NLpep47 (w/o Met) | A.A. | GVTGFRLCKRISA |
| 313 | NLpep48 (w/o Met) | N.A. | GGAGTGACCGGCTACCGGCTGTGCAAGCGCATTAGCGCG |
| 314 | NLpep48 (w/o Met) | A.A. | GVTGYRLCKRISA |
| 315 | NLpep49 (w/o Met) | N.A. | GGAGTGACCGGCGAGCGGCTGTGCAAGCGCATTAGCGCG |
| 316 | NLpep49 (w/o Met) | A.A. | GVTGERLCKRISA |
| 317 | NLpep50 (w/o Met) | N.A. | CAGGTGACCGGCTGGCGGCTGTGCAAGCGCATTAGCGCG |
| 318 | NLpep50 (w/o Met) | A.A. | QVTGWRLCKRISA |
| 319 | NLpep51 (w/o Met) | N.A. | ACCGTGACCGGCTGGCGGCTGTGCAAGCGCATTAGCGCG |
| 320 | NLpep51 (w/o Met) | A.A. | TVTGWRLCKRISA |
| 321 | NLpep52 (w/o Met) | N.A. | GGAGTGGAGGGCTGGCGGCTGTGCAAGCGCATTAGCGCG |
| 322 | NLpep52 (w/o Met) | A.A. | GVEGWRLCKRISA |
| 323 | NLpep53 (w/o Met) | N.A. | GGAGTGACCGGCTGGCGGCTGTTCAAGCGCATTAGCGCG |
| 324 | NLpep53 (w/o Met) | A.A. | GVTGWRLFKRISA |
| 325 | NLpep54 (w/o Met) | N.A. | GGAGTGACCGGCTGGCGGCTGTACAAGCGCATTAGCGCG |
| 326 | NLpep54 (w/o Met) | A.A. | GVTGWRLYKRISA |
| 327 | NLpep55 (w/o Met) | N.A. | GGAGTGACCGGCTGGCGGCTGAGCAAGCGCATTAGCGCG |
| 328 | NLpep55 (w/o Met) | A.A. | GVTGWRLSKRISA |
| 329 | NLpep56 (w/o Met) | N.A. | GGAGTGACCGGCTGGCGGCTGGGCAAGCGCATTAGCGCG |
| 330 | NLpep56 (w/o Met) | A.A. | GVTGWRLHKRISA |
| 331 | NLpep57 (w/o Met) | N.A. | GGAGTGACCGGCTGGCGGCTGATGAAGCGCATTAGCGCG |
| 332 | NLpep57 (w/o Met) | A.A. | GVTGWRLMKRISA |
| 333 | NLpep58 (w/o Met) | N.A. | GGAGTGACCGGCTGGCGGCTGGCCAAGCGCATTAGCGCG |
| 334 | NLpep58 (w/o Met) | A.A. | GVTGWRLAKRISA |
| 335 | NLpep59 (w/o Met) | N.A. | GGAGTGACCGGCTGGCGGCTGCAGAAGCGCATTAGCGCG |
| 336 | NLpep59 (w/o Met) | A.A. | GVTGWRLQKRISA |
| 337 | NLpep60 (w/o Met) | N.A. | GGAGTGACCGGCTGGCGGCTGCTGAAGCGCATTAGCGCG |
| 338 | NLpep60 (w/o Met) | A.A. | GVTGWRLLKRISA |
| 339 | NLpep61 (w/o Met) | N.A. | GGAGTGACCGGCTGGCGGCTGAAGAAGCGCATTAGCGCG |
| 340 | NLpep61 (w/o Met) | A.A. | GVTGWRLKKRISA |
| 341 | NLpep62 (w/o Met) | N.A. | AACCACACCGGCTGGCGGCTGAACAAGAAGGTGAGCAAC |
| 342 | NLpep62 (w/o Met) | A.A. | NITGWRLNKKVSN |
| 343 | NLpep63 (w/o Met) | N.A. | AACCACACCGGCTACCGGCTGAACAAGAAGGTGAGCAAC |
| 344 | NLpep63 (w/o Met) | A.A. | NITGYRLNKKVSN |
| 345 | NLpep64 (w/o Met) | N.A. | TGCGTGACCGGCTGGCGGCTGTTCAAGCGCATTAGCGCG |

TABLE 1-continued

Exemplary internal tag and/or structural complement peptide sequences

| SEQ ID NO. | PEPTIDE NO. | POLYMER | SEQUENCE |
|---|---|---|---|
| 346 | NLpep64 (w/o Met) | A.A. | CVTGWRLFKRISA |
| 347 | NLpep65 (w/o Met) | N.A. | CCCGTGACCGGCTGGCGGCTGTTCAAGCGCATTAGCGCG |
| 348 | NLpep65 (w/o Met) | A.A. | PVTGWRLFKRISA |
| 349 | NLpep66 (w/o Met) | N.A. | AACCACACCGGCTACCGGCTGTTCAAGAAGGTGAGCAAC |
| 350 | NLpep66 (w/o Met) | A.A. | NITGYRLFKKVSN |
| 351 | NLpep67 (w/o Met) | N.A. | AACGTGACCGGCTACCGGCTGTTCAAGAAGGTGAGCAAC |
| 352 | NLpep67 (w/o Met) | A.A. | NVTGYRLFKKVSN |
| 353 | NLpep68 (w/o Met) | N.A. | AACGTGACCGGCTGGCGGCTGTTCAAGAAGGTGAGCAAC |
| 354 | NLpep68 (w/o Met) | A.A. | NVTGWRLFKKVSN |
| 355 | NLpep69 (w/o Met) | N.A. | AACGTGACCGGCTGGCGGCTGTTCAAGAAGATTAGCAAC |
| 356 | NLpep69 (w/o Met) | A.A. | NVTGWRLFKKISN |
| 357 | NLpep70 (w/o Met) | N.A. | AACGTGACCGGCTGGCGGCTGTTCAAGCGCATTAGCAAC |
| 358 | NLpep70 (w/o Met) | A.A. | NVTGWRLFKRISN |
| 359 | NLpep71 (w/o Met) | N.A. | GGAGTGACCGGCTGGCGGCTGTTCAAGCGCATTAGCAAC |
| 360 | NLpep71 (w/o Met) | A.A. | GVTGWRLFKRISN |
| 361 | NLpep72 (w/o Met) | N.A. | AACGTGACCGGCTGGCGGCTGTTCGAACGCATTAGCAAC |
| 362 | NLpep72 (w/o Met) | A.A. | NVTGWRLFERISN |
| 363 | NLpep73 (w/o Met) | N.A. | AACGTGACCGGCTGGCGGCTGTTCAAGCGCATTCTGAAC |
| 364 | NLpep73 (w/o Met) | A.A. | NVTGWRLFKRILN |
| 365 | NLpep74 (w/o Met) | N.A. | AACGTGACCGGCTGGCGGCTGTTCAAGCGCATTAGCGCG |
| 366 | NLpep74 (w/o Met) | A.A. | NVTGWRLFKRISA |
| 367 | NLpep75 (w/o Met) | N.A. | AACGTGACCGGCTGGCGGCTGTTCGAAAAGATTAGCAAC |
| 368 | NLpep75 (w/o Met) | A.A. | NVTGWRLFEKISN |
| 369 | NLpep76 (w/o Met) | N.A. | AACGTGAGCGGCTGGCGGCTGTTCGAAAAGATTAGCAAC |
| 370 | NLpep76 (w/o Met) | A.A. | NVSGWRLFEKISN |
| 371 | NLpep77 (w/o Met) | N.A. | GTGACCGGCTGGCGGCTGTTCAAGAAGATTAGCAAC |
| 372 | NLpep77 (w/o Met) | A.A. | VTGWRLFKKISN |
| 373 | NLpep78 (w/o Met) | N.A. | AACGTGAGCGGCTGGCGGCTGTTCAAGAAGATTAGCAAC |
| 374 | NLpep78 (w/o Met) | A.A. | NVSGWRLFKKISN |
| 375 | NLpep79 (w/o Met) | N.A. | AACGTGACCGGCTACCGGCTGTTCAAGAAGATTAGCAAC |
| 376 | NLpep79 (w/o Met) | A.A. | NVTGYRLFKKISN |
| 377 | NLpep80 (w/o Met) | N.A. | GTGAGCGGCTGGCGGCTGTTCAAGAAGATTAGCAAC |
| 378 | NLpep80 (w/o Met) | A.A. | VSGWRLFKKISN |
| 379 | NLpep81 (w/o Met) | N.A. | AGCGGCTGGCGGCTGTTCAAGAAGATTAGCAAC |
| 380 | NLpep81 (w/o Met) | A.A. | SGWRLFKKISN |
| 381 | NLpep82 (w/o Met) | N.A. | GGCTGGCGGCTGTTCAAGAAGATTAGCAAC |
| 382 | NLpep82 (w/o Met) | A.A. | GWRLFKKISN |

TABLE 1-continued

Exemplary internal tag and/or structural complement peptide sequences

| SEQ ID NO. | PEPTIDE NO. | POLYMER | SEQUENCE |
|---|---|---|---|
| 383 | NLpep83 (w/o Met) | N.A. | AACGTGAGCGGCTGGCGGCTGTTCAAGAAGATTAGC |
| 384 | NLpep83 (w/o Met) | A.A. | NVSGWRLFKKIS |
| 385 | NLpep84 (w/o Met) | N.A. | AACGTGAGCGGCTGGCGGCTGTTCAAGAAGATT |
| 386 | NLpep84 (w/o Met) | A.A. | NVSGWRLFKKI |
| 387 | NLpep85 (w/o Met) | N.A. | AACGTGAGCGGCTGGCGGCTGTTCAAGAAG |
| 388 | NLpep85 (w/o Met) | A.A. | NVSGWRLFKK |
| 389 | NLpep86 (w/o Met) | N.A. | GTGAGCGGCTGGCGGCTGTTCAAGAAGATTAGC |
| 390 | NLpep86 (w/o Met) | A.A. | VSGWRLFKKIS |
| 391 | NLpep87 (w/o Met) | N.A. | AGCGGCTGGCGGCTGTTCAAGAAGATT |
| 392 | NLpep87 (w/o Met) | A.A. | SGWRLFKKI |
| 393 | NLpep88 (w/o Met) | N.A. | AACGTGAGCGGCTGGGGCCTGTTCAAGAAGATTAGCAAC |
| 394 | NLpep88 (w/o Met) | A.A. | NVSGWGLFKKISN |
| 395 | NLpep89 (w/o Met) | N.A. | CCCGTGAGCGGCTGGCGGCTGTTCAAGAAGATTAGCAAC |
| 396 | NLpep89 (w/o Met) | A.A. | PVSGWRLFKKISN |
| 397 | NLpep90 (w/o Met) | N.A. | AACCCCGTGAGCGGCTGGCGGCTGTTCAAGAAGATTAGCAAC |
| 398 | NLpep90 (w/o Met) | A.A. | NPVSGWRLFKKISN |
| 399 | NLpep91 (w/o Met) | N.A. | ATCAACCCCGTGAGCGGCTGGCGGCTGTTCAAGAAGATTAGCAAC |
| 400 | NLpep91 (w/o Met) | A.A. | INPVSGWRLFKKISN |
| 401 | NLpep92 (w/o Met) | N.A. | ACCATCAACCCCGTGAGCGGCTGGCGGCTGTTCAAGAAGATTAGCAAC |
| 402 | NLpep92 (w/o Met) | A.A. | TINPVSGWRLFKKISN |
| 403 | NLpep93 (w/o Met) | N.A. | GTGACCATCAACCCCGTGAGCGGCTGGCGGCTGTTCAAGAAGATTAGCAAC |
| 404 | NLpep93 (w/o Met) | A.A. | VTINPVSGWRLFKKISN |
| 405 | NLpep94 (w/o Met) | N.A. | CGGGTGACCATCAACCCCGTGAGCGGCTGGCGGCTGTTCAAGAAGATTAGCAAC |
| 406 | NLpep94 (w/o Met) | A.A. | RVTINPVSGWRLFKKISN |
| 407 | NLpep95 (w/o Met) | N.A. | AGCGGCTGGCGGCTGCTGAAGAAGATT |
| 408 | NLpep95 (w/o Met) | A.A. | SGWRLLKKI |
| 409 | NLpep96 (w/o Met) | N.A. | ACCGGCTACCGGCTGCTGAAGAAGATT |
| 410 | NLpep96 (w/o Met) | A.A. | TGYRLLKKI |
| 411 | NLpep97 (w/o Met) | N.A. | AGCGGCTGGCGGCTGTTCAAGAAG |
| 412 | NLpep97 (w/o Met) | A.A. | SGWRLFKK |
| 413 | NLpep98 (w/o Met) | N.A. | GTGACCGGCTACCGGCTGTTCAAGAAGATTAGC |
| 414 | NLpep98 (w/o Met) | A.A. | VTGYRLFKKIS |
| 415 | NLpep99 (w/o Met) | N.A. | GTGACCGGCTACCGGCTGTTCGAGAAGATTAGC |
| 416 | NLpep99 (w/o Met) | A.A. | VTGYRLFEKIS |
| 417 | NLpep100 (w/o Met) | N.A. | GTGACCGGCTACCGGCTGTTCGAGCAGATTAGC |

TABLE 1-continued

Exemplary internal tag and/or structural complement peptide sequences

| SEQ ID NO. | PEPTIDE NO. | POLY MER | SEQUENCE |
|---|---|---|---|
| 418 | NLpep100 (w/o Met) | A.A. | VTGYRLFEQIS |
| 419 | NLpep101 (w/o Met) | N.A. | GTGACCGGCTACCGGCTGTTCGAGAAGGAGAGC |
| 420 | NLpep101 (w/o Met) | A.A. | VTGYRLFEKES |
| 421 | NLpep102 (w/o Met) | N.A. | GTGACCGGCTACCGGCTGTTCGAGCAGGAGAGC |
| 422 | NLpep102 (w/o Met) | A.A. | VTGYRLFEQES |
| 423 | NLpep103 (w/o Met) | N.A. | GTGACCGGCTACCGGCTGTTCGAGCAGGAGCTG |
| 424 | NLpep103 (w/o Met) | A.A. | VTGYRLFEQEL |
| 425 | NLpep104 (w/o Met) | N.A. | GTGGAGGGCTACCGGCTGTTCGAGAAGATTAGC |
| 426 | NLpep104 (w/o Met) | A.A. | VEGYRLFEKIS |
| 427 | NLpep105 (w/o Met) | N.A. | GTGGAGGGCTACCGGCTGTTCGAGCAGATTAGC |
| 428 | NLpep105 (w/o Met) | A.A. | VEGYRLFEQIS |
| 429 | NLpep106 (w/o Met) | N.A. | GTGGAGGGCTACCGGCTGTTCGAGAAGGAGAGC |
| 430 | NLpep106 (w/o Met) | A.A. | VEGYRLFEKES |
| 431 | NLpep107 (w/o Met) | N.A. | GTGGAGGGCTACCGGCTGTTCGAGCAGGAGAGC |
| 432 | NLpep107 (w/o Met) | A.A. | VEGYRLFEQES |
| 433 | NLpep108 (w/o Met) | N.A. | GTGGAGGGCTACCGGCTGTTCGAGCAGGAGCTG |
| 434 | NLpep108 (w/o Met) | A.A. | VEGYRLFEQEL |
| 435 | NLpep109 (w/o Met) | N.A. | ATTAGCGGCTGGCGGCTGATGAAGAACATTAGC |
| 436 | NLpep109 (w/o Met) | A.A. | ISGWRLMKNIS |
| 437 | NLpep110 (w/o Met) | N.A. | GTGGAGGGCTACCGGCTGTTCAAGAAGATTAGC |
| 438 | NLpep110 (w/o Met) | A.A. | VEGYRLFKKIS |
| 2162 | NLpep111 (w/ Met) | N.A. | ATGGTGACCGGCTACCGGCTGTTCGAGGAGATCAGC |
| 2163 | NLpep111 (w/ Met) | A.A. | MVTGYRLFEEIS |
| 2164 | NLpep112 (w/ Met) | N.A. | ATGGTGACCGGCTACCGGCTGTTCGAGGAGGCCAGC |
| 2165 | NLpep112 (w/ Met) | A.A. | MVTGYRLFEEAS |
| 2166 | NLpep113 (w/ Met) | N.A. | ATGGTGACCGGCTACCGGCTGTTCGAGGAGGAGAGC |
| 2167 | NLpep113 (w/ Met) | A.A. | MVTGYRLFEEES |
| 2168 | NLpep114 (w/ Met) | N.A. | ATGGTGACCGGCTACCGGCTGTTCGAGGAGATCCTG |
| 2169 | NLpep114 (w/ Met) | A.A. | MVTGYRLFEEIL |
| 2170 | NLpep115 (w/ Met) | N.A. | ATGGTGACCGGCTACCGGCTGTTCGAGGAGGCCCTG |
| 2171 | NLpep115 (w/ Met) | A.A. | MVTGYRLFEEAL |
| 2172 | NLpep116 (w/ Met) | N.A. | ATGGTGACCGGCTACCGGCTGTTCGAGGAGGAGCTG |
| 2173 | NLpep116 (w/ Met) | A.A. | MVTGYRLFEEEL |
| 2174 | NLpep117 (w/ Met) | N.A. | ATGGTGGAGGGCTACCGGCTGTTCGAGGAGATCAGC |
| 2175 | NLpep117 (w/ Met) | A.A. | MVEGYRLFEEIS |
| 2176 | NLpep118 (w/ Met) | N.A. | ATGGTGGAGGGCTACCGGCTGTTCGAGGAGGCCAGC |
| 2177 | NLpep118 (w/ Met) | A.A. | MVEGYRLFEEAS |

TABLE 1-continued

Exemplary internal tag and/or structural complement peptide sequences

| SEQ ID NO. | PEPTIDE NO. | POLY MER | SEQUENCE |
|---|---|---|---|
| 2178 | NLpep119 (w/ Met) | N.A. | ATGGTGGAGGGCTACCGGCTGTTCGAGGAGGAGAGC |
| 2179 | NLpep119 (w/ Met) | A.A. | MVEGYRLFEEES |
| 2180 | NLpep120 (w/ Met) | N.A. | ATGGTGGAGGGCTACCGGCTGTTCGAGGAGATCCTG |
| 2181 | NLpep120 (w/ Met) | A.A. | MVEGYRLFEEIL |
| 2182 | NLpep121 (w/ Met) | N.A. | ATGGTGGAGGGCTACCGGCTGTTCGAGGAGGCCCTG |
| 2183 | NLpep121 (w/ Met) | A.A. | MVEGYRLFEEAL |
| 2184 | NLpep122 (w/ Met) | N.A. | ATGGTGGAGGGCTACCGGCTGTTCGAGGAGGAGCTG |
| 2185 | NLpep122 (w/ Met) | A.A. | MVEGYRLFEEEL |
| 2186 | NLpep123 (w/ Met) | N.A. | ATGGTGACCGGCTACCGGCTGTTCAAGAAGATCCTG |
| 2187 | NLpep123 (w/ Met) | A.A. | MVTGYRLFKKIL |
| 2188 | NLpep124 (w/ Met) | N.A. | ATGGTGACCGGCTACCGGCTGATGAAGAAGATCCTG |
| 2189 | NLpep124 (w/ Met) | A.A. | MVTGYRLMKKIL |
| 2190 | NLpep125 (w/ Met) | N.A. | ATGGTGACCGGCTACCGGCTGCACAAGAAGATCCTG |
| 2191 | NLpep125 (w/ Met) | A.A. | MVTGYRLHKKIL |
| 2192 | NLpep126 (w/ Met) | N.A. | ATGGTGACCGGCTACCGGCTGCTGAAGAAGATCCTG |
| 2193 | NLpep126 (w/ Met) | A.A. | MVTGYRLLKKIL |
| 2194 | NLpep127 (w/ Met) | N.A. | ATGGTGACCGGCTACCGGCTGAGCAAGAAGATCCTG |
| 2195 | NLpep127 (w/ Met) | A.A. | MVTGYRLSKKIL |
| 2196 | NLpep128 (w/ Met) | N.A. | ATGGTGACCGGCTACCGGCTGTTCGAGAAGATCCTG |
| 2197 | NLpep128 (w/ Met) | A.A. | MVTGYRLFEKIL |
| 2198 | NLpep129(w/ Met) | N.A. | ATGGTGACCGGCTACCGGCTGATGGAGAAGATCCTG |
| 2199 | NLpep129(w/ Met) | A.A. | MVTGYRLMEKIL |
| 2200 | NLpep130 (w/ Met) | N.A. | ATGGTGACCGGCTACCGGCTGCACGAGAAGATCCTG |
| 2201 | NLpep130 (w/ Met) | A.A. | MVTGYRLHEKIL |
| 2202 | NLpep131 (w/ Met) | N.A. | ATGGTGACCGGCTACCGGCTGCTGGAGAAGATCCTG |
| 2203 | NLpep131 (w/ Met) | A.A. | MVTGYRLLEKIL |
| 2204 | NLpep132 (w/ Met) | N.A. | ATGGTGACCGGCTACCGGCTGAGCGAGAAGATCCTG |
| 2205 | NLpep132 (w/ Met) | A.A. | MVTGYRLSEKIL |
| 2206 | NLpep133 (w/ Met) | N.A. | ATGGTGACCGGCTACCGGCTGATGGAGGAGATCCTG |
| 2207 | NLpep133 (w/ Met) | A.A. | MVTGYRLMEEIL |
| 2208 | NLpep134(w/ Met) | N.A. | ATGGTGACCGGCTACCGGCTGCACGAGGAGATCCTG |
| 2209 | NLpep134(w/ Met) | A.A. | MVTGYRLHEEIL |
| 2210 | NLpep135 (w/ Met) | N.A. | ATGGTGACCGGCTACCGGCTGCTGGAGGAGATCCTG |
| 2211 | NLpep135 (w/ Met) | A.A. | MVTGYRLLEEIL |
| 2212 | NLpep136 (w/ Met) | N.A. | ATGGTGACCGGCTACCGGCTGAGCGAGGAGATCCTG |
| 2213 | NLpep136 (w/ Met) | A.A. | MVTGYRLSEEIL |
| 2214 | NLpep137(w/ Met) | N.A. | ATGGTGAGCGGCTACCGGCTGTTCGAGGAGATCCTG |

TABLE 1-continued

Exemplary internal tag and/or structural complement peptide sequences

| SEQ ID NO. | PEPTIDE NO. | POLYMER | SEQUENCE |
|---|---|---|---|
| 2215 | NLpep137(w/ Met) | A.A. | MVSGYRLFEEIL |
| 2216 | NLpep138(w/ Met) | N.A. | ATGGTGACCGGCTGGCGGCTGTTCGAGGAGATCCTG |
| 2217 | NLpep138(w/ Met) | A.A. | MVTGWRLFEEIL |
| 2218 | NLpep139 (w/ Met) | N.A. | ATGGTGAGCGGCTGGCGGCTGTTCGAGGAGATCCTG |
| 2219 | NLpep139 (w/ Met) | A.A. | MVSGWRLFEEIL |
| 2220 | NLpep140 (w/ Met) | N.A. | ATGAACGTGACCGGCTACCGGCTGTTCGAGGAGATCCTG |
| 2221 | NLpep140 (w/ Met) | A.A. | MNVTGYRLFEEIL |
| 2222 | NLpep141 (w/ Met) | N.A. | ATGGTGACCGGCTACCGGCTGTTCGAGGAGATCCTGAAC |
| 2223 | NLpep141 (w/ Met) | A.A. | MVTGYRLFEEILN |
| 2224 | NLpep142 (w/ Met) | N.A. | ATGAACGTGACCGGCTACCGGCTGTTCGAGGAGATCCTGAAC |
| 2225 | NLpep142 (w/ Met) | A.A. | MNVTGYRLFEEILN |
| 2226 | NLpep143 (w/ Met) | N.A. | ATGGTGACCGGCTACCGGCTGTTCGAGGAGATC |
| 2227 | NLpep143 (w/ Met) | A.A. | MVTGYRLFEEI |
| 2228 | NLpep144 (w/ Met) | N.A. | ATGGTGACCGGCTACCGGCTGTTCCAGAAGATCAGC |
| 2229 | NLpep144 (w/ Met) | A.A. | MVTGYRLFQKIS |
| 2230 | NLpep145 (w/ Met) | N.A. | ATGGTGACCGGCTACCGGCTGTTCAAGAAGATCAGCAAC |
| 2231 | NLpep145 (w/ Met) | A.A. | MVTGYRLFKKISN |
| 2232 | NLpep146 (w/ Met) | N.A. | ATGGTGACCGGCTACCGGCTGTTCAAGAAGATCAGC |
| 2233 | NLpep146 (w/ Met) | A.A. | MVTGYRLFKKIS |
| 2234 | NLpep147 (w/ Met) | A.A. | MVSGWRLFKKISA |
| 2235 | NLpep148 (w/ Met) | A.A. | MGVSGWRLFKKIS |
| 2236 | NLpep149 (w/ Met) | A.A. | MSVSGWRLFKKISN |
| 2237 | NLpep150 (w/ Met) | A.A. | MSVSGWRLFKKISA |
| 2238 | NLpep151 (w/ Met) | A.A. | MNSVSGWRLFKKISA |
| 2239 | NLpep152 (w/ Met) | A.A. | MNSVSGWRLFKKISN |
| 2240 | NLpep153 (w/ Met) | A.A. | MSNVSGWRLFKKIS |
| 2241 | NLpep154 (w/ Met) | A.A. | MSGVSGWRLFKKIS |
| 2242 | NLpep155 (w/ Met) | A.A. | MNSNVSGWRLFKKIS |
| 2243 | NLpep156 (w/ Met) | A.A. | MNSGVSGWRLFKKIS |
| 2244 | NLpep157 (w/ Met) | A.A. | MSVSGWRLFKKIS |
| 2245 | NLpep158 (w/ Met) | A.A. | MNSVSGWRLFKKIS |
| 2246 | NLpep159 (w/ Met) | A.A. | MSNVSGWRLFKKISN |
| 2247 | NLpep160 (w/ Met) | A.A. | MNSNVSGWRLFKKISN |
| 2248 | NLpep161 (w/ Met) | A.A. | MGWRLFKK |
| 2249 | NLpep162(w/ Met) | A.A. | MGWALFKK |
| 2250 | NLpep163 (w/ Met) | A.A. | MVTGWALFEEIL |
| 2251 | NLpep164 (w/ Met) | A.A. | MVTGYALFQEIL |

TABLE 1-continued

Exemplary internal tag and/or structural complement peptide sequences

| SEQ ID NO. | PEPTIDE NO. | POLYMER | SEQUENCE |
|---|---|---|---|
| 2252 | NLpep165 (w/ Met) | A.A. | MVTGYALFEQIL |
| 2253 | NLpep166 (w/ Met) | A.A. | MVTGYALFEEIL |
| 2254 | NLpep167 (w/ Met) | N.A. | ATGGTGTCCGGCTGGGCACTGTTCAAGAAAATTTCC |
| 2255 | NLpep167 (w/ Met) | A.A. | MVSGWALFKKIS |
| 2256 | NLpep168 (w/ Met) | A.A. | MVSGWKLFKKIS |
| 2257 | NLpep169 (w/ Met) | N.A. | ATGGTGTCCGGCTGGCAGCTGTTCAAGAAAATTTCC |
| 2258 | NLpep169 (w/ Met) | A.A. | MVSGWQLFKKIS |
| 2259 | NLpep170 (w/ Met) | A.A. | MVSGWELFKKIS |
| 2260 | NLpep171 (w/ Met) | N.A. | ATGGTGTCCGGCTGGCTGCTGTTCAAGAAAATTTCC |
| 2261 | NLpep171 (w/ Met) | A.A. | MVSGWLLFKKIS |
| 2262 | NLpep172 (w/ Met) | N.A. | ATGGTGTCCGGCTGGGTGCTGTTCAAGAAAATTTCC |
| 2263 | NLpep172 (w/ Met) | A.A. | MVSGWVLFKKIS |
| 2264 | NLpep111 (w/o Met) | N.A. | GTGACCGGCTACCGGCTGTTCGAGGAGATCAGC |
| 2265 | NLpep111 (w/o Met) | A.A. | VTGYRLFEEIS |
| 2266 | NLpep112 (w/o Met) | N.A. | GTGACCGGCTACCGGCTGTTCGAGGAGGCCAGC |
| 2267 | NLpep112 (w/o Met) | A.A. | VTGYRLFEEAS |
| 2268 | NLpep113 (w/o Met) | N.A. | GTGACCGGCTACCGGCTGTTCGAGGAGGAGAGC |
| 2269 | NLpep113 (w/o Met) | A.A. | VTGYRLFEEES |
| 2270 | NLpep114 (w/o Met) | N.A. | GTGACCGGCTACCGGCTGTTCGAGGAGATCCTG |
| 2271 | NLpep114 (w/o Met) | A.A. | VTGYRLFEEIL |
| 2272 | NLpep115 (w/o Met) | N.A. | GTGACCGGCTACCGGCTGTTCGAGGAGGCCCTG |
| 2273 | NLpep115 (w/o Met) | A.A. | VTGYRLFEEAL |
| 2274 | NLpep116 (w/o Met) | N.A. | GTGACCGGCTACCGGCTGTTCGAGGAGGAGCTG |
| 2275 | NLpep116 (w/o Met) | A.A. | VTGYRLFEEEL |
| 2276 | NLpep117 (w/o Met) | N.A. | GTGGAGGGCTACCGGCTGTTCGAGGAGATCAGC |
| 2277 | NLpep117 (w/o Met) | A.A. | VEGYRLFEEIS |
| 2278 | NLpep118 (w/o Met) | N.A. | GTGGAGGGCTACCGGCTGTTCGAGGAGGCCAGC |
| 2279 | NLpep118 (w/o Met) | A.A. | VEGYRLFEEAS |
| 2280 | NLpep119 (w/o Met) | N.A. | GTGGAGGGCTACCGGCTGTTCGAGGAGGAGAGC |
| 2281 | NLpep119 (w/o Met) | A.A. | VEGYRLFEEES |
| 2282 | NLpep120 (w/o Met) | N.A. | GTGGAGGGCTACCGGCTGTTCGAGGAGATCCTG |
| 2283 | NLpep120 (w/o Met) | A.A. | VEGYRLFEEIL |
| 2284 | NLpep121 (w/o Met) | N.A. | GTGGAGGGCTACCGGCTGTTCGAGGAGGCCCTG |
| 2285 | NLpep121 (w/o Met) | A.A. | VEGYRLFEEAL |
| 2286 | NLpep122 (w/o Met) | N.A. | GTGGAGGGCTACCGGCTGTTCGAGGAGGAGCTG |
| 2287 | NLpep122 (w/o Met) | A.A. | VEGYRLFEEEL |
| 2288 | NLpep123 (w/o Met) | N.A. | GTGACCGGCTACCGGCTGTTCAAGAAGATCCTG |

TABLE 1-continued

Exemplary internal tag and/or structural complement peptide sequences

| SEQ ID NO. | PEPTIDE NO. | POLYMER | SEQUENCE |
|---|---|---|---|
| 2289 | NLpep123 (w/o Met) | A.A. | VTGYRLFKKIL |
| 2290 | NLpep124 (w/o Met) | N.A. | GTGACCGGCTACCGGCTGATGAAGAAGATCCTG |
| 2291 | NLpep124 (w/o Met) | A.A. | VTGYRLMKKIL |
| 2292 | NLpep125 (w/o Met) | N.A. | GTGACCGGCTACCGGCTGCACAAGAAGATCCTG |
| 2293 | NLpep125 (w/o Met) | A.A. | VTGYRLHKKIL |
| 2294 | NLpep126 (w/o Met) | N.A. | GTGACCGGCTACCGGCTGCTGAAGAAGATCCTG |
| 2295 | NLpep126 (w/o Met) | A.A. | VTGYRLLKKIL |
| 2296 | NLpep127 (w/o Met) | N.A. | GTGACCGGCTACCGGCTGAGCAAGAAGATCCTG |
| 2297 | NLpep127 (w/o Met) | A.A. | VTGYRLSKKIL |
| 2298 | NLpep128 (w/o Met) | N.A. | GTGACCGGCTACCGGCTGTTCGAGAAGATCCTG |
| 2299 | NLpep128 (w/o Met) | A.A. | VTGYRLFEKIL |
| 2300 | NLpep129 (w/o Met) | N.A. | GTGACCGGCTACCGGCTGATGGAGAAGATCCTG |
| 2301 | NLpep129 (w/o Met) | A.A. | VTGYRLMEKIL |
| 2302 | NLpep130 (w/o Met) | N.A. | GTGACCGGCTACCGGCTGCACGAGAAGATCCTG |
| 2303 | NLpep130 (w/o Met) | A.A. | VTGYRLHEKIL |
| 2304 | NLpep131 (w/o Met) | N.A. | GTGACCGGCTACCGGCTGCTGGAGAAGATCCTG |
| 2305 | NLpep131 (w/o Met) | A.A. | VTGYRLLEKIL |
| 2306 | NLpep132 (w/o Met) | N.A. | GTGACCGGCTACCGGCTGAGCGAGAAGATCCTG |
| 2307 | NLpep132 (w/o Met) | A.A. | VTGYRLSEKIL |
| 2308 | NLpep133 (w/o Met) | N.A. | GTGACCGGCTACCGGCTGATGGAGGAGATCCTG |
| 2309 | NLpep133 (w/o Met) | A.A. | VTGYRLMEEIL |
| 2310 | NLpep134 (w/o Met) | N.A. | GTGACCGGCTACCGGCTGCACGAGGAGATCCTG |
| 2311 | NLpep134 (w/o Met) | A.A. | VTGYRLHEEIL |
| 2312 | NLpep135 (w/o Met) | N.A. | GTGACCGGCTACCGGCTGCTGGAGGAGATCCTG |
| 2313 | NLpep135 (w/o Met) | A.A. | VTGYRLLEEIL |
| 2314 | NLpep136 (w/o Met) | N.A. | GTGACCGGCTACCGGCTGAGCGAGGAGATCCTG |
| 2315 | NLpep136 (w/o Met) | A.A. | VTGYRLSEEIL |
| 2316 | NLpep137 (w/o Met) | N.A. | GTGAGCGGCTACCGGCTGTTCGAGGAGATCCTG |
| 2317 | NLpep137 (w/o Met) | A.A. | VSGYRLFEEIL |
| 2318 | NLpep138 (w/o Met) | N.A. | GTGACCGGCTGGCGGCTGTTCGAGGAGATCCTG |
| 2319 | NLpep138 (w/o Met) | A.A. | VTGWRLFEEIL |
| 2320 | NLpep139 (w/o Met) | N.A. | GTGAGCGGCTGGCGGCTGTTCGAGGAGATCCTG |
| 2321 | NLpep139 (w/o Met) | A.A. | VSGWRLFEEIL |
| 2322 | NLpep140 (w/o Met) | N.A. | AACGTGACCGGCTACCGGCTGTTCGAGGAGATCCTG |
| 2323 | NLpep140 (w/o Met) | A.A. | NVTGYRLFEEIL |
| 2324 | NLpep141 (w/o Met) | N.A. | GTGACCGGCTACCGGCTGTTCGAGGAGATCCTGAAC |
| 2325 | NLpep141 (w/o Met) | A.A. | VTGYRLFEEILN |

TABLE 1-continued

Exemplary internal tag and/or structural complement peptide sequences

| SEQ ID NO. | PEPTIDE NO. | POLYMER | SEQUENCE |
|---|---|---|---|
| 2326 | NLpep142 (w/o Met) | N.A. | AACGTGACCGGCTACCGGCTGTTCGAGGAGATCCTGAAC |
| 2327 | NLpep142 (w/o Met) | A.A. | NVTGYRLFEEILN |
| 2328 | NLpep143 (w/o Met) | N.A. | GTGACCGGCTACCGGCTGTTCGAGGAGATC |
| 2329 | NLpep143 (w/o Met) | A.A. | VTGYRLFEEI |
| 2330 | NLpep144 (w/o Met) | N.A. | GTGACCGGCTACCGGCTGTTCCAGAAGATCAGC |
| 2331 | NLpep144 (w/o Met) | A.A. | VTGYRLFQKIS |
| 2332 | NLpep145 (w/o Met) | N.A. | GTGACCGGCTACCGGCTGTTCAAGAAGATCAGCAAC |
| 2333 | NLpep145 (w/o Met) | A.A. | VTGYRLFKKISN |
| 2334 | NLpep146 (w/o Met) | N.A. | GTGACCGGCTACCGGCTGTTCAAGAAGATCAGC |
| 2335 | NLpep146 (w/o Met) | A.A. | VTGYRLFKKIS |
| 2336 | NLpep147 (w/o Met) | A.A. | VSGWRLFKKISA |
| 2337 | NLpep148 (w/o Met) | A.A. | GVSGWRLFKKIS |
| 2338 | NLpep149 (w/o Met) | A.A. | SVSGWRLFKKISN |
| 2339 | NLpep150 (w/o Met) | A.A. | SVSGWRLFKKISA |
| 2340 | NLpep151 (w/o Met) | A.A. | NSVSGWRLFKKISA |
| 2341 | NLpep152 (w/o Met) | A.A. | NSVSGWRLFKKISN |
| 2342 | NLpep153 (w/o Met) | A.A. | SNVSGWRLFKKIS |
| 2343 | NLpep154 (w/o Met) | A.A. | SGVSGWRLFKKIS |
| 2344 | NLpep155 (w/o Met) | A.A. | NSNVSGWRLFKKIS |
| 2345 | NLpep156 (w/o Met) | A.A. | NSGVSGWRLFKKIS |
| 2346 | NLpep157 (w/o Met) | A.A. | SVSGWRLFKKIS |
| 2347 | NLpep158 (w/o Met) | A.A. | NSVSGWRLFKKIS |
| 2348 | NLpep159 (w/o Met) | A.A. | SNVSGWRLFKKISN |
| 2349 | NLpep160 (w/o Met) | A.A. | NSNVSGWRLFKKISN |
| 2350 | NLpep161 (w/o Met) | A.A. | GWRLFKK |
| 2351 | NLpep162 (w/o Met) | A.A. | GWALFKK |
| 2352 | NLpep163 (w/o Met) | A.A. | VTGWALFEEIL |
| 2353 | NLpep164 (w/o Met) | A.A. | VTGYALFQEIL |
| 2354 | NLpep165 (w/o Met) | A.A. | VTGYALFEQIL |
| 2355 | NLpep166 (w/o Met) | A.A. | VTGYALFEEIL |
| 2356 | NLpep167 (w/o Met) | N.A. | GTGTCCGGCTGGGCACTGTTCAAGAAAATTTCC |
| 2357 | NLpep167 (w/o Met) | A.A. | VSGWALFKKIS |
| 2358 | NLpep168 (w/o Met) | A.A. | VSGWKLFKKIS |
| 2359 | NLpep169 (w/o Met) | N.A. | GTGTCCGGCTGGCAGCTGTTCAAGAAAATTTCC |
| 2360 | NLpep169 (w/o Met) | A.A. | VSGWQLFKKIS |
| 2361 | NLpep170 (w/o Met) | A.A. | VSGWELFKKIS |
| 2362 | NLpep171 (w/o Met) | N.A. | GTGTCCGGCTGGCTGCTGTTCAAGAAAATTTCC |

TABLE 1-continued

Exemplary internal tag and/or structural complement peptide sequences

| SEQ ID NO. | PEPTIDE NO. | POLYMER | SEQUENCE |
|---|---|---|---|
| 2363 | NLpep171 (w/o Met) | A.A. | VSGWLLFKKIS |
| 2364 | NLpep172(w/o Met) | N.A. | GTGTCCGGCTGGGTGCTGTTCAAGAAAATTTCC |
| 2365 | NLpep172(w/o Met) | A.A. | VSGWVLFKKIS |

In certain embodiments, a peptide from Table 1 is provided (e.g., as an internal tag or a structural complement of an internal tag). In some embodiments, an internal tag or a structural complement comprise a single amino acid difference from GVTGWRLCKRILA (SEQ ID NO: 2) and/or any of the peptides listed in Table 1. In some embodiments, an internal tag or a structural complement comprises two or more (e.g., 2, 3, 4, 5, 6, 7, 8, 9, 10, etc.) amino acid differences from GVTGWRLCKRILA (SEQ ID NO: 2) and/or any of the peptides listed in Table 1. In some embodiments, an internal tag or a structural complement is provided comprising one of the amino acid sequences of SEQ ID NOS: 3-438 and 2162-2365. In some embodiments, an internal tag or a structural complement is provided comprising one of the amino acid sequences of SEQ ID NOS: 3-438 and 2162-2365 with one or more additions, substitutions, and/or deletions. In some embodiments, an internal tag, a structural complement, or a portion thereof comprises greater than 70% sequence identity (e.g., 71%, 75%, 80%, 85%, 90%, 95%, 99%) with one or more of the amino acid sequences of SEQ ID NOS: 3-438 and 2162-2365. In some embodiments, nucleic acids are provided comprising one of the nucleic acid coding sequences of SEQ ID NOS: 3-438 and 2162-2365. In some embodiments, nucleic acids are provided comprising one of the nucleic acid sequences of SEQ ID NOS: 3-438 and 2162-2365 with one or more additions, substitutions, and/or deletions. In some embodiments, a nucleic acid or a portion thereof comprises greater than 70% sequence identity (e.g., 71%, 75%, 80%, 85%, 90%, 95%, 99%) with one or more of the nucleic acid sequence of SEQ ID NOS: 3-438 and 2162-2365. In some embodiments, nucleic acids are provided that code for one of the amino acid sequences of SEQ ID NOS: 3-438 and 2162-2365. In some embodiments, nucleic acids are provided that code for one of the amino acid sequences of SEQ ID NOS: 3-438 and 2162-2365 with one or more additions, substitutions, and/or deletions. In some embodiments, a nucleic acid is provided that codes for an amino acid with greater than 70% sequence identity (e.g., 71%, 75%, 80%, 85%, 90%, 95%, 99%) with one or more of the amino acid sequences of SEQ ID NOS: 3-438 and 2162-2365.

In certain embodiments, a nucleic acid from Table 1 is provided. In some embodiments, a nucleic acid encoding a peptide from Table 1 is provided. In some embodiments, a nucleic acid encoding a peptide from Table 1 inserted into another polypeptide sequence is provided. In some embodiments, a nucleic acid of the present invention codes for a peptide that comprises a single amino acid difference from MGVTGWRLCERILA (SEQ ID NO: 2) and/or any of the peptides listed in Table 1 (e.g., inserted into a polypeptide sequence). In some embodiments, nucleic acids code for peptides comprising two or more (e.g., 2, 3, 4, 5, 6, 7, 8, 9, 10, etc.) amino acid differences from MGVTGWRLCERILA (SEQ ID NO: 2) and/or any of the peptides listed in Table 1 (e.g., inserted into a polypeptide sequence). In some embodiments, nucleic acids are provided comprising the sequence of one of the nucleic acids in Table 1 (e.g., inserted into a polypeptide sequence). In some embodiments, nucleic acids are provided comprising one of the nucleic acids of Table 1 with one or more additions, substitutions, and/or deletions. In some embodiments, a nucleic acid or a portion thereof comprises greater than 70% sequence identity (e.g., 71%, 75%, 80%, 85%, 90%, 95%, 99%) with one or more of the nucleic acids of Table 1 (e.g., inserted into a polypeptide sequence).

In some embodiments, internal tags and/or a structural complements of an internal tag that find use in embodiments described herein include polypeptides with one or more amino acid substitutions, deletions, or additions from SEQ ID NO: 440. In some embodiments provided herein is an internal tag or a structural complement of an internal tag comprising an amino acid sequence of Table 2, and/or nucleic acids comprising the nucleic acid sequences of Table 2.

TABLE 2

Exemplary internal tag and/or structural complement polypeptide sequences

| SEQ ID NO | Polymer | ID | SEQ ID NO | Poly. | ID | SEQ ID NO | Poly. | ID |
|---|---|---|---|---|---|---|---|---|
| 441 | N.A. | R11N | 727 | N.A. | 5A2 + V58P | 1013 | N.A. | 5P D6 (−152-157) |
| 442 | A.A | R11N | 728 | A.A | 5A2 + V58P | 1014 | A.A | 5P D6 (−152-157) |
| 443 | N.A. | T13I | 729 | N.A. | 5A2 + V58Q | 1015 | N.A. | 5P D7 (−151-157) |
| 444 | A.A | T13I | 730 | A.A | 5A2 + V58Q | 1016 | A.A | 5P D7 (−151-157) |
| 445 | N.A. | G15S | 731 | N.A. | 5A2 + V58R | 1017 | N.A. | 5P + F31A |
| 446 | A.A | G15S | 732 | A.A | 5A2 + V58R | 1018 | A.A | 5P + F31A |
| 447 | N.A. | L18Q | 733 | N.A. | 5A2 + V58S | 1019 | N.A. | 5P + F31C |
| 448 | A.A | L18Q | 734 | A.A | 5A2 + V58S | 1020 | A.A | 5P + F31C |
| 449 | N.A. | Q20K | 735 | N.A. | 5A2 + V58T | 1021 | N.A. | 5P + F31D |
| 450 | A.A | Q20K | 736 | A.A | 5A2 + V58T | 1022 | A.A | 5P + F31D |

TABLE 2-continued

Exemplary internal tag and/or structural complement polypeptide sequences

| SEQ ID NO | Polymer | ID | SEQ ID NO | Poly. | ID | SEQ ID NO | Poly. | ID |
|---|---|---|---|---|---|---|---|---|
| 451 | N.A. | V27M | 737 | N.A. | 5A2 + V58W | 1023 | N.A. | 5P + F31E |
| 452 | A.A | V27M | 738 | A.A | 5A2 + V58W | 1024 | A.A | 5P + F31E |
| 453 | N.A. | F31I | 739 | N.A. | 5A2 + V58Y | 1025 | N.A. | 5P + F31G |
| 454 | A.A | F31I | 740 | A.A | 5A2 + V58Y | 1026 | A.A | 5P + F31G |
| 455 | N.A. | F31L | 741 | N.A. | 5A2 + A67C | 1027 | N.A. | 5P + F31H |
| 456 | A.A | F31L | 742 | A.A | 5A2 + A67C | 1028 | A.A | 5P + F31H |
| 457 | N.A. | F31V | 743 | N.A. | 5A2 + A67D | 1029 | N.A. | 5P + F31I |
| 458 | A.A | F31V | 744 | A.A | 5A2 + A67D | 1030 | A.A | 5P + F31I |
| 459 | N.A. | Q32R | 745 | N.A. | 5A2 + A67E | 1031 | N.A. | 5P + F31K |
| 460 | A.A | Q32R | 746 | A.A | 5A2 + A67E | 1032 | A.A | 5P + F31K |
| 461 | N.A. | N33K | 747 | N.A. | 5A2 + A67F | 1033 | N.A. | 5P + F31L |
| 462 | A.A | N33K | 748 | A.A | 5A2 + A67F | 1034 | A.A | 5P + F31L |
| 463 | N.A. | N33R | 749 | N.A. | 5A2 + A67G | 1035 | N.A. | 5P + F31M |
| 464 | A.A | N33R | 750 | A.A | 5A2 + A67G | 1036 | A.A | 5P + F31M |
| 465 | N.A. | I56N | 751 | N.A. | 5A2 + A67H | 1037 | N.A. | 5P + F31N |
| 466 | A.A | I56N | 752 | A.A | 5A2 + A67H | 1038 | A.A | 5P + F31N |
| 467 | N.A. | V58A | 753 | N.A. | 5A2 + A67I | 1039 | N.A. | 5P + F31P |
| 468 | A.A | V58A | 754 | A.A | 5A2 + A67I | 1040 | A.A | 5P + F31P |
| 469 | N.A. | I59T | 755 | N.A. | 5A2 + A67K | 1041 | N.A. | 5P + F31Q |
| 470 | A.A | I59T | 756 | A.A | 5A2 + A67K | 1042 | A.A | 5P + F31Q |
| 471 | N.A. | G67S | 757 | N.A. | 5A2 + A67L | 1043 | N.A. | 5P + F31R |
| 472 | A.A | G67S | 758 | A.A | 5A2 + A67L | 1044 | A.A | 5P + F31R |
| 473 | N.A. | G67D | 759 | N.A. | 5A2 + A67M | 1045 | N.A. | 5P + F31S |
| 474 | A.A | G67D | 760 | A.A | 5A2 + A67M | 1046 | A.A | 5P + F31S |
| 475 | N.A. | K75E | 761 | N.A. | 5A2 + A67N | 1047 | N.A. | 5P + F31T |
| 476 | A.A | K75E | 762 | A.A | 5A2 + A67N | 1048 | A.A | 5P + F31T |
| 477 | N.A. | M106V | 763 | N.A. | 5A2 + A67P | 1049 | N.A. | 5P + F31V |
| 478 | A.A | M106V | 764 | A.A | 5A2 + A67P | 1050 | A.A | 5P + F31V |
| 479 | N.A. | M106I | 765 | N.A. | 5A2 + A67Q | 1051 | N.A. | 5P + F31W |
| 480 | A.A | M106I | 766 | A.A | 5A2 + A67Q | 1052 | A.A | 5P + F31W |
| 481 | N.A. | D108N | 767 | N.A. | 5A2 + A67R | 1053 | N.A. | 5P + F31Y |
| 482 | A.A | D108N | 768 | A.A | 5A2 + A67R | 1054 | A.A | 5P + F31Y |
| 483 | N.A. | R112Q | 769 | N.A. | 5A2 + A67S | 1055 | N.A. | 5P + L46A |
| 484 | A.A | R112Q | 770 | A.A | 5A2 + A67S | 1056 | A.A | 5P + L46A |
| 485 | N.A. | N144T | 771 | N.A. | 5A2 + A67T | 1057 | N.A. | 5P + L46C |
| 486 | A.A | N144T | 772 | A.A | 5A2 + A67T | 1058 | A.A | 5P + L46C |
| 487 | N.A. | L149M | 773 | N.A. | 5A2 + A67V | 1059 | N.A. | 5P + L46D |
| 488 | A.A | L149M | 774 | A.A | 5A2 + A67V | 1060 | A.A | 5P + L46D |
| 489 | N.A. | N156D | 775 | N.A. | 5A2 + A67W | 1061 | N.A. | 5P + L46E |
| 490 | A.A | N156D | 776 | A.A | 5A2 + A67W | 1062 | A.A | 5P + L46E |
| 491 | N.A. | N156S | 777 | N.A. | 5A2 + A67Y | 1063 | N.A. | 5P + L46F |
| 492 | A.A | N156S | 778 | A.A | 5A2 + A67Y | 1064 | A.A | 5P + L46F |
| 493 | N.A. | V157D | 779 | N.A. | 5A2 + M106A | 1065 | N.A. | 5P + L46G |
| 494 | A.A | V157D | 780 | A.A | 5A2 + M106A | 1066 | A.A | 5P + L46G |
| 495 | N.A. | V157S | 781 | N.A. | 5A2 + M106C | 1067 | N.A. | 5P + L46H |
| 496 | A.A | V157S | 782 | A.A | 5A2 + M106C | 1068 | A.A | 5P + L46H |
| 497 | N.A. | G8A | 783 | N.A. | 5A2 + M106D | 1069 | N.A. | 5P + L46I |
| 498 | A.A | G8A | 784 | A.A | 5A2 + M106D | 1070 | A.A | 5P + L46I |
| 499 | N.A. | G15A | 785 | N.A. | 5A2 + M106E | 1071 | N.A. | 5P + L46K |
| 500 | A.A | G15A | 786 | A.A | 5A2 + M106E | 1072 | A.A | 5P + L46K |
| 501 | N.A. | G25A | 787 | N.A. | 5A2 + M106F | 1073 | N.A. | 5P + L46M |
| 502 | A.A | G25A | 788 | A.A | 5A2 + M106F | 1074 | A.A | 5P + L46M |
| 503 | N.A. | G26A | 789 | N.A. | 5A2 + M106G | 1075 | N.A. | 5P + L46N |
| 504 | A.A | G26A | 790 | A.A | 5A2 + M106G | 1076 | A.A | 5P + L46N |
| 505 | N.A. | G35A | 791 | N.A. | 5A2 + M106H | 1077 | N.A. | 5P + L46P |
| 506 | A.A | G35A | 792 | A.A | 5A2 + M106H | 1078 | A.A | 5P + L46P |
| 507 | N.A. | G48A | 793 | N.A. | 5A2 + M106I | 1079 | N.A. | 5P + L46Q |
| 508 | A.A | G48A | 794 | A.A | 5A2 + M106I | 1080 | A.A | 5P + L46Q |
| 509 | N.A. | G51A | 795 | N.A. | 5A2 + M106K | 1081 | N.A. | 5P + L46R |
| 510 | A.A | G51A | 796 | A.A | 5A2 + M106K | 1082 | A.A | 5P + L46R |
| 511 | N.A. | G64A | 797 | N.A. | 5A2 + M106L | 1083 | N.A. | 5P + L46S |
| 512 | A.A | G64A | 798 | A.A | 5A2 + M106L | 1084 | A.A | 5P + L46S |
| 513 | N.A. | G67A | 799 | N.A. | 5A2 + M106N | 1085 | N.A. | 5P + L46T |
| 514 | A.A | G67A | 800 | A.A | 5A2 + M106N | 1086 | A.A | 5P + L46T |
| 515 | N.A. | G71A | 801 | N.A. | 5A2 + M106P | 1087 | N.A. | 5P + L46V |
| 516 | A.A | G71A | 802 | A.A | 5A2 + M106P | 1088 | A.A | 5P + L46V |
| 517 | N.A. | G95A | 803 | N.A. | 5A2 + M106Q | 1089 | N.A. | 5P + L46W |
| 518 | A.A | G95A | 804 | A.A | 5A2 + M106Q | 1090 | A.A | 5P + L46W |
| 519 | N.A. | G101A | 805 | N.A. | 5A2 + M106R | 1091 | N.A. | 5P + L46Y |
| 520 | A.A | G101A | 806 | A.A | 5A2 + M106R | 1092 | A.A | 5P + L46Y |
| 521 | N.A. | G111A | 807 | N.A. | 5A2 + M106S | 1093 | N.A. | 5P + N108A |
| 522 | A.A | G111A | 808 | A.A | 5A2 + M106S | 1094 | A.A | 5P + N108A |
| 523 | N.A. | G116A | 809 | N.A. | 5A2 + M106T | 1095 | N.A. | 5P + N108C |
| 524 | A.A | G116A | 810 | A.A | 5A2 + M106T | 1096 | A.A | 5P + N108C |

TABLE 2-continued

Exemplary internal tag and/or structural complement polypeptide sequences

| SEQ ID NO | Polymer | ID | SEQ ID NO | Poly. | ID | SEQ ID NO | Poly. | ID |
|---|---|---|---|---|---|---|---|---|
| 525 | N.A. | G122A | 811 | N.A. | 5A2 + M106V | 1097 | N.A. | 5P + N108D |
| 526 | A.A | G122A | 812 | A.A | 5A2 + M106V | 1098 | A.A | 5P + N108D |
| 527 | N.A. | G129A | 813 | N.A. | 5A2 + M106W | 1099 | N.A. | 5P + N108E |
| 528 | A.A | G129A | 814 | A.A | 5A2 + M106W | 1100 | A.A | 5P + N108E |
| 529 | N.A. | G134A | 815 | N.A. | 5A2 + M106Y | 1101 | N.A. | 5P + N108F |
| 530 | A.A | G134A | 816 | A.A | 5A2 + M106Y | 1102 | A.A | 5P + N108F |
| 531 | N.A. | G147A | 817 | N.A. | 5A2 + L149A | 1103 | N.A. | 5P + N108G |
| 532 | A.A | G147A | 818 | A.A | 5A2 + L149A | 1104 | A.A | 5P + N108G |
| 533 | N.A. | I54A | 819 | N.A. | 5A2 + L149C | 1105 | N.A. | 5P + N108H |
| 534 | A.A | I54A | 820 | A.A | 5A2 + L149C | 1106 | A.A | 5P + N108H |
| 535 | N.A. | 5A1 (G15A/D19A/ G35A/G51A/G67A) | 821 | N.A. | 5A2 + L149D | 1107 | N.A. | 5P + N108I |
| 536 | A.A | 5A1 (G15A/D19A/ G35A/G51A/G67A) | 822 | A.A | 5A2 + L149D | 1108 | A.A | 5P + N108I |
| 537 | N.A. | 4A1 (G15A/G35A/ G67A/G71A) | 823 | N.A. | 5A2 + L149E | 1109 | N.A. | 5P + N108K |
| 538 | A.A | 4A1 (G15A/G35A/ G67A/G71A) | 824 | A.A | 5A2 + L149E | 1110 | A.A | 5P + N108K |
| 539 | N.A. | 5A2 (G15A/G35A/ G51A/G67A/G71A) | 825 | N.A. | 5A2 + L149F | 1111 | N.A. | 5P + N108L |
| 540 | A.A | 5A2 (G15A/G35A/ G51A/G67A/G71A) | 826 | A.A | 5A2 + L149F | 1112 | A.A | 5P + N108L |
| 541 | N.A. | 5A2 + A15G | 827 | N.A. | 5A2 + L149G | 1113 | N.A. | 5P + N108M |
| 542 | A.A | 5A2 + A15G | 828 | A.A | 5A2 + L149G | 1114 | A.A | 5P + N108M |
| 543 | N.A. | 5A2 + A35G | 829 | N.A. | 5A2 + L149H | 1115 | N.A. | 5P + N108P |
| 544 | A.A | 5A2 + A35G | 830 | A.A | 5A2 + L149H | 1116 | A.A | 5P + N108P |
| 545 | N.A. | 5A2 + A51G | 831 | N.A. | 5A2 + L149I | 1117 | N.A. | 5P + N108Q |
| 546 | A.A | 5A2 + A51G | 832 | A.A | 5A2 + L149I | 1118 | A.A | 5P + N108Q |
| 547 | N.A. | 5A2 + A67G | 833 | N.A. | 5A2 + L149K | 1119 | N.A. | 5P + N108R |
| 548 | A.A | 5A2 + A67G | 834 | A.A | 5A2 + L149K | 1120 | A.A | 5P + N108R |
| 549 | N.A. | 5A2 + A71G | 835 | N.A. | 5A2 + L149M | 1121 | N.A. | 5P + N108S |
| 550 | A.A | 5A2 + A71G | 836 | A.A | 5A2 + L149M | 1122 | A.A | 5P + N108S |
| 551 | N.A. | 5A2 + R11A | 837 | N.A. | 5A2 + L149N | 1123 | N.A. | 5P + N108T |
| 552 | A.A | 5A2 + R11A | 838 | A.A | 5A2 + L149N | 1124 | A.A | 5P + N108T |
| 553 | N.A. | 5A2 + R11C | 839 | N.A. | 5A2 + L149P | 1125 | N.A. | 5P + N108V |
| 554 | A.A | 5A2 + R11C | 840 | A.A | 5A2 + L149P | 1126 | A.A | 5P + N108V |
| 555 | N.A. | 5A2 + R11D | 841 | N.A. | 5A2 + L149Q | 1127 | N.A. | 5P + N108W |
| 556 | A.A | 5A2 + R11D | 842 | A.A | 5A2 + L149Q | 1128 | A.A | 5P + N108W |
| 557 | N.A. | 5A2 + R11E | 843 | N.A. | 5A2 + L149R | 1129 | N.A. | 5P + N108Y |
| 558 | A.A | 5A2 + R11E | 844 | A.A | 5A2 + L149R | 1130 | A.A | 5P + N108Y |
| 559 | N.A. | 5A2 + R11F | 845 | N.A. | 5A2 + L149S | 1131 | N.A. | 5P + T144A |
| 560 | A.A | 5A2 + R11F | 846 | A.A | 5A2 + L149S | 1132 | A.A | 5P + T144A |
| 561 | N.A. | 5A2 + R11G | 847 | N.A. | 5A2 + L149T | 1133 | N.A. | 5P + T144C |
| 562 | A.A | 5A2 + R11G | 848 | A.A | 5A2 + L149T | 1134 | A.A | 5P + T144C |
| 563 | N.A. | 5A2 + R11H | 849 | N.A. | 5A2 + L149V | 1135 | N.A. | 5P + T144D |
| 564 | A.A | 5A2 + R11H | 850 | A.A | 5A2 + L149V | 1136 | A.A | 5P + T144D |
| 565 | N.A. | 5A2 + R11I | 851 | N.A. | 5A2 + L149W | 1137 | N.A. | 5P + T144E |
| 566 | A.A | 5A2 + R11I | 852 | A.A | 5A2 + L149W | 1138 | A.A | 5P + T144E |
| 567 | N.A. | 5A2 + R11K | 853 | N.A. | 5A2 + L149Y | 1139 | N.A. | 5P + T144F |
| 568 | A.A | 5A2 + R11K | 854 | A.A | 5A2 + L149Y | 1140 | A.A | 5P + T144F |
| 569 | N.A. | 5A2 + R11L | 855 | N.A. | 5A2 + V157A | 1141 | N.A. | 5P + T144G |
| 570 | A.A | 5A2 + R11L | 856 | A.A | 5A2 + V157A | 1142 | A.A | 5P + T144G |
| 571 | N.A. | 5A2 + R11M | 857 | N.A. | 5A2 + V157C | 1143 | N.A. | 5P + T144H |
| 572 | A.A | 5A2 + R11M | 858 | A.A | 5A2 + V157C | 1144 | A.A | 5P + T144H |
| 573 | N.A. | 5A2 + R11N | 859 | N.A. | 5A2 + V157D | 1145 | N.A. | 5P + T144I |
| 574 | A.A | 5A2 + R11N | 860 | A.A | 5A2 + V157D | 1146 | A.A | 5P + T144I |
| 575 | N.A. | 5A2 + R11P | 861 | N.A. | 5A2 + V157E | 1147 | N.A. | 5P + T144K |
| 576 | A.A | 5A2 + R11P | 862 | A.A | 5A2 + V157E | 1148 | A.A | 5P + T144K |
| 577 | N.A. | 5A2 + R11Q | 863 | N.A. | 5A2 + V157F | 1149 | N.A. | 5P + T144L |
| 578 | A.A | 5A2 + R11Q | 864 | A.A | 5A2 + V157F | 1150 | A.A | 5P + T144L |
| 579 | N.A. | 5A2 + R11S | 865 | N.A. | 5A2 + V157G | 1151 | N.A. | 5P + T144M |
| 580 | A.A | 5A2 + R11S | 866 | A.A | 5A2 + V157G | 1152 | A.A | 5P + T144M |
| 581 | N.A. | 5A2 + R11T | 867 | N.A. | 5A2 + V157H | 1153 | N.A. | 5P + T144N |
| 582 | A.A | 5A2 + R11T | 868 | A.A | 5A2 + V157H | 1154 | A.A | 5P + T144N |
| 583 | N.A. | 5A2 + R11V | 869 | N.A. | 5A2 + V157I | 1155 | N.A. | 5P + T144P |
| 584 | A.A | 5A2 + R11V | 870 | A.A | 5A2 + V157I | 1156 | A.A | 5P + T144P |
| 585 | N.A. | 5A2 + R11W | 871 | N.A. | 5A2 + V157K | 1157 | N.A. | 5P + T144Q |
| 586 | A.A | 5A2 + R11W | 872 | A.A | 5A2 + V157K | 1158 | A.A | 5P + T144Q |

TABLE 2-continued

Exemplary internal tag and/or structural complement polypeptide sequences

| SEQ ID NO | Polymer | ID | SEQ ID NO | Poly. | ID | SEQ ID NO | Poly. | ID |
|---|---|---|---|---|---|---|---|---|
| 587 | N.A. | 5A2 + R11Y | 873 | N.A. | 5A2 + V157L | 1159 | N.A. | 5P + T144R |
| 588 | A.A | 5A2 + R11Y | 874 | A.A | 5A2 + V157L | 1160 | A.A | 5P + T144R |
| 589 | N.A. | 5A2 + A15C | 875 | N.A. | 5A2 + V157M | 1161 | N.A. | 5P + T144S |
| 590 | A.A | 5A2 + A15C | 876 | A.A | 5A2 + V157M | 1440 | A.A | 5P + T144S |
| 591 | N.A. | 5A2 + A15D | 877 | N.A. | 5A2 + V157N | 1163 | N.A. | 5P + T144V |
| 592 | A.A | 5A2 + A15D | 878 | A.A | 5A2 + V157N | 1164 | A.A | 5P + T144V |
| 593 | N.A. | 5A2 + A15E | 879 | N.A. | 5A2 + V157P | 1165 | N.A. | 5P + T144W |
| 594 | A.A | 5A2 + A15E | 880 | A.A | 5A2 + V157P | 1166 | A.A | 5P + T144W |
| 595 | N.A. | 5A2 + A15F | 881 | N.A. | 5A2 + V157Q | 1167 | N.A. | 5P + T144Y |
| 596 | A.A | 5A2 + A15F | 882 | A.A | 5A2 + V157Q | 1168 | A.A | 5P + T144Y |
| 597 | N.A. | 5A2 + A15G | 883 | N.A. | 5A2 + V157R | 1169 | N.A. | 5P + P157A |
| 598 | A.A | 5A2 + A15G | 884 | A.A | 5A2 + V157R | 1170 | A.A | 5P + P157A |
| 599 | N.A. | 5A2 + A15H | 885 | N.A. | 5A2 + V157S | 1171 | N.A. | 5P + P157C |
| 600 | A.A | 5A2 + A15H | 886 | A.A | 5A2 + V157S | 1172 | A.A | 5P + P157C |
| 601 | N.A. | 5A2 + A15I | 887 | N.A. | 5A2 + V157T | 1173 | N.A. | 5P + P157D |
| 602 | A.A | 5A2 + A15I | 888 | A.A | 5A2 + V157T | 1174 | A.A | 5P + P157D |
| 603 | N.A. | 5A2 + A15K | 889 | N.A. | 5A2 + V157W | 1175 | N.A. | 5P + P157E |
| 604 | A.A | 5A2 + A15K | 890 | A.A | 5A2 + V157W | 1176 | A.A | 5P + P157E |
| 605 | N.A. | 5A2 + A15L | 891 | N.A. | 5A2 + V157Y | 1177 | N.A. | 5P + P157F |
| 606 | A.A | 5A2 + A15L | 892 | A.A | 5A2 + V157Y | 1178 | A.A | 5P + P157F |
| 607 | N.A. | 5A2 + A15M | 893 | N.A. | 5A2 + Q20K | 1179 | N.A. | 5P + P157G |
| 608 | A.A | 5A2 + A15M | 894 | A.A | 5A2 + Q20K | 1180 | A.A | 5P + P157G |
| 609 | N.A. | 5A2 + A15N | 895 | N.A. | 5A2 + V27M | 1181 | N.A. | 5P + P157H |
| 610 | A.A | 5A2 + A15N | 896 | A.A | 5A2 + V27M | 1182 | A.A | 5P + P157H |
| 611 | N.A. | 5A2 + A15P | 897 | N.A. | 5A2 + N33K | 1183 | N.A. | 5P + P157I |
| 612 | A.A | 5A2 + A15P | 898 | A.A | 5A2 + N33K | 1184 | A.A | 5P + P157I |
| 613 | N.A. | 5A2 + A15Q | 899 | N.A. | 5A2 + V38I | 1185 | N.A. | 5P + P157K |
| 614 | A.A | 5A2 + A15Q | 900 | A.A | 5A2 + V38I | 1186 | A.A | 5P + P157K |
| 615 | N.A. | 5A2 + A15R | 901 | N.A. | 5A2 + I56N | 1187 | N.A. | 5P + P157L |
| 616 | A.A | 5A2 + A15R | 902 | A.A | 5A2 + I56N | 1188 | A.A | 5P + P157L |
| 617 | N.A. | 5A2 + A15S | 903 | N.A. | 5A2 + D108N | 1189 | N.A. | 5P + P157M |
| 618 | A.A | 5A2 + A15S | 904 | A.A | 5A2 + D108N | 1190 | A.A | 5P + P157M |
| 619 | N.A. | 5A2 + A15T | 905 | N.A. | 5A2 + N144T | 1191 | N.A. | 5P + P157N |
| 620 | A.A | 5A2 + A15T | 906 | A.A | 5A2 + N144T | 1192 | A.A | 5P + P157N |
| 621 | N.A. | 5A2 + A15V | 907 | N.A. | 5A2 + V27M + A35G | 1193 | N.A. | 5P + P157Q |
| 622 | A.A | 5A2 + A15V | 908 | A.A | 5A2 + V27M + A35G | 1194 | A.A | 5P + P157Q |
| 623 | N.A. | 5A2 + A15W | 909 | N.A. | 5A2 + A71G + K75E | 1195 | N.A. | 5P + P157R |
| 624 | A.A | 5A2 + A15W | 910 | A.A | 5A2 + A71G + K75E | 1196 | A.A | 5P + P157R |
| 625 | N.A. | 5A2 + A15Y | 911 | N.A. | 5A2 + R11E + L149M | 1197 | N.A. | 5P + P157S |
| 626 | A.A | 5A2 + A15Y | 912 | A.A | 5A2 + R11E + L149M | 1198 | A.A | 5P + P157S |
| 627 | N.A. | 5A2 + L18A | 913 | N.A. | 5A2 + R11E + V157P | 1199 | N.A. | 5P + P157T |
| 628 | A.A | 5A2 + L18A | 914 | A.A | 5A2 + R11E + V157P | 1200 | A.A | 5P + P157T |
| 629 | N.A. | 5A2 + L18C | 915 | N.A. | 5A2 + D108N + N144T | 1201 | N.A. | 5P + P157V |
| 630 | A.A | 5A2 + L18C | 916 | A.A | 5A2 + D108N + N144T | 1202 | A.A | 5P + P157V |
| 631 | N.A. | 5A2 + L18D | 917 | N.A. | 5A2 + L149M + V157D | 1203 | N.A. | 5P + P157W |
| 632 | A.A | 5A2 + L18D | 918 | A.A | 5A2 + L149M + V157D | 1204 | A.A | 5P + P157W |
| 633 | N.A. | 5A2 + L18E | 919 | N.A. | 5A2 + L149M + V157P | 1205 | N.A. | 5P + P157Y |
| 634 | A.A | 5A2 + L18E | 920 | A.A | 5A2 + L149M + V157P | 1206 | A.A | 5P + P157Y |
| 635 | N.A. | 5A2 + L18F | 921 | N.A. | 3P (5A2 + R11E + L149M + V157P) | 1207 | N.A. | 5P + I107L |
| 636 | A.A | 5A2 + L18F | 922 | A.A | 3P (5A2 + R11E + L149M + V157P) | 1208 | A.A | 5P + I107L |
| 637 | N.A. | 5A2 + L18G | 923 | N.A. | 3P + D108N | 1209 | N.A. | 5P + K75E |
| 638 | A.A | 5A2 + L18G | 924 | A.A | 3P + D108N | 1210 | A.A | 5P + K75E |
| 639 | N.A. | 5A2 + L18H | 925 | N.A. | 3P + N144T | 1211 | N.A. | 5P + K123E + N156D |
| 640 | A.A | 5A2 + L18H | 926 | A.A | 3P + N144T | 1212 | A.A | 5P + K123E + N156D |
| 641 | N.A. | 5A2 + L18I | 927 | N.A. | 3E (5A2 + R11E + L149M + V157E) | 1213 | N.A. | 5P + I76V |
| 642 | A.A | 5A2 + L18I | 928 | A.A | 3E (5A2 + R11E + L149M + V157E) | 1214 | A.A | 5P + I76V |
| 643 | N.A. | 5A2 + L18K | 929 | N.A. | 3E + D108N | 1215 | N.A. | 5P + G48D + H57R + L92M + I99V |
| 644 | A.A | 5A2 + L18K | 930 | A.A | 3E + D108N | 1216 | A.A | 5P + G48D + H57R + L92M + I99V |
| 645 | N.A. | 5A2 + L18M | 931 | N.A. | 3E + N144T | 1217 | N.A. | 5P + F31L + V36A + I99V |
| 646 | A.A | 5A2 + L18M | 932 | A.A | 3E + N144T | 1218 | A.A | 5P + F31L + V36A + I99V |
| 647 | N.A. | 5A2 + L18N | 933 | N.A. | 5P (3P + D108N + N144T) | 1219 | N.A. | 5P + F31L + H93P |
| 648 | A.A | 5A2 + L18N | 934 | A.A | 5P (3P + D108N + N144T) | 1220 | A.A | 5P + F31L + H93P |

TABLE 2-continued

Exemplary internal tag and/or structural complement polypeptide sequences

| SEQ ID NO | Polymer | ID | SEQ ID NO | Poly. | ID | SEQ ID NO | Poly. | ID |
|---|---|---|---|---|---|---|---|---|
| 649 | N.A. | 5A2 + L18P | 935 | N.A. | 6P (5P + I56N) | 1221 | N.A. | 5P + V90A |
| 650 | A.A | 5A2 + L18P | 936 | A.A | 6P (5P + I56N) | 1222 | A.A | 5P + V90A |
| 651 | N.A. | 5A2 + L18Q | 937 | N.A. | 5E (3E + D108N + N144T) | 1223 | N.A. | 5P + I44V |
| 652 | A.A | 5A2 + L18Q | 938 | A.A | 5E (3E + D108N + N144T) | 1224 | A.A | 5P + I44V |
| 653 | N.A. | 5A2 + L18R | 939 | N.A. | 6E (5E + I56N) | 1225 | N.A. | 5P + L46R + H86Q + M106V |
| 654 | A.A | 5A2 + L18R | 940 | A.A | 6E (5E + I56N) | 1226 | A.A | 5P + L46R + H86Q + M106V |
| 655 | N.A. | 5A2 + L18S | 941 | N.A. | NLpoly1 (5A2 + R11N + A15S + L18Q + F31I + V58A + A67D + M106V + L149M + V157D) | 1227 | N.A. | 5P + R141H |
| 656 | A.A | 5A2 + L18S | 942 | A.A | NLpoly1 (5A2 + R11N + A15S + L18Q + F31I + V58A + A67D + M106V + L149M + V157D) | 1228 | A.A | 5P + R141H |
| 657 | N.A. | 5A2 + L18T | 943 | N.A. | NLpoly2 (5A2 + A15S + L18Q + F31I + V58A + A67D + M106V + L149M + V157D) | 1229 | N.A. | 5P + N33D + V58A |
| 658 | A.A | 5A2 + L18T | 944 | A.A | NLpoly2 (5A2 + A15S + L18Q + F31I + V58A + A67D + M106V + L149M + V157D) | 1230 | A.A | 5P + N33D + V58A |
| 659 | N.A. | 5A2 + L18V | 945 | N.A. | NLpoly3 (5A2 + R11N + L18Q + F31I + V58A + A67D + M106V + L149M + V157D) | 1231 | N.A. | 5P + I56N + P157H |
| 660 | A.A | 5A2 + L18V | 946 | A.A | NLpoly3 (5A2 + R11N + L18Q + F31I + V58A + A67D + M106V + L149M + V157D) | 1232 | A.A | 5P + I56N + P157H |
| 661 | N.A. | 5A2 + L18W | 947 | N.A. | NLpoly4 (5A2 + R11N + A15S + F31I + V58A + A67D + M106V + L149M + V157D) | 1233 | N.A. | 5P + L46Q + P157H |
| 662 | A.A | 5A2 + L18W | 948 | A.A | NLpoly4 (5A2 + R11N + A15S + F31I + V58A + A67D + M106V + L149M + V157D) | 1234 | A.A | 5P + L46Q + P157H |
| 663 | N.A. | 5A2 + L18Y | 949 | N.A. | NLpoly5 (5A2 + R11N + A15S + L18Q + V58A + A67D + M106V + L149M + V157D) | 1235 | N.A. | 5P + I59V |
| 664 | A.A | 5A2 + L18Y | 950 | A.A | NLpoly5 (5A2 + R11N + A15S + L18Q + V58A + A67D + M106V + L149M + V157D) | 1236 | A.A | 5P + I59V |
| 665 | N.A. | 5A2 + F31A | 951 | N.A. | NLpoly6 (5A2 + R11N + A15S + L18Q + F31I + A67D + M106V + L149M + V157D) | 1237 | N.A. | 5P + A51T + E74K + P113L |
| 666 | A.A | 5A2 + F31A | 952 | A.A | NLpoly6 (5A2 + R11N + A15S + L18Q + F31I + A67D + M106V + L149M + V157D) | 1238 | A.A | 5P + A51T + E74K + P113L |

TABLE 2-continued

Exemplary internal tag and/or structural complement polypeptide sequences

| SEQ ID NO | Polymer | ID | SEQ ID NO | Poly. | ID | SEQ ID NO | Poly. | ID |
|---|---|---|---|---|---|---|---|---|
| 667 | N.A. | 5A2 + F31C | 953 | N.A. | NLpoly7 (5A2 + R11N + A15S + L18Q + F31I + V58A + M106V + L149M + V157D) | 1239 | N.A. | 5P + V36A |
| 668 | A.A. | 5A2 + F31C | 954 | A.A. | NLpoly7 (5A2 + R11N + A15S + L18Q + F31I + V58A + M106V + L149M + V157D) | 1240 | A.A. | 5P + V36A |
| 669 | N.A. | 5A2 + F31D | 955 | N.A. | NLpoly8 (5A2 + R11N + A15S + L18Q + F31I + V58A + A67D + L149M + V157D) | 1241 | N.A. | 5P + A51T |
| 670 | A.A. | 5A2 + F31D | 956 | A.A. | NLpoly8 (5A2 + R11N + A15S + L18Q + F31I + V58A + A67D + L149M + V157D) | 1242 | A.A. | 5P + A51T |
| 671 | N.A. | 5A2 + F31E | 957 | N.A. | NLpoly9 (5A2 + R11N + A15S + L18Q + F31I + V58A + A67D + M106V + V157D) | 1243 | N.A. | 5P + H57R |
| 672 | A.A. | 5A2 + F31E | 958 | A.A. | NLpoly9 (5A2 + R11N + A15S + L18Q + F31I + V58A + A67D + M106V + V157D) | 1244 | A.A. | 5P + H57R |
| 673 | N.A. | 5A2 + F31G | 959 | N.A. | NLpoly10 (5A2 + R11N + A15S + L18Q + F31I + V58A + A67D + M106V + L149M) | 1245 | N.A. | 5P + V58A |
| 674 | A.A. | 5A2 + F31G | 960 | A.A. | NLpoly10 (5A2 + R11N + A15S + L18Q + F31I + V58A + A67D + M106V + L149M) | 1246 | A.A. | 5P + V58A |
| 675 | N.A. | 5A2 + F31H | 961 | N.A. | NLpoly11 (5A2 + A15S + L18Q + M106V + L149M + V157D) | 1247 | N.A. | 5P + E74K |
| 676 | A.A. | 5A2 + F31H | 962 | A.A. | NLpoly11 (5A2 + A15S + L18Q + M106V + L149M + V157D) | 1248 | A.A. | 5P + E74K |
| 677 | N.A. | 5A2 + F31I | 963 | N.A. | NLpoly12 (5A2 + A15S + L18Q + A67D + M106V + L149M + V157D) | 1249 | N.A. | 5P + H86Q |
| 678 | A.A. | 5A2 + F31I | 964 | A.A. | NLpoly12 (5A2 + A15S + L18Q + A67D + M106V + L149M + V157D) | 1250 | A.A. | 5P + H86Q |
| 679 | N.A. | 5A2 + F31K | 965 | N.A. | NLpoly13 (5A2 + R11N + A15S + L18Q + M106V + L149M + V157D) | 1251 | N.A. | 5P + H93P |
| 680 | A.A. | 5A2 + F31K | 966 | A.A. | NLpoly13 (5A2 + R11N + A15S + L18Q + M106V + L149M + V157D) | 1252 | A.A. | 5P + H93P |
| 681 | N.A. | 5A2 + F31L | 967 | N.A. | 5P + V | 1253 | N.A. | 5P + I99V |
| 682 | A.A. | 5A2 + F31L | 968 | A.A. | 5P + V | 1254 | A.A. | 5P + I99V |
| 683 | N.A. | 5A2 + F31M | 969 | N.A. | 5P + A | 1255 | N.A. | 5P + K123E |
| 684 | A.A. | 5A2 + F31M | 970 | A.A. | 5P + A | 1256 | A.A. | 5P + K123E |
| 685 | N.A. | 5A2 + F31N | 971 | N.A. | 5P + VT | 1257 | N.A. | 5P + T128S |
| 686 | A.A. | 5A2 + F31N | 972 | A.A. | 5P + VT | 1258 | A.A. | 5P + T128S |
| 687 | N.A. | 5A2 + F31P | 973 | N.A. | 5P + VA | 1259 | N.A. | 5P + L142Q + T154N |
| 688 | A.A. | 5A2 + F31P | 974 | A.A. | 5P + VA | 1260 | A.A. | 5P + L142Q + T154N |
| 689 | N.A. | 5A2 + F31Q | 975 | N.A. | 5P + AT | 1261 | N.A. | 5P + H57Q |
| 690 | A.A. | 5A2 + F31Q | 976 | A.A. | 5P + AT | 1262 | A.A. | 5P + H57Q |

TABLE 2-continued

Exemplary internal tag and/or structural complement polypeptide sequences

| SEQ ID NO | Polymer | ID | SEQ ID NO | Poly. | ID | SEQ ID NO | Poly. | ID |
|---|---|---|---|---|---|---|---|---|
| 691 | N.A. | 5A2 + F31R | 977 | N.A. | 5P + AA | 1263 | N.A. | 5P + L92M |
| 692 | A.A | 5A2 + F31R | 978 | A.A | 5P + AA | 1264 | A.A | 5P + L92M |
| 693 | N.A. | 5A2 + F31S | 979 | N.A. | 5P + GG | 1265 | N.A. | 5P + P113L |
| 694 | A.A | 5A2 + F31S | 980 | A.A | 5P + GG | 1266 | A.A | 5P + P113L |
| 695 | N.A. | 5A2 + F31T | 981 | N.A. | 5P + AA | 1267 | N.A. | 5P + G48D |
| 696 | A.A | 5A2 + F31T | 982 | A.A | 5P + AA | 1268 | A.A | 5P + G48D |
| 697 | N.A. | 5A2 + F31V | 983 | N.A. | 5P + ATG | 1269 | N.A. | 5P − B9 (−147-157) |
| 698 | A.A | 5A2 + F31V | 984 | A.A | 5P + ATG | 1270 | A.A | 5P − B9 (−147-157) |
| 699 | N.A. | 5A2 + F31W | 985 | N.A. | 5P + VTG | 1271 | N.A. | 5P + L46R + P157S |
| 700 | A.A | 5A2 + F31W | 986 | A.A | 5P + VTG | 1272 | A.A | 5P + L46R + P157S |
| 701 | N.A. | 5A2 + F31Y | 987 | N.A. | 5P + VTA | 1273 | N.A. | 5P + L46H + P157H |
| 702 | A.A | 5A2 + F31Y | 988 | A.A | 5P + VTA | 1274 | A.A | 5P + L46H + P157H |
| 703 | N.A. | 5A2 + V58A | 989 | N.A. | 5P + GTA | 1275 | N.A. | 5P + L46R + H93P |
| 704 | A.A | 5A2 + V58A | 990 | A.A | 5P + GTA | 1276 | A.A | 5P + L46R + H93P |
| 705 | N.A. | 5A2 + V58C | 991 | N.A. | 5P + VTGW | 1277 | N.A. | 5P + L46R + H93P + F31L |
| 706 | A.A | 5A2 + V58C | 992 | A.A | 5P + VTGW | 1278 | A.A | 5P + L46R + H93P + F31L |
| 707 | N.A. | 5A2 + V58D | 993 | N.A. | 5P + VTGWR | 1279 | N.A. | 5P + L46R + H93P + K75E |
| 708 | A.A | 5A2 + V58D | 994 | A.A | 5P + VTGWR | 1280 | A.A | 5P + L46R + H93P + K75E |
| 709 | N.A. | 5A2 + V58E | 995 | N.A. | 5P + VTGWE | 1281 | N.A. | 5P + L46R + H93P + I76V |
| 710 | A.A | 5A2 + V58E | 996 | A.A | 5P + VTGWE | 1282 | A.A | 5P + L46R + H93P + I76V |
| 711 | N.A. | 5A2 + V58F | 997 | N.A. | 5P + VTGWK | 1283 | N.A. | 8S (5P + L46R + H93P + P157S + F31L) |
| 712 | A.A | 5A2 + V58F | 998 | A.A | 5P + VTGWK | 1284 | A.A | 8S (5P + L46R + H93P + P157S + F31L) |
| 713 | N.A. | 5A2 + V58G | 999 | N.A. | 5P + VTGWQ | 1285 | N.A. | 5P + L46R + H93P + P157S + K75E |
| 714 | A.A | 5A2 + V58G | 1000 | A.A | 5P + VTGWQ | 1286 | A.A | 5P + L46R + H93P + P157S + K75E |
| 715 | N.A. | 5A2 + V58H | 1001 | N.A. | 5P + VTGWH | 1287 | N.A. | 5P + L46R + H93P + P157S + I76V |
| 716 | A.A | 5A2 + V58H | 1002 | A.A | 5P + VTGWH | 1288 | A.A | 5P + L46R + H93P + P157S + I76V |
| 717 | N.A. | 5A2 + V58I | 1003 | N.A. | 5P D1 (−157) | 1289 | N.A. | 12S (8S + A51T + K75E + I76V + I107L) |
| 718 | A.A | 5A2 + V58I | 1004 | A.A | 5P D1 (−157) | 1290 | A.A | 12S (8S + A51T + K75E + I76V + I107L) |
| 719 | N.A. | 5A2 + V58K | 1005 | N.A. | 5P D2 (−156-157) | 1291 | N.A. | 11S (12 − A51T) |
| 720 | A.A | 5A2 + V58K | 1006 | A.A | 5P D2 (−156-157) | 1292 | A.A | 11S (12 − A51T) |
| 721 | N.A. | 5A2 + V58L | 1007 | N.A. | 5P D3 (−155-157) | 1293 | N.A. | 12S − K75E |
| 722 | A.A | 5A2 + V58L | 1008 | A.A | 5P D3 (−155-157) | 1294 | A.A | 12S − K75E |
| 723 | N.A. | 5A2 + V58M | 1009 | N.A. | 5P D4 (−154-157) | 1295 | N.A. | 12S − I76V |
| 724 | A.A | 5A2 + V58M | 1010 | A.A | 5P D4 (−154-157) | 1296 | A.A | 12S − I76V |
| 725 | N.A. | 5A2 + V58N | 1011 | N.A. | 5P D5 (−153-157) | 1297 | N.A. | 12S − I107L |
| 726 | A.A | 5A2 + V58N | 1012 | A.A | 5P D5 (−153-157) | 1298 | A.A | 12S − I107L |

The polypeptides and coding nucleic acid sequences of Table 2 (SEQ ID NOS: 441-1298) all contain N-terminal Met residues (amino acids) or ATG start codons (nucleic acids). In some embodiments, the polypeptides and coding nucleic acid sequences of Table 2 are provided without N-terminal Met residues or ATG start codons (SEQ ID NOS: 1299-2156).

In certain embodiments, an internal tag and/or structural complement comprises one of the amino acid polymers of SEQ ID NOS: 441-2156. In some embodiments, an internal tag and/or structural complement comprises a single amino acid difference from SEQ ID NO: 440.

In some embodiments, an internal tag and/or structural complement comprises two or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30 . . . 35 . . . 40 . . . 45 . . . 50, or more) amino acid differences from SEQ ID NO: 440 and/or any of the amino acid polymers of SEQ ID NOS:441-2156. In some embodiments, an internal tag and/or structural complement are provided comprising the sequence of one of the amino acid polymers of SEQ ID NOS: 441-2156 with one or more additions, substitutions, and/or deletions. In some embodiments, an internal tag and/or structural complement or a portion thereof comprises greater than 70% sequence identity (e.g., >71%, >75%, >80%, >85%, >90%, >91%, >92%, >93%, >94%, >95%, >96%, >97%, >98%, or >99%) with one or more of the amino acid polymers of SEQ ID NOS: 441-2156.

In certain embodiments, a nucleic acid from Table 2 is provided. In some embodiments, a nucleic acid encoding a polypeptide from Table 2 (e.g., inserted into a polypeptide of interest) is provided. In some embodiments, a nucleic acid of the present invention codes for a polypeptide that comprises a single amino acid difference from SEQ ID NO: 440 and/or any of the amino acid polymers of SEQ ID NOS: 441-2156 (e.g., inserted into a polypeptide of interest). In some embodiments, nucleic acids code for a polypeptide comprising two or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30 . . . 35 . . . 40 . . . 45 . . . 50, or more) amino acid differences from SEQ ID NO: 440 and/or any of the polypeptides listed in Table 2 (e.g., inserted into a polypeptide of interest). In some embodiments, nucleic acids are provided comprising the sequence of one of the nucleic acid polymers of SEQ ID NOS: 441-2156 (e.g., inserted into a polypeptide of interest). In some embodiments, nucleic acids are provided comprising the sequence of one of the nucleic acid polymers of SEQ ID NOS: 441-2156 with one or more additions, substitutions, and/or deletions. In some embodiments, a nucleic acid or a portion thereof comprises greater than 70% sequence identity (e.g., >71%, >75%, >80%, >85%, >90%, >91%, >92%, >93%, >94%, >95%, >96%, >97%, >98%, or >99%) with one or more of the nucleic acid polymers of SEQ ID NOS: 441-2156 (e.g., inserted into a polypeptide of interest). In some embodiments, a nucleic acid or a portion thereof codes for an polypeptide comprising greater than 70% sequence identity (e.g., >71%, >75%, >80%, >85%, >90%, >91%, >92%, >93%, >94%, >95%, >96%, >97%, >98%, or >99%) with one or more of the amino acid polymers of SEQ ID NOS: 441-2156 (e.g., inserted into a polypeptide of interest). In some embodiments, nucleic acids are provided that code for one of the polypeptides of SEQ ID NOS: 441-2156 (e.g., inserted into a polypeptide of interest). In some embodiments, nucleic acids are provided that code for one of the polypeptides of SEQ ID NOS: 441-2156 with one or more additions, substitutions, and/or deletions (e.g., inserted into a polypeptide of interest).

The present invention provides compositions and methods that are useful in a variety of fields including basic research, medical research, molecular diagnostics, etc. The reagents and assays described herein are not limited to any particular applications, and any useful application should be viewed as being within the scope of the present invention.

Typical applications that make use of embodiments of the present invention involve the monitoring/detection of protein-protein interactions (e.g., heterodimers, homodimers) (See FIG. 1), protein-RNA interactions, protein-DNA interactions, protein-small molecule interactions, or any other combinations of molecular entities. A protein of interest is internally tagged and the second entity of interest is attached to the structural complement. If a detectable signal is produced under the particular assay conditions, then interaction of the protein of interest and the entity of interest is inferred. Such assays are useful for monitoring molecular interactions under any suitable conditions (e.g., in vitro, in vivo, in situ, whole animal, etc.), and find use in, for example, drug discovery, elucidating molecular pathways, studying equilibrium or kinetic aspects of complex assembly, high throughput screening, proximity sensor, etc.

Figure 2:
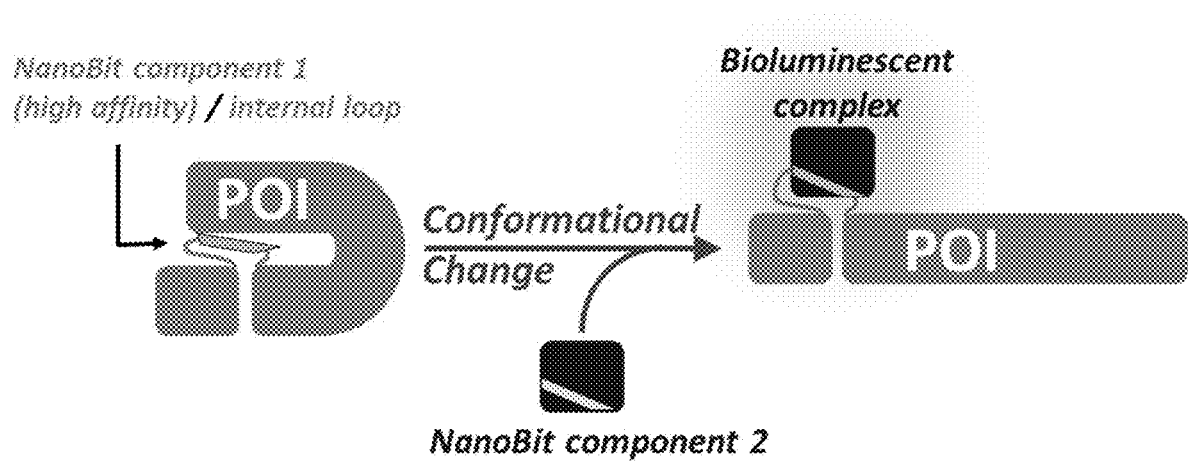
FIG. 2 shows a schematic depiction of an exemplary embodiment in which an internal tag (e.g., NLpep or NLpoly) is inserted into a first protein of interest (POI 1), and a free complement sequence (e.g., NLpep or NLpoly) is provided. In this example, the internal tag is placed in a position that is accessible only after the protein of interest undergoes a conformational change that allows the internal tag to be accessible by the complement sequence. The internal tag and complement sequence have high affinity for each other such that a complex forms when the internal tag and complement sequence associate. A bioluminescent complex is then formed between the internal tag and complement sequence when they are present in the same sample.
Figure 3:
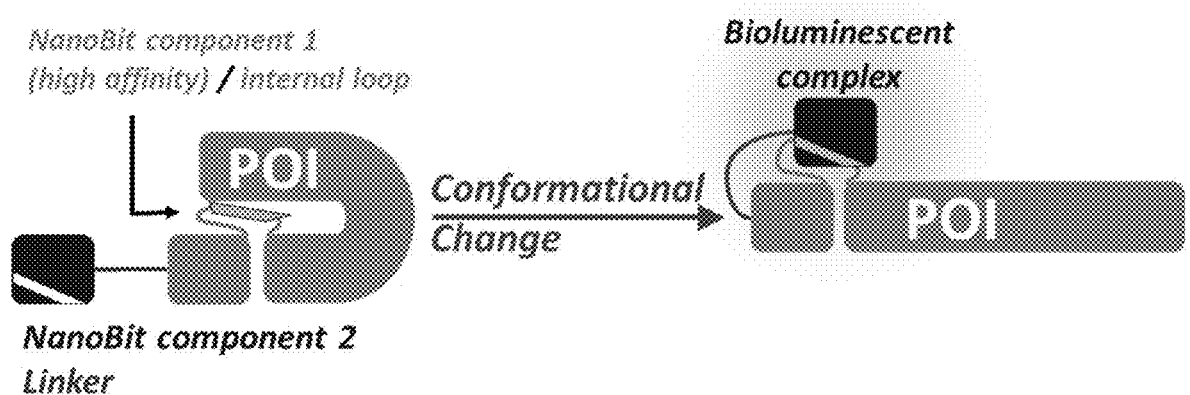
FIG. 3 shows a schematic depiction of an exemplary embodiment in which an internal tag (e.g., NLpep or NLpoly) and its structural complement are inserted/fused to a polypeptide of interest (POI 1). In this example, the internal tag is placed in a position that is accessible only after the protein of interest undergoes a conformational change that allows the internal tag to be accessible by the complement sequence. The internal tag and complement sequence have high affinity for each other such that a complex forms when the internal tag and complement sequence associate. A bioluminescent complex is then formed between the internal tag and complement sequence when they are present in the same sample.

Other typical applications that make use of embodiments of the present invention involve the detection or localization (e.g., cellular localization, subcellular localization, etc.) of a protein or polypeptide (See FIG. 2). A protein of interest in a sample is internally tagged, and a structural complement is added to the sample. If a detectable signal is produced under the particular assay conditions, then the presence or location of the protein of interest is inferred. Such assays are useful for detecting or localizing a protein under any suitable conditions (e.g., in vitro, in vivo, in situ, whole animal, etc.), and find use in, for example, drug discovery, elucidating molecular pathways, studying equilibrium or kinetic aspects of complex assembly, high throughput screening, proximity sensor, etc.

In some embodiments, an internal tag and structural complement of known characteristics (e.g., spectral characteristics, mutual affinity of pair) is used to elucidate the affinity of, or understand the interaction of, a protein of interest and a potentially associated entity of interest (protein, nucleic acid, small molecule, etc.). In other embodiments, a well-characterized interaction pair is used to determine the characteristics (e.g., spectral characteristics, mutual affinity of pair) of an internal tag and structural complement.

Embodiments described herein find use in drug screening and/or drug development. For example, the interaction of a small molecule drug or an entire library of small molecules (e.g., labeled with structural complement) with an internally tagged target protein of interest (e.g., therapeutic target) is monitored under one or more relevant conditions (e.g., physiological conditions, disease conditions, etc.). In other embodiments, the ability of a small molecule drug or an entire library of small molecules to enhance or inhibit the interactions between two entities (e.g., receptor and ligand, protein-protein, etc.) is assayed. In some embodiments, drug screening applications are carried out in a high through-put format to allow for the detection of the binding of tens of thousands of different molecules to a target, or to test the effect of those molecules on the binding of other entities.

In some embodiments, the present invention provides the detection of molecular interactions in living organisms (e.g., bacteria, yeast, eukaryotes, mammals, primates, human, etc.) and/or cells. In some embodiments, internally tagged protein and complement-labeled protein are co-expressed in the cell or whole organism, and signal is detected and correlated to the formation of the interaction complex. In some embodiments, cells are transiently and/or stably transformed or transfected with vector(s) (e.g., encoding internally-tagged protein, complement-labeled protein, etc.). In some embodiments, transgenic organisms are generated that code for the necessary components (e.g., internally-tagged protein, complement-labeled protein, etc.) for carrying out the assays described herein. In other embodiments, vectors are injected into whole organisms.

The present invention also provides methods for the design and/or optimization of internal tags and structural complements and the bioluminescent complexes that form therefrom. Any suitable method for the design of non-luminescent pairs/groups that are consistent with embodiments described herein, and/or panels thereof, is within the scope of the present invention.

EXPERIMENTAL

Example 1

Figure 4:
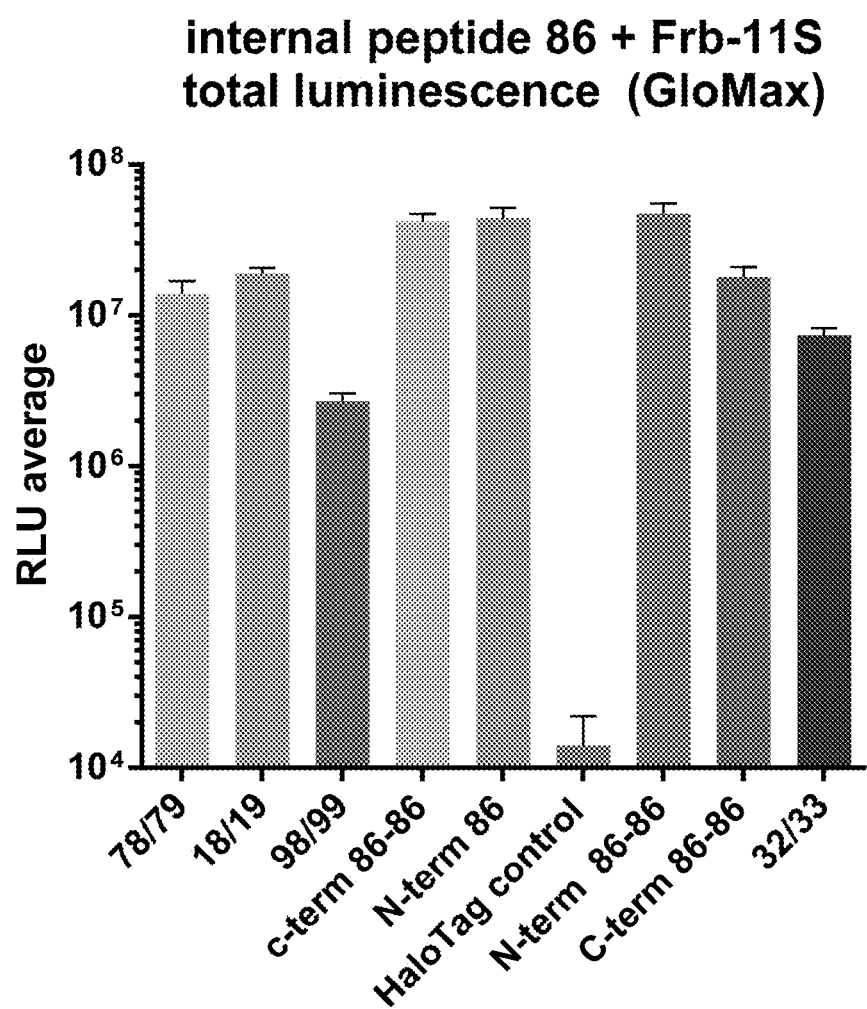
FIG. 4 shows the results of a representative experiment demonstrating structural complementation of the high affinity NLpeptide86 internal tag inserted into the HALOTAG protein (Promega Corp) and NLpoly11S. In this experiment, HeLa cells were transfected with the expression constructs for the indicated constructs. The cells were incubated for 24 hours. Luminescence of each sample was measured following addition of the NANOLUC substrate furimazine
Figure 5:
FIG. 5 shows an image demonstrating function of a HALOTAG protein (Promega Corp) having the high affinity NLpeptide86 inserted therein.
Figure 5:
Figure 5:
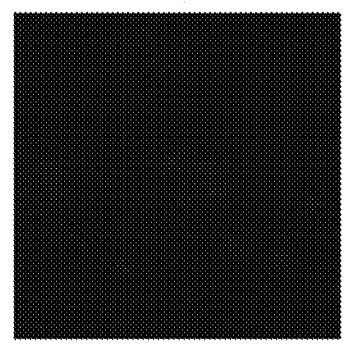
Figure 5:
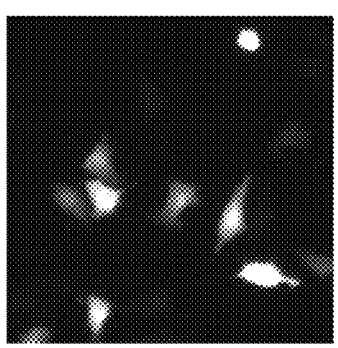
Figure 5:
Figure 5:
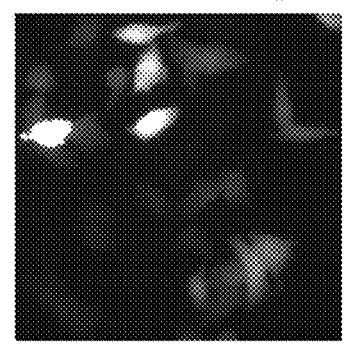
Figure 6:
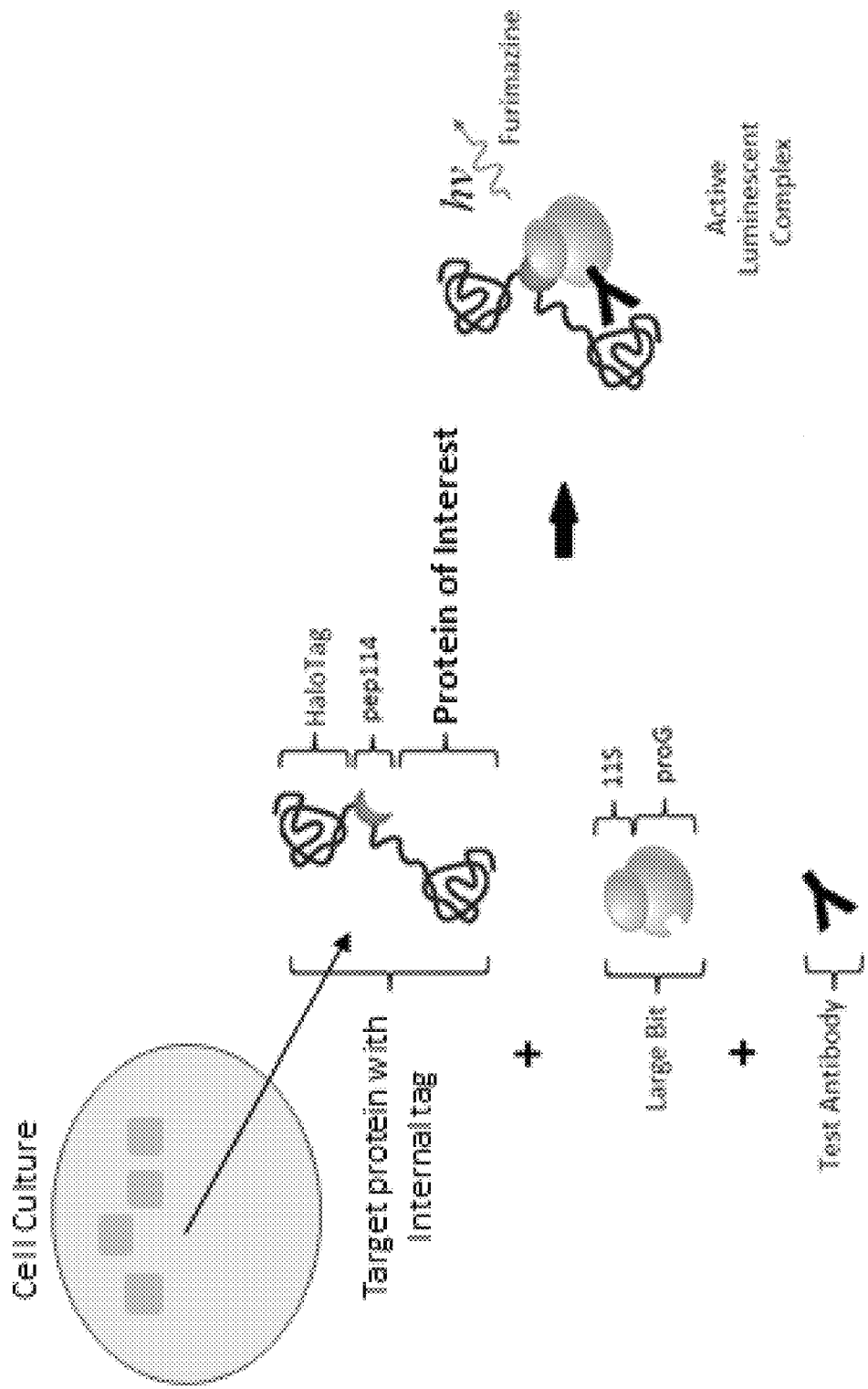
FIG. 6 depicts a schematic of how the assay components are used to screen for antibody binding to target protein by way of antibody driven NANOLUC bioluminescence complementation between NLpoly11S-fused protein G and internally tagged NLpep114 target protein. The Target, containing an internal pep114 tag, is expressed in mammalian cell culture with an IL6 signal peptide (SP). The SP directs the Target to the secretion pathway. The Target can be assayed in the media (+/-) cells. In the example, a purified preparation of the Large Bit (11S-protein G fusion protein) and Test Antibody are added directly to the mammalian cell culture. The protein G domain of the Large Bit binds to the Fc region of the Test Antibody between the Heavy Chain Constant Domains 2 and 3. If the Test Antibody binds to the Target, the Large and Small Bits can come together to form an active luminesent complex that is detected by furimazine.
Figure 7:
FIG. 7 depicts the target protein of interest configurations with the NLpep114 tag either unencumbered on the C-terminus serving as a control, or placed between polypeptides as an internal tag. VEGFA is shown here as this target protein serves in the proof of concept data. Any soluble target protein of interest can be used. HT (HALOTAG), 114 (Small Bit), VEGF (Vascular Endothelial Growth Factor), FLAG (FLAG octapeptide). ATG1915: Control Target with a terminal Small Bit; ATG 1917: Experimental Target with the Small Bit between two large domains; and ATG 1946: Experimental Target with the Small Bit between one large and one small domain.
Figure 8:
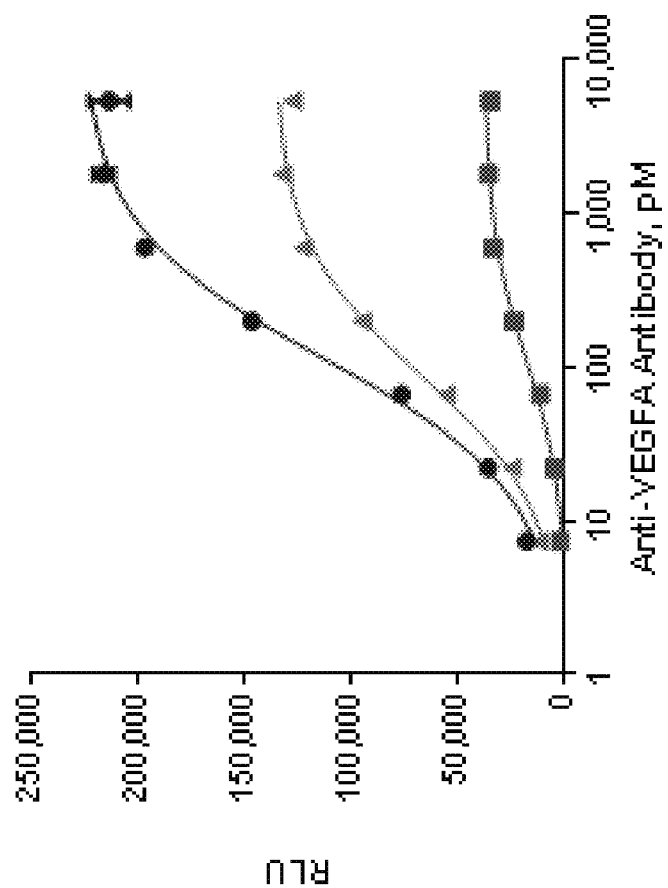
FIG. 8 shows target antibody specific NANOLUC bioluminescence complementation by the detection of anti-VEGFA specific antibody binding to the NLpep114 tagged VEGFA target proteins as determined by an increase in bioluminescence in an antibody concentration dependent manner. This increase in bioluminescence was antibody: target specific as isotype controls did not produce light (not shown).
Figure 8:
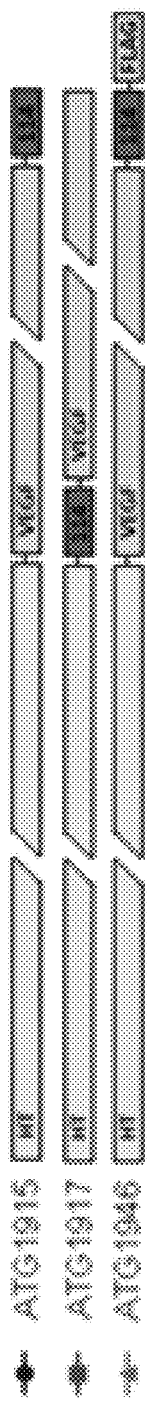
Figure 9:
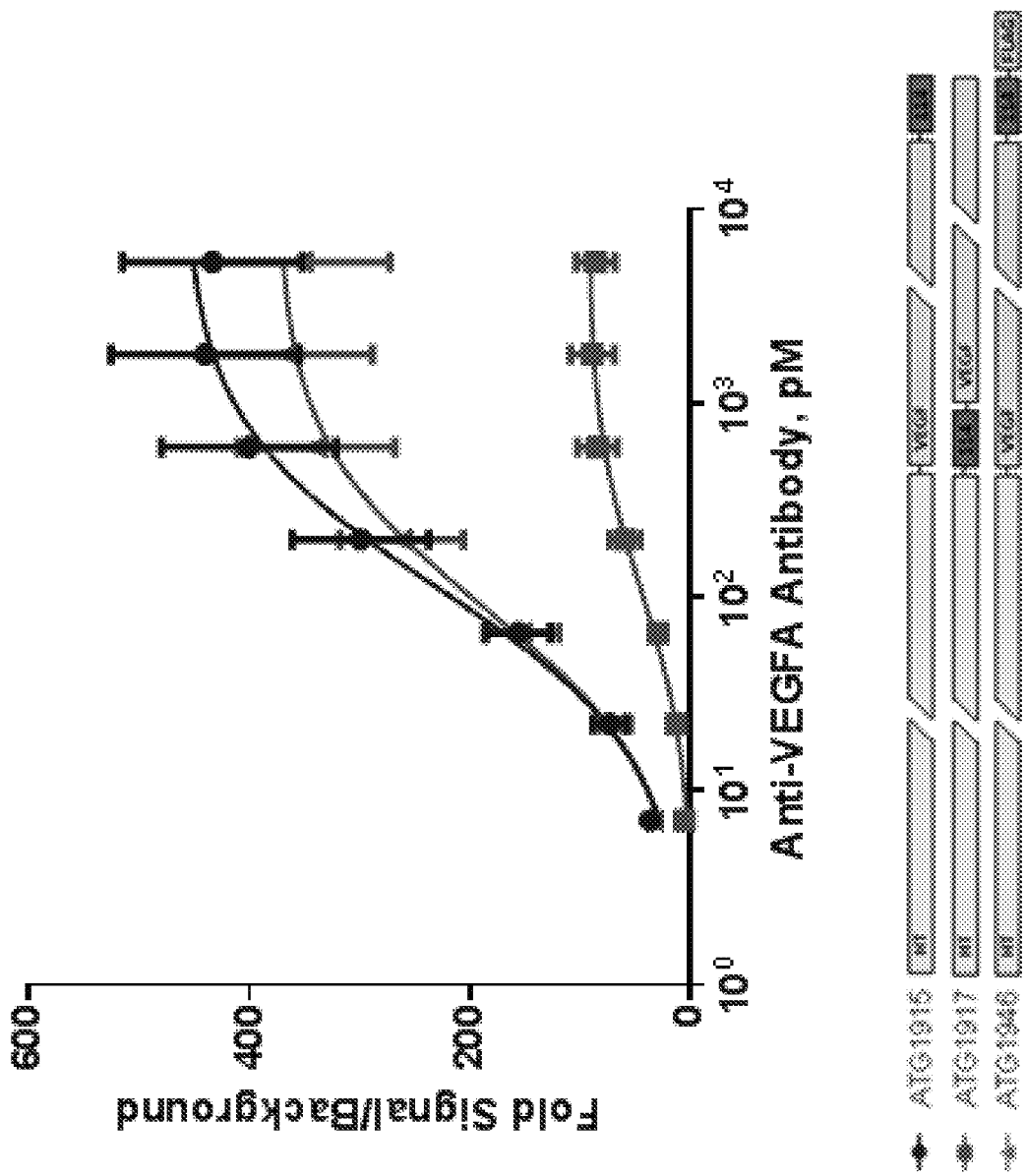
FIG. 9 shows target antibody specific NANOLUC bioluminescence complementation as fold signal/background. The signal window of detection of anti-VEGFA specific antibody binding to the NLpep114 tagged VEGFA target proteins as determined by the increase in bioluminescence in the presence of antibody over background of assay components without antibody present. The signal over background in RLU was calculated from data obtained in FIG. 8 and found to increase from 75-450 fold in response to increasing anti-VEGFA antibody over the concentration range used.
Figure 10:
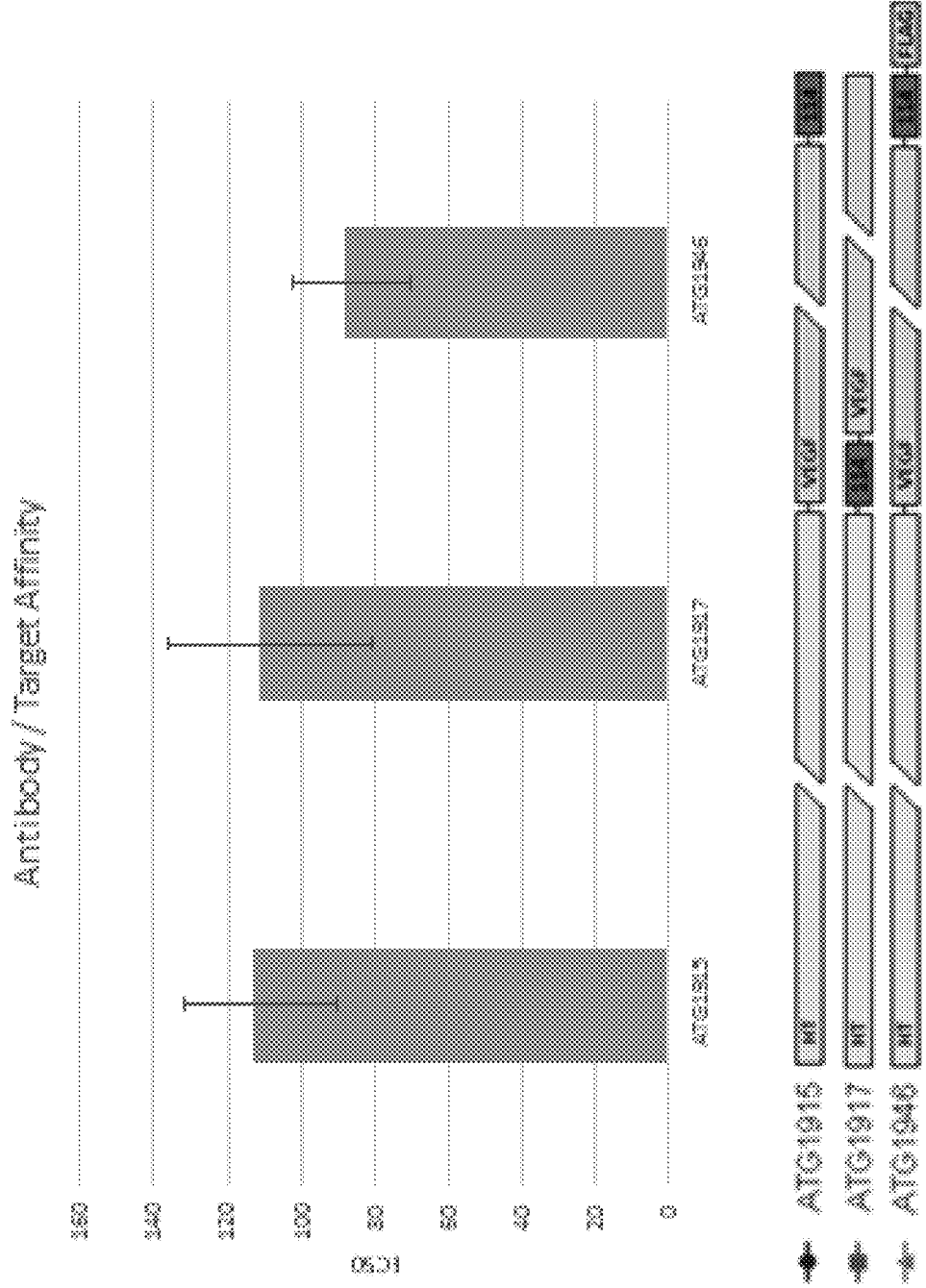
FIG. 10 demonstrates the affinity of the antibody for the target is unchanged by the position of NLpep114, as shown by anti-VEGFA antibody relative affinity through bioluminescence complementation dose response. The $EC_{50}$ values for the three VEGFA target constructs are shown as calculated off the dose response curves generated in FIG. 8.
Figure 11:
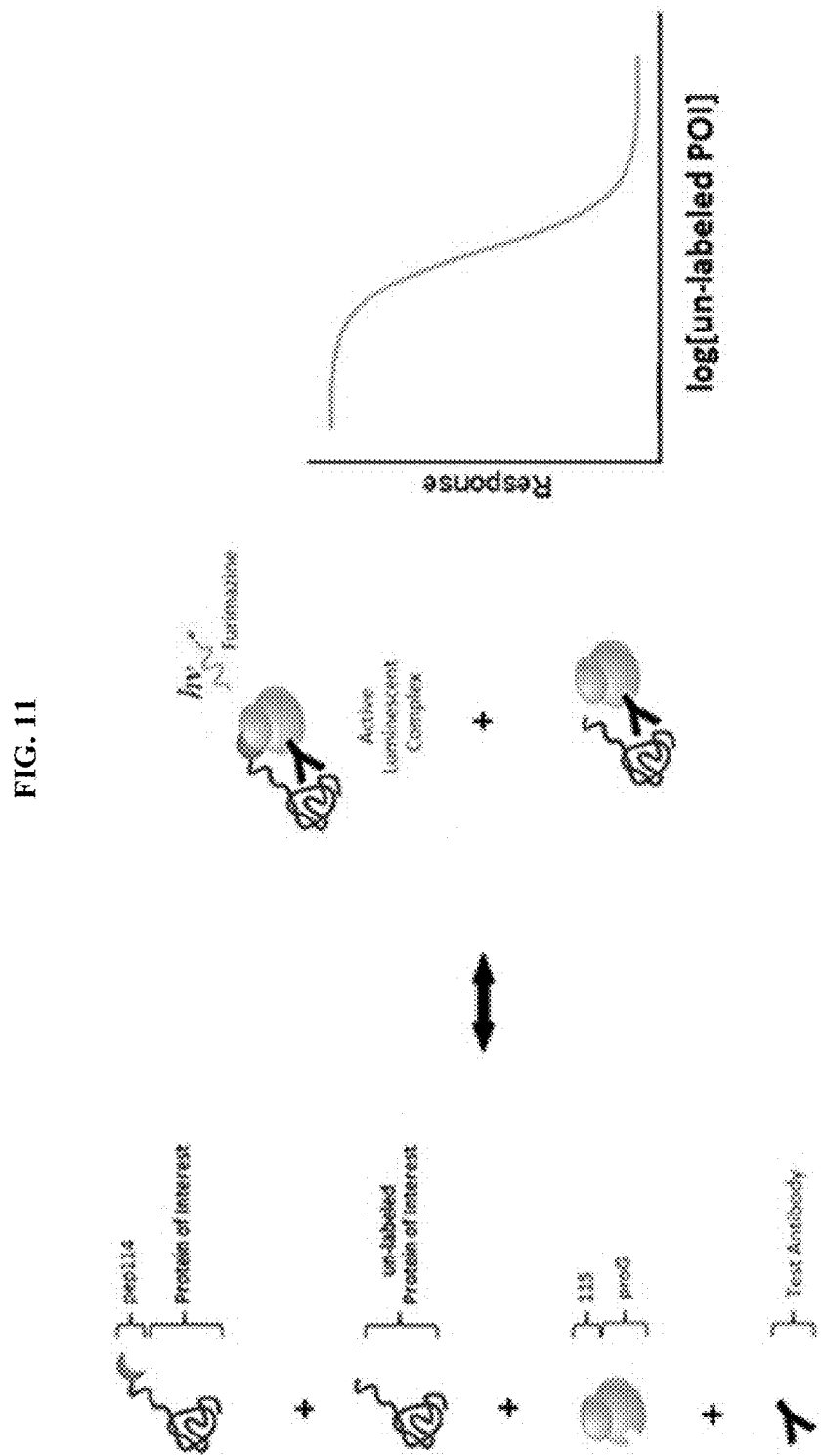
FIG. 11 depicts the schematic of how the assay components are used to quantify endogenous target protein along with prophetic data analysis by way of endogenous target protein competition with NLpep114 tagged target protein and antibody driven NANOLUC bioluminescence complementation between NLpoly11S-fused protein G and internally tagged NLpep114 target protein. Assay components configured to allow for quantitation of endogenous target protein of interest. Using the same target protein pep114 fusions and 11S-protein G fusions, one can quantitate the amount of endogenous target protein through binding competition resulting in a decrease in signal as endogenous target protein increases.
Figure 12:
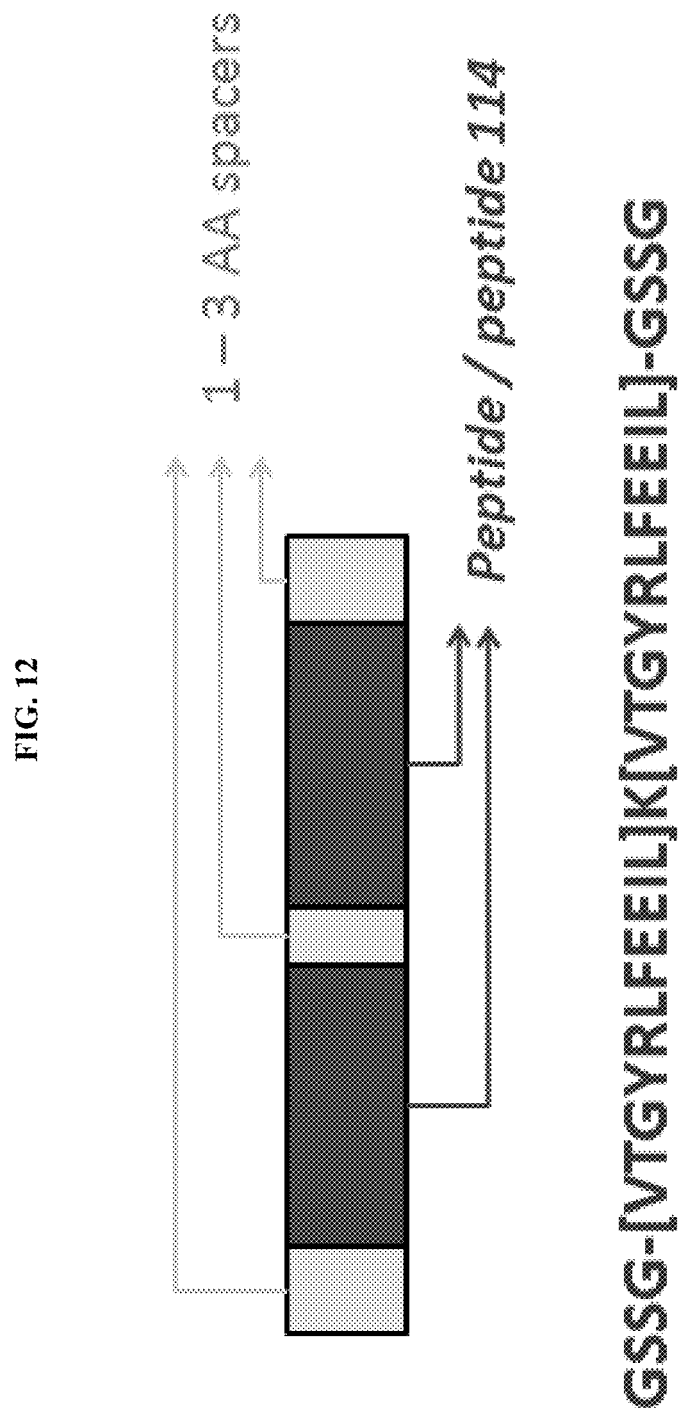
FIG. 12 depicts a schematic representation and sequence of the 114 tandem peptide (SEQ ID NO: 2581) used for internal tagging.

Experiments were conducted during development of embodiments of the present invention to demonstrate structural complementation between the non-luminescent polypeptide, NLpoly11S and the high affinity, non-luminescent peptide, NLpep86, as an experimental model. HALOTAG was selected as the target for insertion of the NLpep86. A number of HALOTAG—NLpep86 fusion proteins were generated by inserting a tandem of NLpep86 (high affinity, sequence GSSG-[VSGWRLFKKIS]-E-[VSGWRLFKKIS]-GSSG (SEQ ID NO: 2580)) at various sites within the HALOTAG protein (insertion sites: 18/19, 32/33, 78/79, 98/99). Initial experiments were performed in HeLa cells transiently transfected with NLpoly11S and the indicated HALOTAG-NLpep86 fusion proteins. The results show that it is possible to achieve structural complementation between NLpoly11S and NLpep86 inserted at different positions within HALOTAG (FIG. 4). HALOTAG function was determined by BRET (which requires the ability of modified HALOTAG to bind HALOTAG ligand, FIG. 4) or imaging of TMR-HT ligand labeled cells (FIG. 5). It was demonstrated that insertion of NLpep86 is compatible with HALOTAG function (FIG. 5). The observed efficiency of structural complementation using internal fusions varies between 1-40% relative to N- or C-terminal NLpep86 fusions to HALOTAG using NLpoly11S and NLpep86.

Example 2

Experiments were conducted to demonstrate test antibody driven NANOLUC bioluminescence complementation using an NLpep114 internally tagged target protein and an NLpoly11S tagged protein G.

Construction, Expression, and Purification of Protein G-11S

ATG-2071 (NLpoly11S-tagged protein G) plasmid (SEQ ID NO: 2576): Amino acids 303-497 from Immunoglobulin G-binding protein G [Uniprot P19909] were amplified from a synthetic gene (GenScript) to add a 6×His tag and cloned into pF5K (Flexi vector, CMV promoter) containing linker-NLpoly11S. The 6×His-proteinG-NLpoly11S fusion was then subcloned into pF1A (Flexi vector, T7 promoter; Promega) for bacterial expression.

NLpoly11S-tagged protein G was produced in an *E. coli* expression system by the Glucose/Rhamnose Auto-Induction Method. Briefly, plasmid ATG-2071 was transformed into *E. coli* KRX cells (Promega) using the manufacturer's recommended protocol and grown 17-22 hrs at 37° C. with shaking (275 rpm) in LB media (50 ml) containing antibiotic. This starter culture was diluted (1:100) into 250 ml of auto-induction media (LB media with glucose and rhamnose (0.05% each) and antibiotic) and grown 17-22 hrs at 25° C. with shaking (275 rpm). Cells were collected by centrifugation (5,000×g for 20 min at 4° C.), the media removed, and the bacterial cell pellet stored at −20° C.

Pelleted cells were re-suspended in 50 ml Lysis Buffer (100 mM HEPES (pH 7.5), 500 mM NaCl, 10 mM Imidazole, 0.5× FastBreak (Promega), 1× Protease Inhibitor Cocktail (Promega), 0.2 mg/ml lysozyme (Sigma) and 250 units of RQ1 DNase (Promega)), and then incubated at ambient temperature for 30 min with occasional mixing. The soluble fraction was separated by centrifugation (15,000×g for 20 min at 4° C.) and applied (1 ml/min) to a 5 ml HisTrap column (Life Technologies) equilibrated with Start Buffer (50 mM HEPES (pH 7.5), 500 mM NaCl, 10 mM Imidazole). After sample application, the resin was washed with 4 CVs Start Buffer. Bound protein was eluted with a 20 CV linear gradient, 0-100% Limit Buffer (50 mM HEPES (pH 7.5), 500 mM Imidazole). Fractions (2.5 ml) were analyzed by SDS/PAGE. Those with significant amounts of a major 41 kDa band (NLpoly11S/pG) and minimal contaminants were pooled and dialyzed against 1×PBS and stored at −20° C.

Methods for Expression Plasmid Construction for VEGFA Constructs

VEGF constructs ATG-1915 (SEQ ID NO: 2577), -1917 (SEQ ID NO: 2578) and -1946 (SEQ ID NO: 2579) were built by transferring VEGFA-165 fused to either NLpep114 and/or FLAG octapeptide (both synthetic genes; Gene Dynamics) into the vector pCIHN (Flexi vector, CMV promoter; Promega). This vector contains an N-terminal HALOTAG—with an IL6 secretion signal.

General Cell Transfection Protocol

NLpep114-target fusion construct DNA was diluted into carrier DNA (pGEM3Zf(-); Promega) at bug total DNA at a mass ratio of 1:10. DNA:FuGENE complexes were formed at a ratio of 1:3 (ug DNA/ul FuGENE), according to manufacturer's protocol (Promega). One part of the transfection complex was mixed with 20 parts (volume/volume) of HEK293T cells (ATCC) suspended at a density of $2\times10^5$ cells/ml in DMEM (Gibco)+10% FBS (Hyclone). Cells (50 ul/well) were dispensed into 96-well tissue culture plates and incubated in a humidified, 37° C./5% $CO_2$ incubator for 18-24 hours.

Target Antibody Driven NANOLUC Bioluminescence Complementation

HEK293T cells (ATCC) were transfected with three NLpep114-VEGFA DNAs as described above and incubated overnight. The cells were serum starved for 4 hours under the same conditions by replacing the media with an equal volume of (Gibco). NLpoly11S(15)pG in 1×PBS/0.1% BSA (Promega) was added (25 ul/well) to a final concentration of 0.5 ug/ml (12 nM). Anti-VEGF antibody (R&D Systems, #293) in 1×PBS/0.1% BSA (Promega) was added (25 ul/well) to a final concentration of 0-0.73 ug/ml (0-5.3 nM). After the addition of LCS Reagent (Promega, 100 ul/well, 10 µM final concentration), luciferase activity was measured using an Infinity F500 microtiter plate reader (Tecan).

FIGS. 6-11 demonstrate that when incubated together, the NLpep114-VEGF fusion protein, the NLpoly11S-protein G fusion protein, and the un-modified anti-VEGF antibody come together to form an active luciferase complex. The signal is measurable, but extremely low in the absence of antibody. Given the high $K_D$ of the NLpoly11S/NLpep114 interaction, non-facilitated complementation should be extremely low at the concentrations used. This indicates that the NLpoly11S fragment has some low level of residual luciferase activity. For ATG-1915 (HT-VEGF-114), this background signal increased by over 400-fold as the anti-VEGF antibody concentration increased from 0-0.73 ug/ml (0-5.3 nM).

The context of the NLpep114 tag influences the overall system performance. ATG-1915 with a C-terminal (external) NLpep114 tag has the highest signal. This construct suffers a 40% signal loss when the NLpep114 tag is slightly internalized by the addition of a C-terminal FLAG sequence (ATG-1946). When placed between two large domains, the signal is reduced 5-fold (ATG-1917). Note that while the total signal varies with the position of the NLpep114 tag, the calculated $EC_{50}$ remains constant. The context of the NLpep114 tag changes the level of complementation, but not the affinity of the NLpoly 11 S/NLpep114 pair.

Example 3

Figure 13:
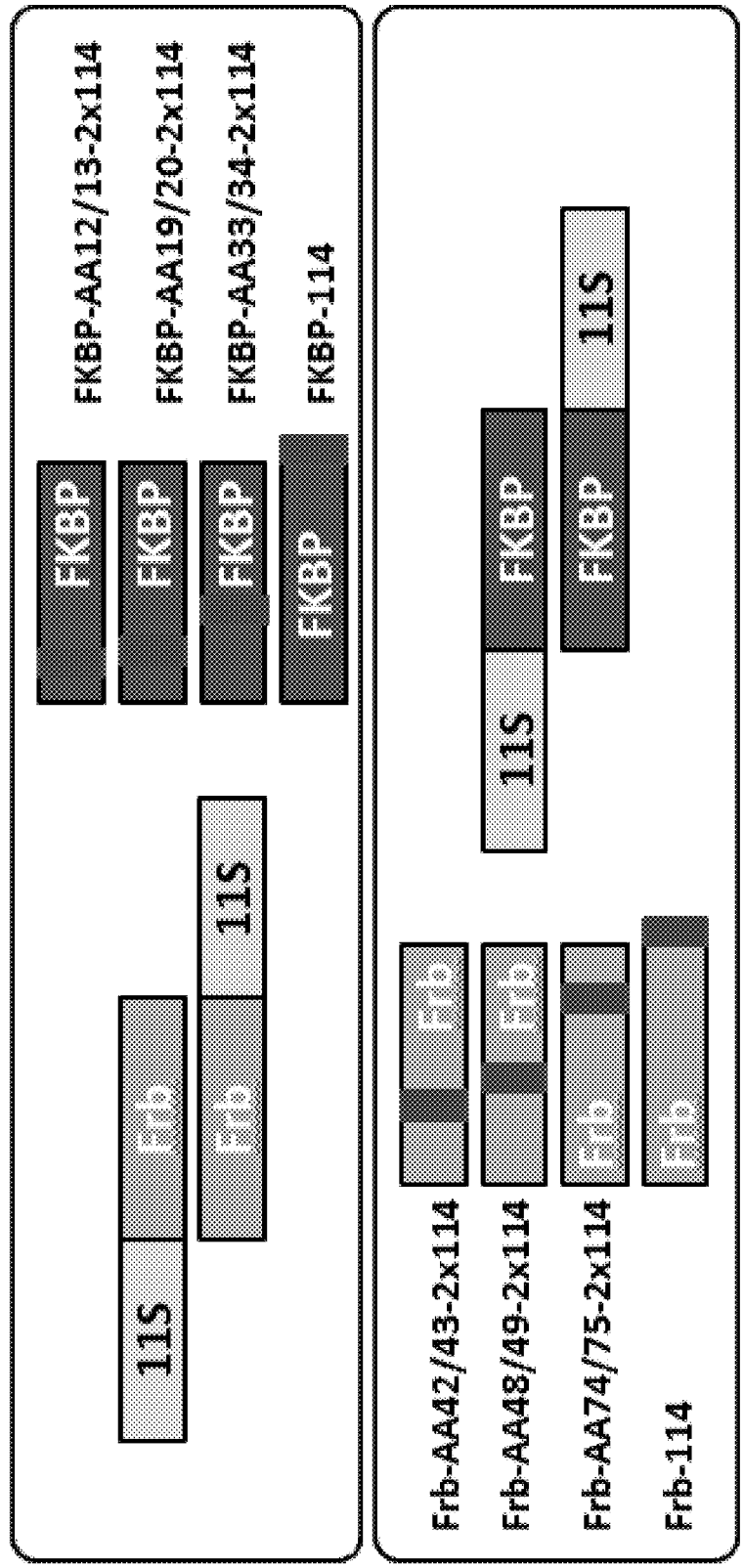
FIG. 13 depicts a schematic representation of FKBP/Frb fusion proteins. Shown are fusions of NLpoly11S fused to the C- or N-terminus of either FKBP or Frb, and the integration of the internal tag (NLpep114 tandem peptide=2×NLpep114) at different position within FKBP or Frb. The position of the integration site of the internal tag is indicated by the flanking amino acid positions of the host protein (e.g., AA12/13 indicates integration of 2×NLpep114 between amino acid 12 and 13 of FKBP).

Experiments were conducted to demonstrate facilitated NANOLUC bioluminescence complementation using the binding pair, FKBP and Frb (FIG. 13).

All transfections were performed as reverse transfections by mixing the transfection complex with a suspension of cells prior to plating. Briefly, a transfection mix (sufficient for one 96-well plate) was made containing 500 ul OptiMEM, 5 ug DNA, and 15 uL Fugene HD (Promega). The DNA of the complementation pair (Frb-X/FKBP-Y) was at a ratio of 1:1

For the transfection, the DNA of the complementation pair was used either un-diluted or at a dilution of 1:50. Total DNA content was adjusted to 5 ug using pGEM3Z as carrier DNA.

The transfection mix was mixed by gentle vortexing and incubated for 5-10 min at room temperature prior to use.

Cells were harvested by trypsination, washed, and diluted to a concentration of $2 \times 10^5$ cells/ml in DMEM+10% FBS. For the transfection, 0.5 ml transfection mix was added to 10 ml of cell suspension. The cell suspension was then plated into wells of a white, 96-well tissue culture plate (100 uL per well) and incubated 0/N at 37° C.

Figure 14:
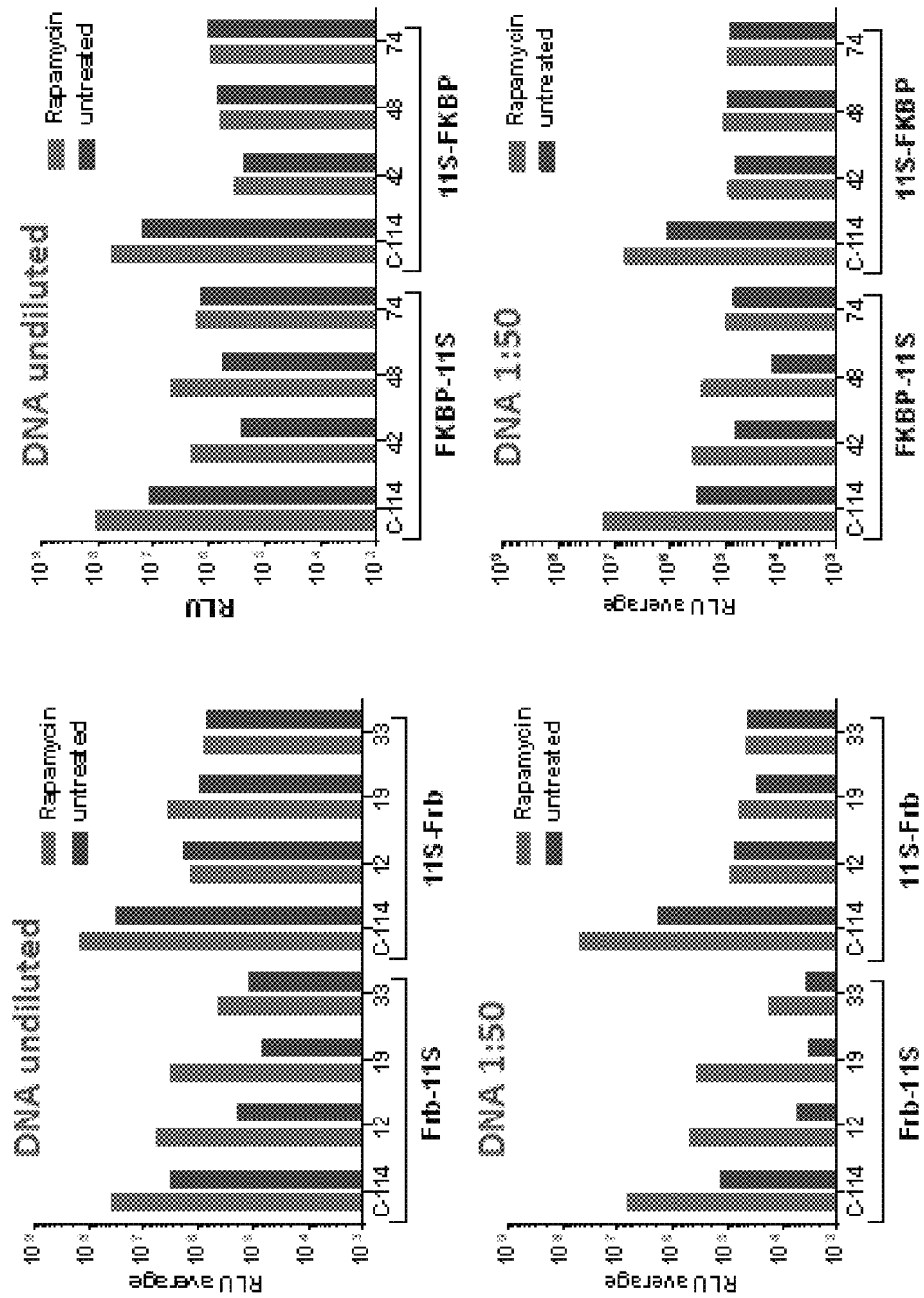
FIG. 14 demonstrates rapamycin-induced protein-protein interaction of FKBP/Frb using the internal tagging described herein. Position of the NLpep114 tandem peptide is indicated as C-terminal (C-114) or by the N-terminally flanking amino acid of the host protein (e.g. 12 indicates integration between AA12 and 13 within FKBP).
Figure 15:
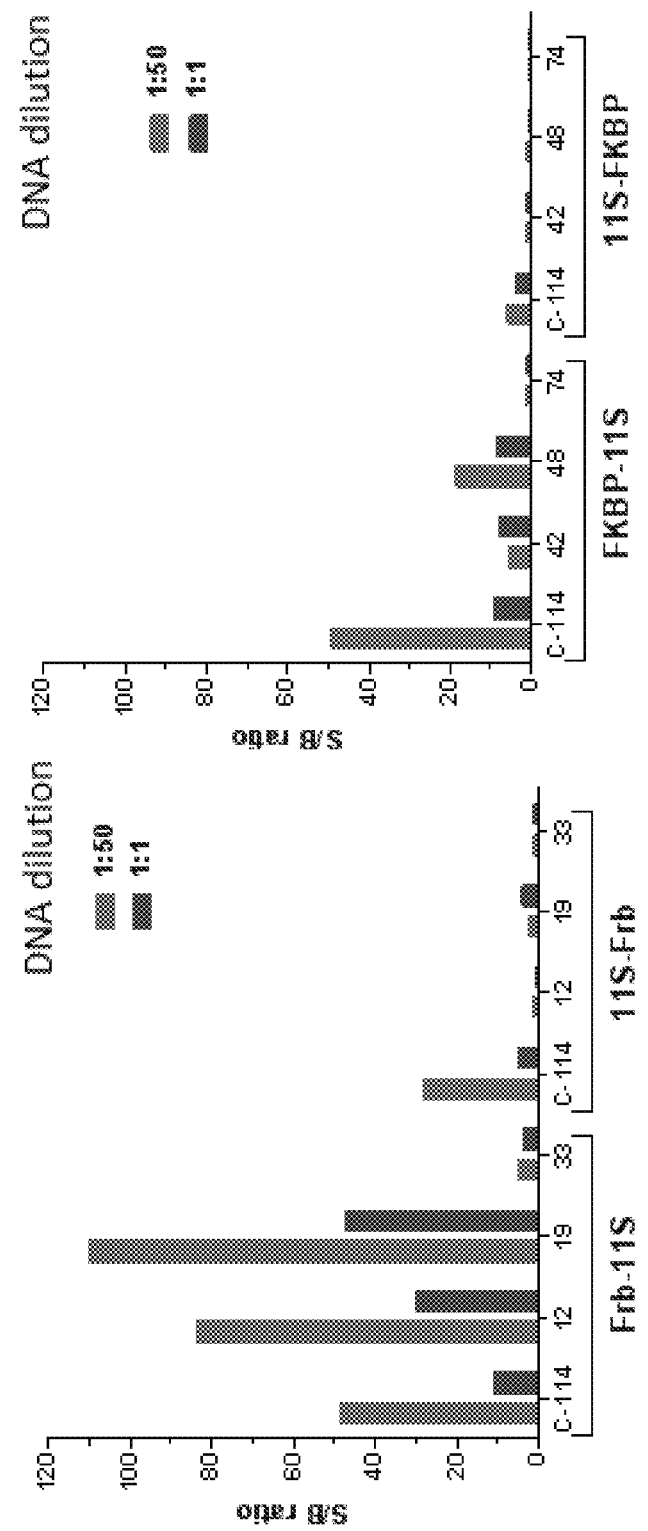
FIG. 15 demonstrates the conversion of the results shown in FIG. 15 into a relative change between untreated and rapamycin-treated sample (response ratio). The response ratio is calculated using the equation: response ratio= RLUrapamycin/RLUuntreated.
Figure 16:
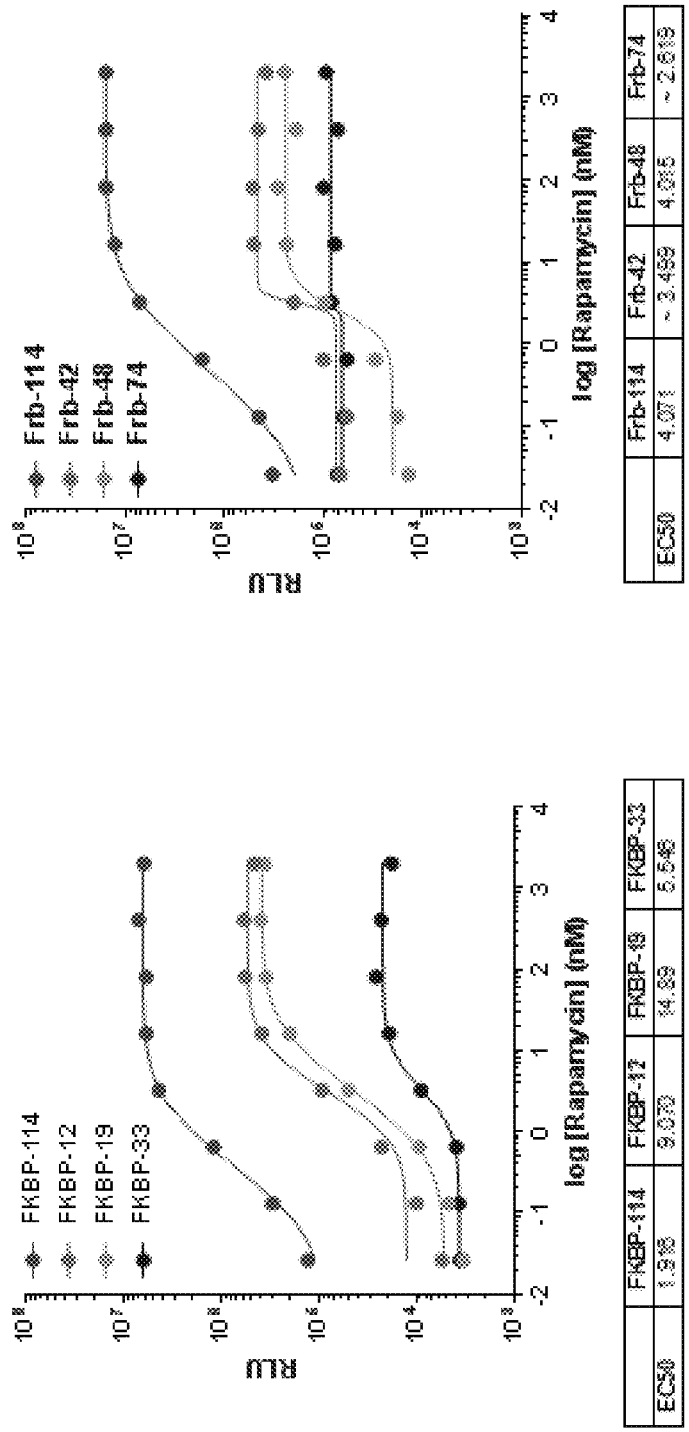
FIG. 16 demonstrates dose-dependent induction of the FKBP/Frb interaction by rapamycin using the internal tagging described herein.
Figure 17:
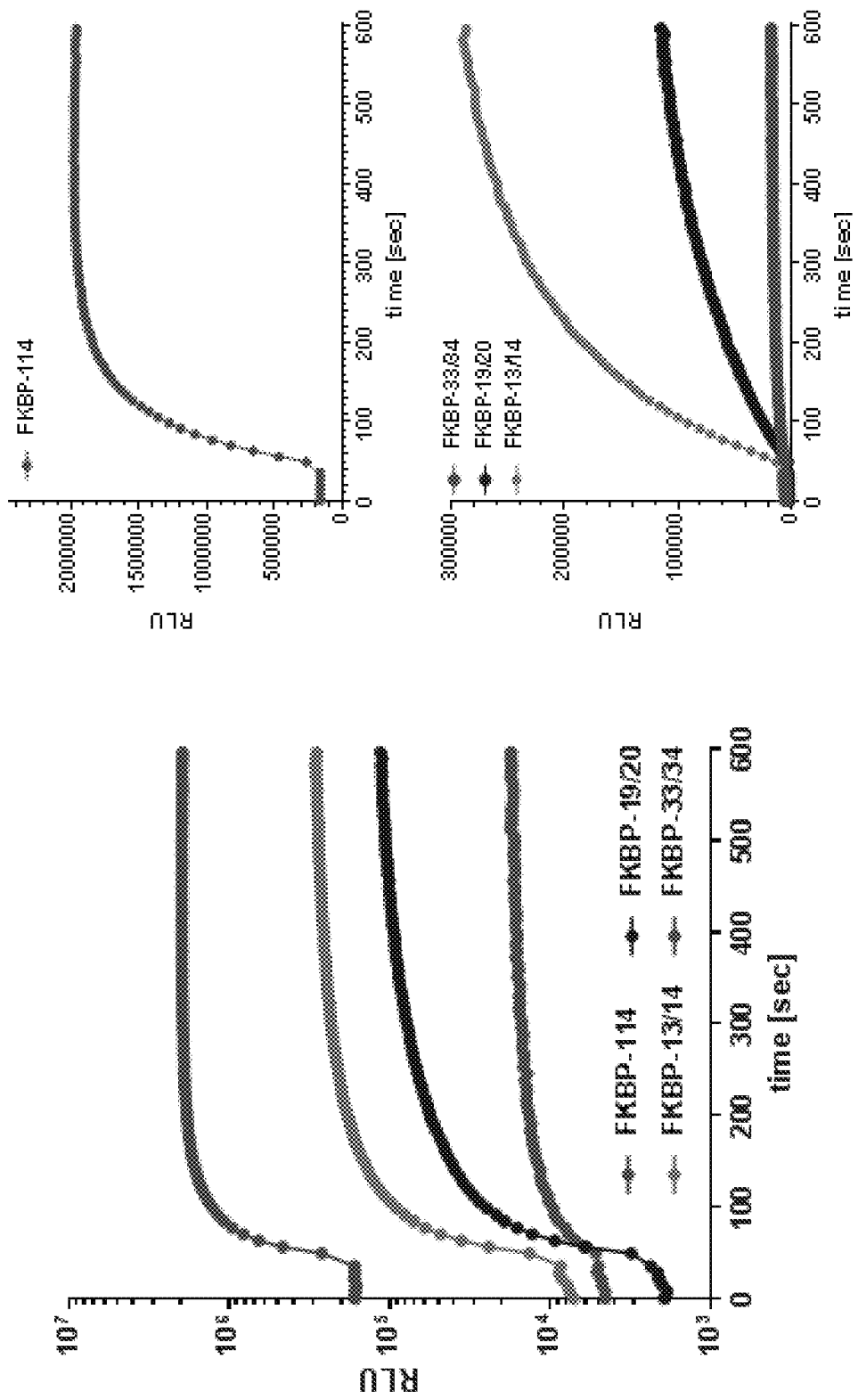
FIG. 17 demonstrates kinetic measurement of the rapamycin-induced FKBP/Frb interaction using the internal tagging described herein. All results are shown using Relative Light Units (RLU) as unit of measurement plotted either on a logarithmic (left) or linear scale (right).
Figure 18:
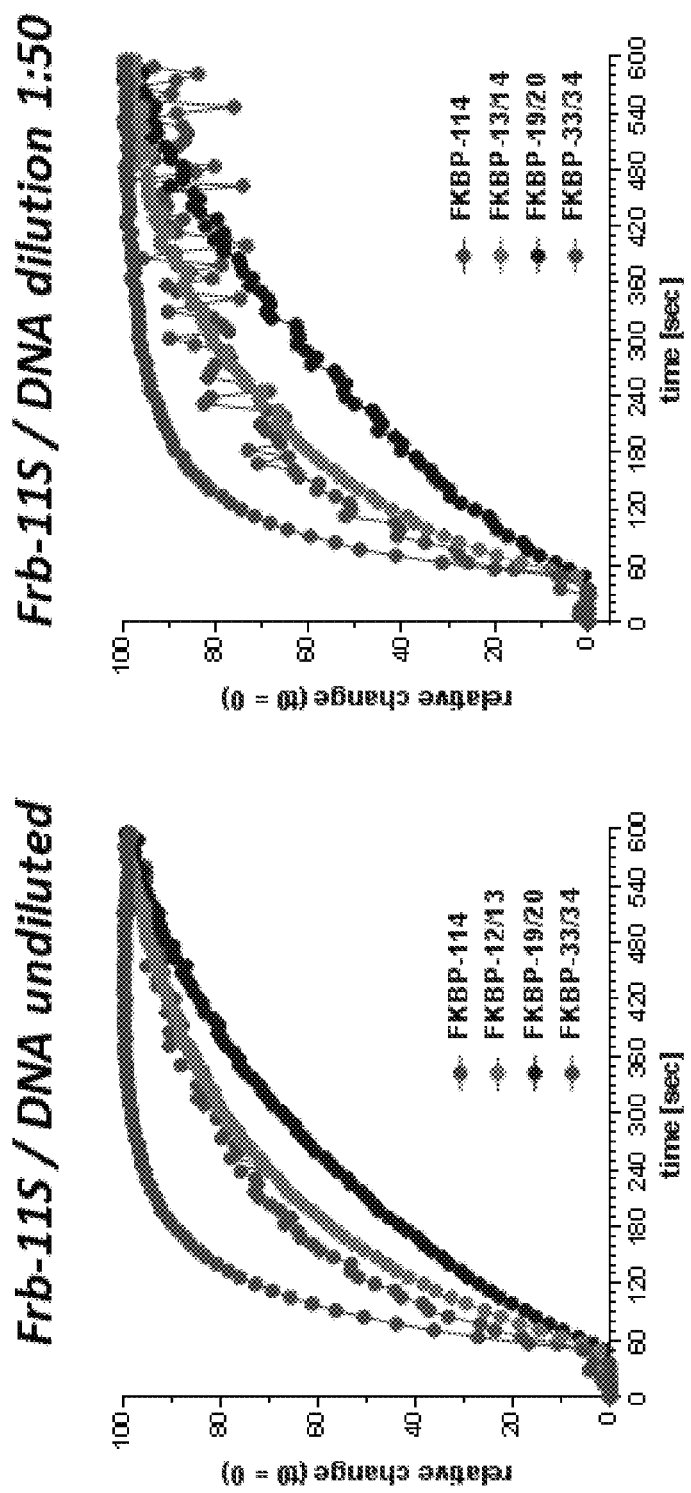
FIG. 18 demonstrates a normalized representation of results shown in FIG. 17 (left graph). For normalization, minimum and maximum values obtained for each individual trace were used as reference points (0% and 100% respectively).

Three different assays were performed on the transfected cells.

a) Endpoint assay using a single concentration of Rapamycin (FIGS. 14 and 15)
   Growth medium (DMEM+10% FBS) on the transfected cells was removed by aspiration, and 100 uL OptiMEM including Rapamycin (1 mM) and furimazine (10 mM) was added. The cells were incubated for 10 minutes at room temperature, and luminescence read on BMG Clariostar or Glomax Multi plus plate reader.

b) Endpoint assay—Rapamycin dose response (FIG. 16)
   Growth medium (DMEM+10% FBS) on the transfected cells was removed by aspiration, and 100 uL OptiMEM including a serial dilution of Rapamycin and furimazine (10 mM) was added. The cells were incubated for 10 minutes at room temperature, and luminescence read on BMG Clariostar or Glomax Multi plus plate reader.

c) Kinetic assay (FIGS. 17 and 18)
   Growth medium (DMEM+10% FBS) on the transfected cells was removed by aspiration, and 50 uL OptiMEM including furimazine (10 mM) was added. Luminescence detection was initiated on a BMG Clariostar plate reader, and 50 uL OptiMEM including Rapamycin (1 mM) and furimazine (10 mM) was injected onto the cells. Luminescence was continuously read.

Example 4

Internal High-Affinity NLpep finds use in a variety of embodiments. Cases arise in which neither the N-terminus nor the C-terminus represent attractive points for attachment of a protein tag. For example, 1) The protein terminus is not in the desired cellular localization. For instance, for a given membrane protein, it may be desired to have the tag on the extracellular side, but both termini are intracellular.

2) Terminal addition of a tag interrupts protein-protein interactions. For instance, many membrane proteins (such as ADRB2) have PDZ-binding motifs at their very C-terminus. Addition of a C-terminal tag would abolish these interactions and alter proper protein functioning.

3) It is desired for the tag to be placed spatially closer to a given site on the protein than the terminus allows.

4) N-terminal tag placement disrupts proper signal sequence function and cleavage.

5) The termini is already used for other tags or fusion proteins.

Example 5

Internal High-Affinity NLpep finds use in the measurement of surface expression of membrane proteins. It is commonly desired to measure the amount of a given protein expressed on the cell surface. This enables studies of:
   Receptor activation and internalization
   Receptor recycling from endosomes
   Regulated exocytosis
   Protein trafficking and secretion In some embodiments, the following experiments are configured so that purified an NLpoly, e.g., NLpoly11S, protein plus furimazine substrate can be added to the extracellular medium. Complementation with a high-affinity NLpep sequence, e.g., NLpep80, on the extracellular side of the plasma membrane can lead to spontaneous complementation, giving a luminescent signal that is directly proportional to the amount of protein on the surface.

a) The F508del mutation of the cystic fibrosis transmembrane conductance regulator (CFTR) is the most common cause of cystic fibrosis, and it prevents the protein from being correctly targeted to the plasma membrane, so it is instead degraded. Small molecule chaperones have been identified that can promote increased trafficking to the surface. To screen for such small molecules, it is beneficial to have a simple luminescent assay for quantifying surface expression of CFTR.

Tagging CFTR with the high-affinity NLpep allows quantification of surface expression, but both the N- and C-termini of CFTR are intracellular. Therefore, the NLpep tag is placed in one of the extracellular loops of the protein. In some embodiments, a Flag epitope tag is placed after residue Asn901 previously to provide an extracellular tag. Insertion of the high-affinity NLpep sequence at the same location in the F508del variant of CFTR allows one or more of the following:

1) Simple quantification of the amount of protein at the plasma membrane. Cells could be treated with compound libraries and positive control compounds known to promote proper trafficking, and the luminescence measured with live cells in the presence of a NLpoly, e.g., NLpoly11S, plus furimazine.

2) The cells are treated with a lytic reagent containing a NLpoly, e.g., NLpoly11S, plus furimazine in order to quantify the total amount of protein in the cell. Reduced protein degradation would increase the luminescent signal.

3) The glycosylation of CFTR that occurs during its maturation is easily detected as band shifting on a protein blot by addition of a NLpoly, e.g., NLpoly11S, plus furimazine in buffer to the blot membrane.

b) The trafficking of neurotransmitter receptors in and out of the plasma membrane is tightly regulated. AMPA receptors (AMPARs) mediate fast excitatory synaptic transmission, and synaptic strength is determined by the composition of AMPARs in the postsynaptic membrane, which is controlled by regulated trafficking of AMPAR subunits. Insertion of high-affinity NLpep into extracellular loops of AMPA receptors allows for straightforward measurement of protein levels and the kinetics of exocytosis and endocytosis.

All publications and patents mentioned in the above specification are herein incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11365402B2). An electronic copy of the "Sequence Listing" will also be available from the USPTO upon request and payment of the fee set forth in 37 CFR 1.19(b)(3).

We claim:

1. A method for detecting a stable interaction between a first amino acid sequence and a second amino acid sequence comprising:
   (a) placing (i) an internal fusion comprising an N-terminal segment of a first amino acid sequence of interest, a C-terminal segment of the first amino acid sequence of interest, and an internal tag between the N-terminal and C-terminal segments, wherein the internal tag comprises an amino acid sequence having less than 100% and greater than 45% sequence identity with SEQ ID NO: 2 inserted within the first amino acid sequence of interest, (ii) a second fusion comprising a second amino acid sequence of interest and an amino acid sequence having less than 100% and greater than 45% sequence identity with SEQ ID NO: 440, and (iii) a furimazine or coelenterazine substrate in conditions that allow for a possible stable interaction to occur between the first amino acid sequence of interest and the second amino acid sequence of interest, wherein a bioluminescent signal produced in the presence of a furimazine or coelenterazine substrate is substantially increased when the internal tag contacts the amino acid sequence having less than 100% and greater than 45% sequence identity with SEQ ID NO: 440, when compared to a bioluminescent signal produced in the presence of the substrate but in the absence of contact between the internal tag and the amino acid sequence having less than 100% and greater than 45% sequence identity with SEQ ID NO: 440; and
   (b) detecting, if present, a bioluminescent signal emitted, wherein detection of the bioluminescent signal indicates a stable interaction between the first amino acid sequence of interest and the second amino acid sequence of interest.

2. The method of claim 1, wherein said second fusion is an internal fusion or a traditional fusion.

3. The method of claim 1, wherein the first internal fusion is expressed from a first nucleic acid sequence and the second fusion is expressed from a second nucleic acid sequence.

4. The method of claim 3, wherein a single vector comprises the first nucleic acid sequence and the second nucleic acid sequence.

5. The method of claim 3, wherein the first nucleic acid sequence and the second nucleic acid sequence are on separate vectors.

6. The method of claim 3, wherein steps (a) and (b) comprise expressing the internal fusion and second fusion within a cell.

7. A method for detecting a stable interaction between a first amino acid sequence and a second amino acid sequence comprising:
   (a) creating an internal fusion by inserting an internal tag into the first amino acid sequence, such that said internal tag is neither at the N-terminus not the C-terminus of the first amino acid sequence, wherein the internal tag has less than 100% and greater than 45% sequence identity with SEQ ID NO: 440, and wherein a detectable bioluminescent signal is produced in the presence of a coelenterazine substrate when the internal tag contacts a peptide of SEQ ID NO: 2;
   (b) creating a second fusion of the second amino acid sequence and a complement peptide, wherein the complement peptide has less than 100% and greater than 45% sequence identity with SEQ ID NO: 2, and wherein a detectable bioluminescent signal is produced in the presence of a coelenterazine substrate when the complement peptide contacts a polypeptide of SEQ ID NO: 440;
   (c) placing the internal fusion, second fusion, and a coelenterazine substrate in conditions that allow for a possible stable interaction to occur between the first amino acid sequence and the second amino acid sequence to; and
   (d) detecting, if present, a bioluminescent signal emitted, wherein detection of the bioluminescent signal indicates a stable interaction between the first amino acid sequence and the second amino acid sequence.

8. The method of claim 7, wherein said second fusion is an internal fusion or a traditional fusion.

9. The method of claim 7, wherein the internal fusion is expressed from a first nucleic acid sequence coding for the first amino acid sequence and the internal tag, and the second fusion is expressed from a second nucleic acid sequence coding for the second amino acid sequence and the complement peptide.

10. The method of claim 9, wherein a single vector comprises the first nucleic acid sequence and the second nucleic acid sequence.

11. The method of claim 9, wherein the first nucleic acid sequence and the second nucleic acid sequence are on separate vectors.

12. The method of claim 9, wherein step (a) comprises expressing the internal fusion and second fusion within a cell.

13. A method comprising providing a polypeptide for use in an assay, the polypeptide comprising an N-terminal segment of a protein of interest, a C-terminal segment of a protein of interest, and an internal tag between the N-terminal and C-terminal segments, wherein the internal tag comprises an amino acid sequence having less than 100% and greater than 45% sequence identity with SEQ ID NO: 2 inserted within the protein of interest; wherein a detectable bioluminescent signal is produced in the presence of a coelenterazine substrate when the internal tag contacts a polypeptide consisting of SEQ ID NO: 440 wherein the polypeptide is not a naturally occurring polypeptide.

14. The method of claim 13, for detecting a target polypeptide in a sample comprising:
   (a) creating an internal fusion by inserting an internal tag into the target polypeptide, such that said internal tag is neither at the N-terminus not the C-terminus of the target polypeptide, wherein the internal tag has less than 100% and greater than 45% sequence identity with SEQ ID NO: 440, and wherein a detectable bioluminescent signal is produced in the presence of a coelenterazine substrate when the internal tag contacts a peptide of SEQ ID NO: 2;
   (b) adding to said sample:
      (i) a complement peptide that has less than 100% and greater than 45% sequence identity with SEQ ID NO: 2, and
      (ii) a coelenterazine substrate;
   (c) detecting, if present, a bioluminescent signal emitted, wherein detection of the bioluminescent signal indicates the presence of the target polypeptide in the sample.

15. The method of claim 14, wherein the sample comprises a cell.

16. The method of claim 15, wherein step (a) comprises expressing said internal fusion in said cell.

17. The method of claim 16, wherein step (b)(i) comprises expressing said complement peptide in said cell.

18. The method of claim 13, for detecting a target polypeptide in a sample comprising:
   (a) creating an internal fusion by inserting an internal tag into the target polypeptide, such that said internal tag is neither at the N-terminus not the C-terminus of the target polypeptide, wherein the internal tag has less than 100% and greater than 45% sequence identity with SEQ ID NO: 2, and wherein a detectable bioluminescent signal is produced in the presence of a coelenterazine substrate when the internal tag contacts a peptide of SEQ ID NO: 440;
   (b) adding to said sample:
      (i) a complement polypeptide that has less than 100% and greater than 45% sequence identity with SEQ ID NO: 440, and
      (ii) a coelenterazine substrate;
   (c) detecting, if present, a bioluminescent signal emitted, wherein detection of the bioluminescent signal indicates the presence of the target polypeptide in the sample.

19. The method of claim 18, wherein the sample comprises a cell.

20. The method of claim 19, wherein step (a) comprises expressing said internal fusion in said cell.

21. The method of claim 19, wherein step (b)(i) comprises said complement polypeptide in said cell.

22. The method of claim 13, for detecting alteration of an interaction between a first amino acid sequence and a second amino acid sequence by a potential inhibitory agent comprising:
   (a) creating an internal fusion by inserting an internal tag into the first amino acid sequence, such that said internal tag is neither at the N-terminus not the C-terminus of the first amino acid sequence, wherein the internal tag has less than 100% and greater than 45% sequence identity with SEQ ID NO: 2, and wherein a detectable bioluminescent signal is produced in the presence of a coelenterazine substrate when the internal tag contacts a polypeptide of SEQ ID NO: 440;
   (b) creating a second fusion of the second amino acid sequence and a complement polypeptide, wherein the complement polypeptide has less than 100% and greater than 45% sequence identity with SEQ ID NO: 440, and wherein a detectable bioluminescent signal is produced in the presence of a coelenterazine substrate when the complement polypeptide contacts a peptide of SEQ ID NO: 2;
   (c) placing the internal fusion, second fusion, and a coelenterazine substrate in conditions that allow for a possible stable interaction to occur between the first amino acid sequence and the second amino acid sequence;
   (d) detecting, if present, a bioluminescent signal emitted; wherein detection of the bioluminescent signal indicates a stable interaction between the first amino acid sequence and the second amino acid sequence;
   (e) adding the potential inhibitory agent to the internal fusion, second fusion, and a coelenterazine substrate;
   (f) detecting, if present, a bioluminescent signal emitted; and
   (g) comparing the bioluminescent signals of steps (d) and (f), wherein decrease in bioluminescent signal from step (d) to step (f) indicates inhibition of the interaction between the first amino acid sequence and the second amino acid sequence by the potential inhibitory agent.

23. The method of claim 22, wherein steps (a) and (b) comprise expressing the internal fusion and second fusion within a cell.

24. The method of claim 22, wherein the potential inhibitory agent is a peptide or small molecule.

25. The method of claim 13, for determining the structural conformation of a first amino acid sequence comprising:
   (a) creating an internal fusion by inserting an internal tag into the first amino acid sequence, such that said internal tag is neither at the N-terminus not the C-terminus of the first amino acid sequence, wherein the internal tag has less than 100% and greater than 45% sequence identity with SEQ ID NO: 2, wherein a detectable bioluminescent signal is produced in the presence of a coelenterazine substrate when the internal tag contacts a polypeptide of SEQ ID NO: 440, wherein a first structural conformation of the first amino acid sequence prevents access to the internal tag, and wherein a second structural conformation of the first amino acid sequence allows access to the internal tag;
   (b) placing the internal fusion and either (i) a complement polypeptide having less than 100% and greater than 45% sequence identity with SEQ ID NO: 440 or (ii) a second fusion of a second amino acid sequence and the complement polypeptide in the presence of a coelenterazine substrate;
   (c) detecting, if present, a bioluminescent signal emitted, wherein absence of the bioluminescent signal indicates the first amino acid sequence is adopting the first structural conformation, and wherein presence of the bioluminescent signal indicates the first amino acid sequence is adopting the second structural conformation.

26. The method of claim 25, wherein step (c) comprises:
   (i) detecting, if present, a bioluminescent signal emitted wherein the absence of the bioluminescent signal indicates the first amino acid sequence is adopting the first structural conformation;
   (ii) inducing a conformational change in the first amino acid sequence; and (iii) detecting, if present, a bioluminescent signal emitted wherein the presence of the bioluminescent signal indicates the first amino acid sequence is adopting the second structural conformation.

27. The method of claim 26, wherein inducing a conformational change is selected from: adding a protease that cleave a portion of the first amino acid sequence, addition an agent that binds to the first amino acid sequence, and altering the assay conditions.

28. The method of claim 13, for determining the structural conformation of a first amino acid sequence comprising:
   (a) creating an internal fusion by inserting an internal tag into the first amino acid sequence, such that said internal tag is neither at the N-terminus not the C-terminus of the first amino acid sequence, wherein the internal tag has less than 100% and greater than 45% sequence identity with SEQ ID NO: 440, wherein a detectable bioluminescent signal is produced in the presence of a coelenterazine substrate when the internal tag contacts a peptide of SEQ ID NO: 2, wherein a first structural conformation of the first amino acid sequence prevents access to the internal tag, and wherein a second structural conformation of the first amino acid sequence allows access to the internal tag;
   (b) placing the internal fusion and either (i) a complement peptide having less than 100% and greater than 45% sequence identity with SEQ ID NO: 2 or (ii) a second fusion of a second amino acid sequence and the complement peptide in the presence of a coelenterazine substrate;
   (c) detecting, if present, a bioluminescent signal emitted, wherein absence of the bioluminescent signal indicates the first amino acid sequence is adopting the first structural conformation, and wherein presence of the bioluminescent signal indicates the first amino acid sequence is adopting the second structural conformation.

29. The method of claim 28, wherein step (c) comprises:
   (i) detecting, if present, a bioluminescent signal emitted wherein the absence of the bioluminescent signal indicates the first amino acid sequence is adopting the first structural conformation;
   (ii) inducing a conformational change in the first amino acid sequence; and
   (iii) detecting, if present, a bioluminescent signal emitted wherein the presence of the bioluminescent signal indicates the first amino acid sequence is adopting the second structural conformation.

30. The method of claim 29, wherein inducing a conformational change is selected from: adding a protease that cleave a portion of the first amino acid sequence, addition an agent that binds to the first amino acid sequence, and altering the assay conditions.

* * * * *